(12) United States Patent
Rehm et al.

(10) Patent No.: US 12,048,718 B2
(45) Date of Patent: Jul. 30, 2024

(54) CHIMERIC ANTIGEN RECEPTOR AND CAR-T CELLS THAT BIND BCMA

(71) Applicant: Max-Delbrück-Centrum für Molekulare Medizin in der Helmholtz-Gemeinschaft, Berlin (DE)

(72) Inventors: Armin Rehm, Berlin (DE); Uta Elisabeth Höpken, Berlin (DE); Julia Bluhm, Berlin (DE); Wolfgang Uckert, Berlin (DE); Elisa Kieback, Berlin (DE); Stephen Marino, Berlin (DE)

(73) Assignee: MAX-DELBRÜCK-CENTRUM FÜR MOLEKULARE MEDIZIN IN DER HELMHOLTZ-GEMINSCHAFT, Berlin (DE)

( * ) Notice: Subject to any disclaimer, the term of this patent is extended or adjusted under 35 U.S.C. 154(b) by 409 days.

(21) Appl. No.: 16/307,854

(22) PCT Filed: Jun. 7, 2017

(86) PCT No.: PCT/EP2017/063862
§ 371 (c)(1),
(2) Date: Dec. 6, 2018

(87) PCT Pub. No.: WO2017/211900
PCT Pub. Date: Dec. 14, 2017

(65) Prior Publication Data
US 2019/0307797 A1    Oct. 10, 2019

(30) Foreign Application Priority Data

Jun. 7, 2016 (EP) .................................... 16173401

(51) Int. Cl.
| | | |
|---|---|---|
| *A61K 35/17* | (2015.01) | |
| *A61K 39/00* | (2006.01) | |
| *A61K 47/65* | (2017.01) | |
| *C07K 14/705* | (2006.01) | |
| *C07K 16/28* | (2006.01) | |
| *C12N 15/62* | (2006.01) | |
| *C12N 15/85* | (2006.01) | |

(52) U.S. Cl.
CPC .............. *A61K 35/17* (2013.01); *A61K 47/65* (2017.08); *C07K 14/70596* (2013.01); *C07K 16/2878* (2013.01); *C12N 15/62* (2013.01); *C12N 15/85* (2013.01); *A61K 2039/505* (2013.01); *C07K 2317/24* (2013.01); *C07K 2317/33* (2013.01); *C07K 2317/34* (2013.01); *C07K 2317/622* (2013.01); *C07K 2317/73* (2013.01); *C07K 2319/03* (2013.01)

(58) Field of Classification Search
CPC . A61K 35/17; C07K 16/2878; C07K 2317/24
See application file for complete search history.

(56) References Cited

U.S. PATENT DOCUMENTS

| | | | |
|---|---|---|---|
| 10,144,782 B2 * | 12/2018 | Oden | ................. A61K 47/6867 |
| 2007/0111270 A1 | 5/2007 | Zhang et al. | |
| 2010/0099103 A1 | 4/2010 | Hsieh et al. | |

FOREIGN PATENT DOCUMENTS

| | | | | |
|---|---|---|---|---|
| WO | WO 2013/075027 A2 | 5/2013 | | |
| WO | WO-2013154760 A1 * | 10/2013 | ............. | A61K 39/00 |
| WO | WO 2014/020056 A1 | 2/2014 | | |
| WO | WO 2014/031687 A1 | 2/2014 | | |
| WO | WO 2014/068079 A1 | 5/2014 | | |
| WO | WO-2014068079 A1 * | 5/2014 | ......... | A61K 47/6867 |
| WO | WO-2015052538 A1 * | 4/2015 | ............. | A61K 35/17 |
| WO | WO 2015/086548 A1 | 6/2015 | | |
| WO | WO 2015/128509 A1 | 9/2015 | | |
| WO | WO 2015/128653 A2 | 9/2015 | | |
| WO | WO 2015/132604 A1 | 9/2015 | | |
| WO | WO 2015/150327 A1 | 10/2015 | | |
| WO | WO 2015/157399 A1 | 10/2015 | | |
| WO | WO-2015158671 A1 * | 10/2015 | ............. | A61K 35/17 |
| WO | WO 2015/166073 A1 | 11/2015 | | |
| WO | WO-2015166073 A1 * | 11/2015 | ......... | A61K 47/6849 |
| WO | WO 2016/014535 A1 | 1/2016 | | |
| WO | WO 2016/014565 A2 | 1/2016 | | |
| WO | WO-2016014789 A2 * | 1/2016 | ........... | A61K 38/177 |
| WO | WO 2016/026742 A1 | 2/2016 | | |
| WO | WO 2016/033570 A1 | 3/2016 | | |
| WO | WO 2016/044811 A1 | 3/2016 | | |

\* cited by examiner

*Primary Examiner* — Amy E Juedes
*Assistant Examiner* — Brian Hartnett
(74) *Attorney, Agent, or Firm* — Knobbe, Martens, Olson & Bear, LLP

(57) ABSTRACT

The invention relates to an isolated chimeric antigen receptor polypeptide (CAR), wherein the CAR comprises an extracellular antigen-binding domain, comprising an antibody or antibody fragment that binds a B Cell Maturation Antigen (BCMA) polypeptide. The CAR preferably binds an epitope comprising one or more amino acids of residues 13 to 32 of the N-terminus of human BCMA. The invention further relates to a nucleic acid molecule encoding the CAR of the invention, a genetically modified immune cell, preferably a T cell, expressing the CAR of the invention and the use of said cell in the treatment of a medical disorder associated with the presence of pathogenic B cells, such as a disease of plasma cells, memory B cells and/or mature B cells, in particular multiple myeloma, non-Hodgkin's lymphoma or autoantibody-dependent autoimmune diseases.

Figure 1:
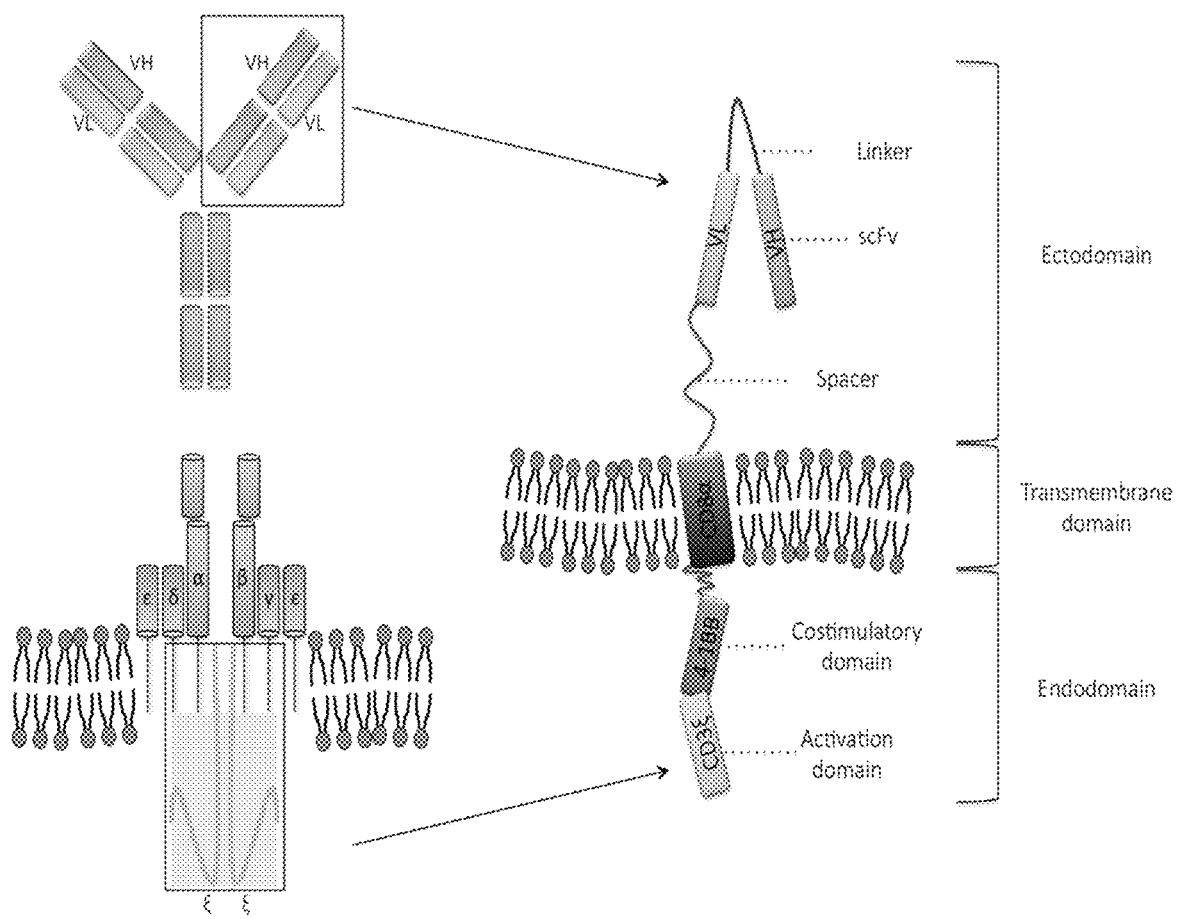

23 Claims, 18 Drawing Sheets
Specification includes a Sequence Listing.

Fig. 2
CAR IX.
CD28 Backbone
CAR X.
CAR XI. (w/o codon optimization)
CAR XV.
4-1BB Backbone
CAR XVI.
CAR XVII. (w/o codon optimization)

Fig. 3

| | Leader | scFv | Order | Linker | Hinge | Trans-membrane domain | Costimulatory domain | Activation domain |
|---|---|---|---|---|---|---|---|---|
| IX | Igκ | humanized | VH - VL | Whitlow | IgG1 | CD28 | CD28 | CD3ζ |
| X | Igκ | humanized | VL - VH | Whitlow | IgG1 | CD28 | CD28 | CD3ζ |
| XI | Igκ | Humanized (w/o codon opt.) | VH - VL | Whitlow | IgG1 | CD28 | CD28 | CD3ζ |
| XII | Igκ | humanized | VH - VL | Whitlow | IgG4 (Hi - CH2 - CH3) | CD28 | CD28 | CD3ζ |
| XIII | Igκ | humanized | VH - VL | Whitlow | IgG4 (Hi - CH3) | CD28 | CD28 | CD3ζ |
| XIV | Igκ | humanized | VH - VL | Whitlow | IgG4 (Hi) | CD28 | CD28 | CD3ζ |
| XV | Igκ | humanized | VL - VH | Whitlow | IgG1Δ | CD8α | 4-1BB | CD3ζ |
| XVI | Igκ | humanized | VL - VH | Whitlow | IgG1Δ | CD8α | 4-1BB | CD3ζ |
| XVII | Igκ | humanized | VL - VH | Whitlow | IgG1Δ | CD8α | 4-1BB | CD3ζ |

Fig. 4

J22.9 hHC FSY Alterations

Sequence was codon optimized for *homo sapiens*

81% homology to original sequence after codon optimization

```
Score            Expect      Identities      Gaps          Strand
338 bits(374)    2e-97       291/360(81%)    0/360(0%)     Plus/Plus J22.9   1    GAAGTGCAGCTGGTCGAATCTGGAGGAGGCCTGGTTCAGCCTGGTGGCAGCCTTAGGCTC   60
             ||||| |||||| || |||||| |||  ||||| |||||||| ||  |  |||  |||
C.O.    1    GAGGTGCAGCTGGTGGAATCTGGCGGAGGACTGGTGCAGCCTGGCGGCTCTCTGAGACTG   60

J22.9   61   TCTTGTGCAGCCTCTGGCTTTACCTTCTCACGGGTATGGTTCAGCTGGGTGAGACGGCT   120
             |||||||| | || ||  ||||||  |  | ||||| ||    ||  || |  |  |
C.O.    61   TCTTGTGCCGCCAGCGGCTTCACCTTCAGCCGGTACTGGTTTAGCTGGGTGCGCCAGGCC   120

J22.9   121  CCAGGGAAAGGTCTGGTGTGGGTAGGGGAGATAAACCCCAGCAGCAGCACGATCAACTAT   180
             || || || |    |||||||  | || |||||||||||||||||||| || ||||| |
C.O.    121  CCTGGCAAGGGACTGGTGTGGGTGGGAGAGATCAACCCCAGCAGCAGCACCATCAACTAC   180

J22.9   181  GCTCCGTCACTGAAAGACAAGTTCACCATTTCCCGCGATAATGCCAAGAACACTCTCTAC   240
             || || || ||| | |||||||||||||| |  |  ||||| |||||||||| || ||
C.O.    181  GCCCCCAGCCTGAAGGACAAGTTCACCATCAGCAGAGACAACGCCAAGAACACCCTGTAC   240

J22.9   241  TTGCAGATGAATTCCCTTCGAGCCGAGGATACAGCCGTGTACTACTGCGCCAGTCTGTAC   300
             || ||||| || || |  | | || || || || ||||| |||||| |||| |  ||
C.O.    241  CTGCAGATGAACAGCCTGCGGGCCGAGGACACCGCCGTGTACTACTGTGCCAGCCTGTAC   300

J22.9   301  TACGACTATGGGGACGCATACGACTATTGGGACAAGGCACACTGGTGACTGTTAGCTCC   360
             |||||||| ||||| || || || ||||||||||||||||| ||||||||| |||||||
C.O.    301  TACGACTACGGCGACGCCTACGATTACTGGGGCCAGGGCACAACTGGTGACTGTTAGCTCC   360
```

J22.9 hLC E Alterations

Sequence was codon optimized for *homo sapiens*

78% homology to original sequence after codon optimization

```
Score            Expect      Identities      Gaps          Strand
262 bits(290)    2e-74       253/323(78%)    4/323(1%)     Plus/Plus J22.9   68   GACATCGTGATGACCCAGTCTCCTGCTACCCTGAGCGTTTCTCCCGGTGAAAGGGCCACA   127
             |||||||||||| ||||| ||  | || |||| ||   | || | | |||||| ||
C.O.    1    GACATCGTGATGACACAGAGCCCTGCCACCCTGAGCGTGTCCCCAGGCGAAAGAGCTACC   60

J22.9   128  CTCAGCTGCAAAGCCTCTCAAAGCGTGGAGAGCAATGTCGCCTGGTATCAGCAGAAACCT   187
             || |||||||||  ||| |  |||   || |||||||| ||||||||||||||| ||
C.O.    61   CTGAGCTGCAAAGCCAGCCAGAGCGTGGAAAGCAATGTGGCCTGGTATCAGCAGAAGCCC   120

J22.9   188  GGCCAAAGTCCCGAGAGCACTGATCTATTCGGCATCA--TTGGCCTTTCGGCATACCAG   245
             |||| || |||  | || | | ||| |   | ||||  |  |  | ||  | | ||
C.O.    121  GGACAGAGCCCTGAGAGCCTGATCTA---CAGCGCCAGCCTGGAGATTCAGCGGCATCCCGC   178

J22.9   246  CACGGTTTAGTGGCTCAGGGAGTGGGACTGATTCACTCTGACGATTAGCTCCCTTCAGT   305
             |  || ||||  ||| | || || ||||  || ||||| ||| || | |  ||  ||
C.O.    179  CCAGGTTTAGCGGCTCTGGCAGCGGCACCGAGTTCACCCTGACAATCAGCAGCCTGCAGA   238

J22.9   306  CAGAGGATTTCGCCGTTTACTACTGTCAGCAGTACAACAACTATCCGCTCACATTCGGAG   365
             | ||||| ||||||| |||||||| |||||||||||||| ||  |||| ||||| ||||
C.O.    239  GCGAGGACTTTGCCGTGTATTACTGCCAGCAGTACAACAACTACCCCCTGACCTTCGGAG   298

J22.9   366  CTGGAACCAAGCTCGAACTGAAG   388
             | || ||||| ||||| ||||||
C.O.    299  GCGGCACCAAGCTGGAGCTGAAG   321
```

(J22.9 = original mAb; C.O. = codon optimized)

Figure 11:
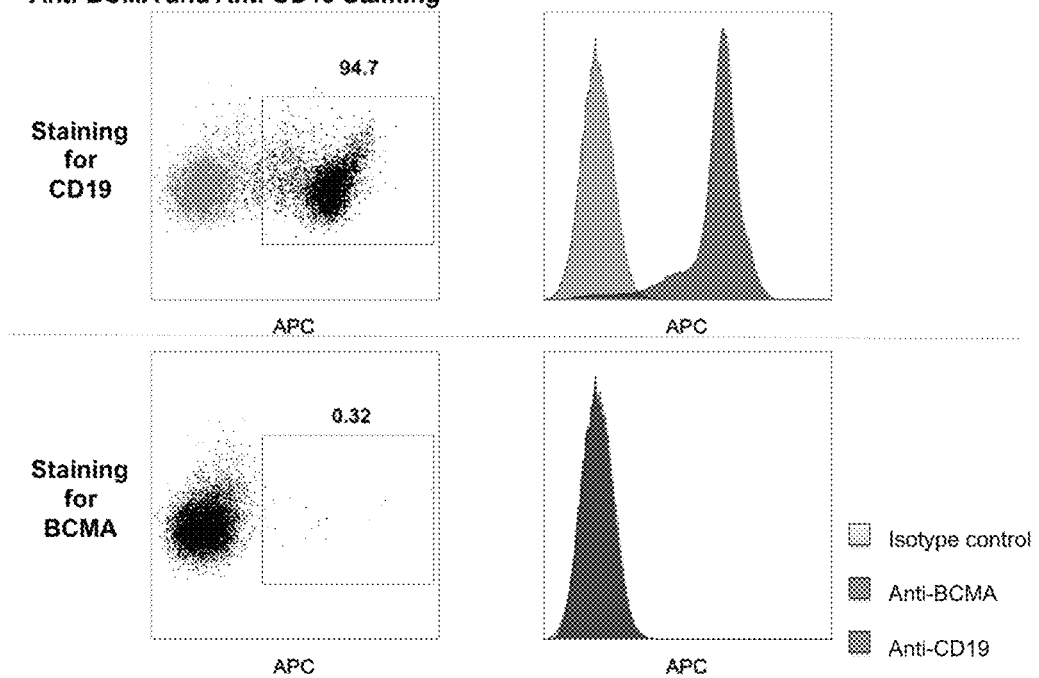

Fig. 11
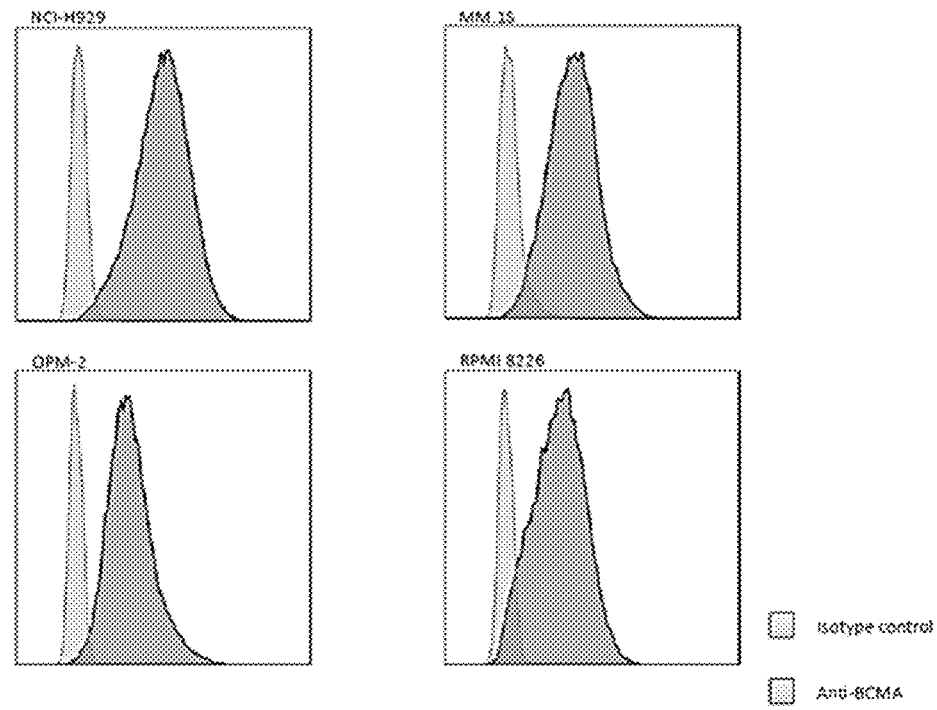
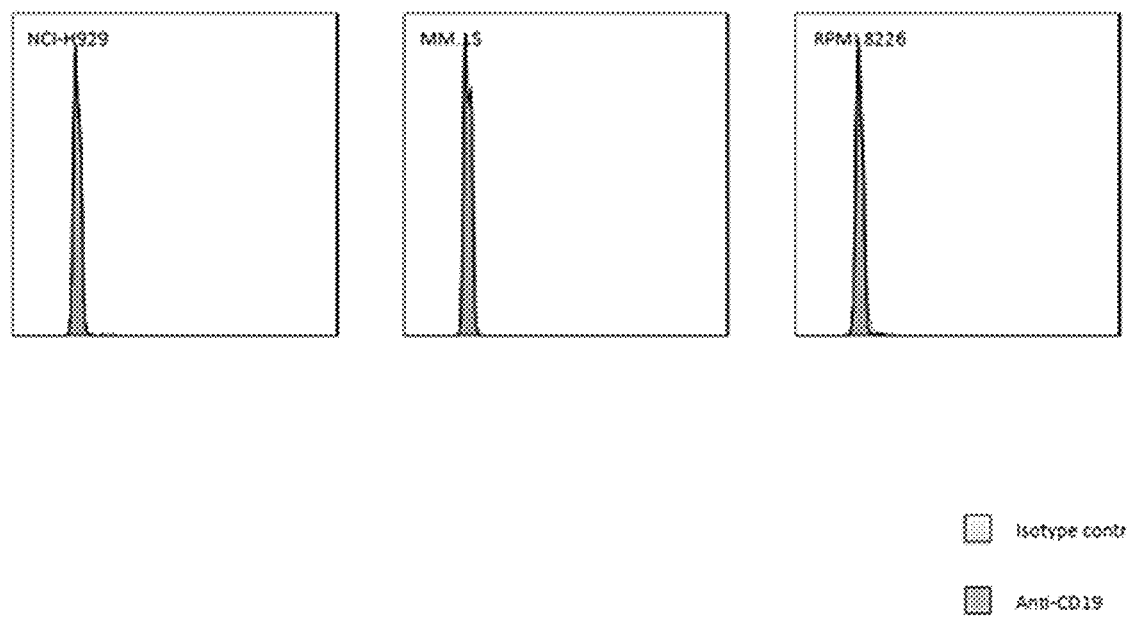

Fig. 11 (cont.)
B Cell Lymphoma Cell Lines
Anti-BCMA Staining
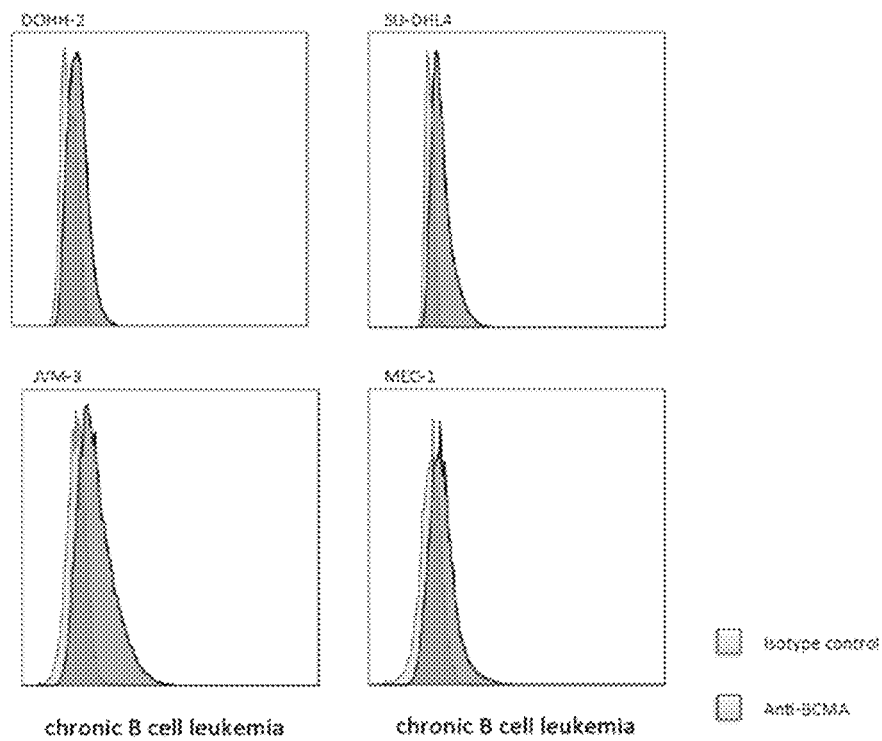
B Cell Lymphoma Cell Lines
Anti-CD19 Staining
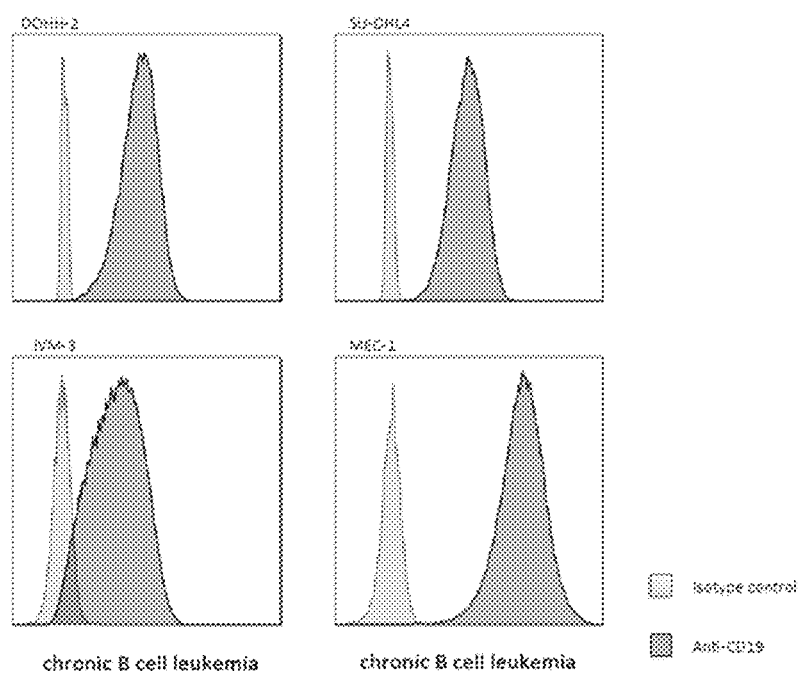

Fig. 11 (cont.)
Other Target Cell lines
Anti-BCMA Staining
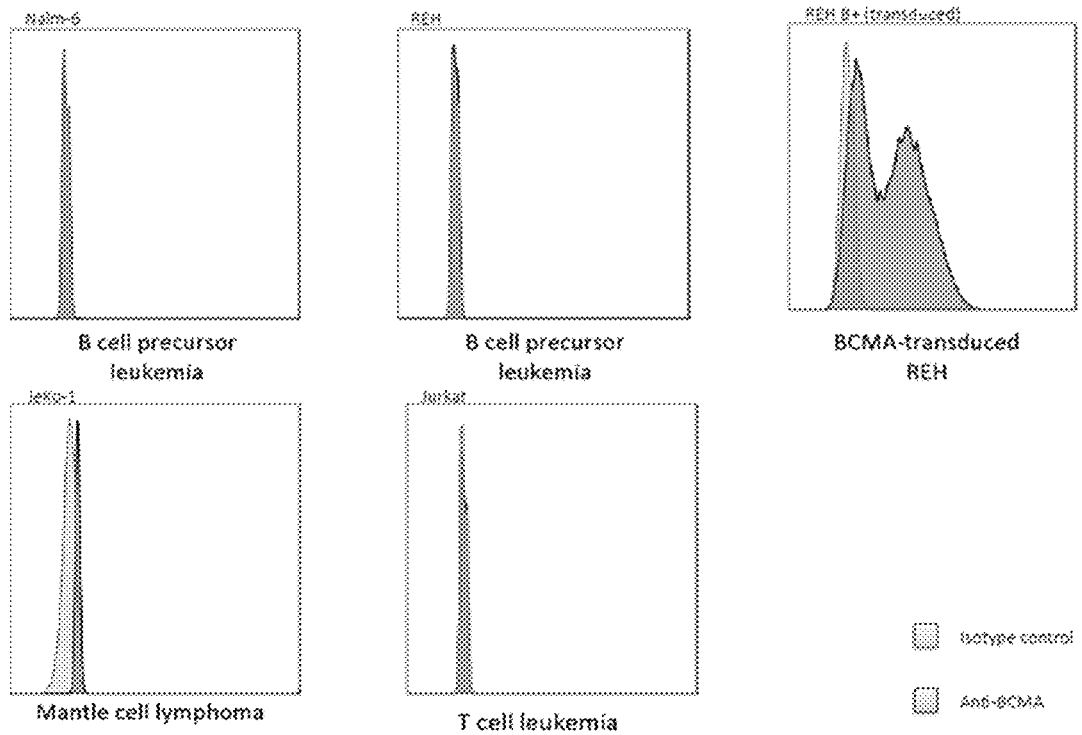
Other Target Cell lines
Anti-CD19 Staining
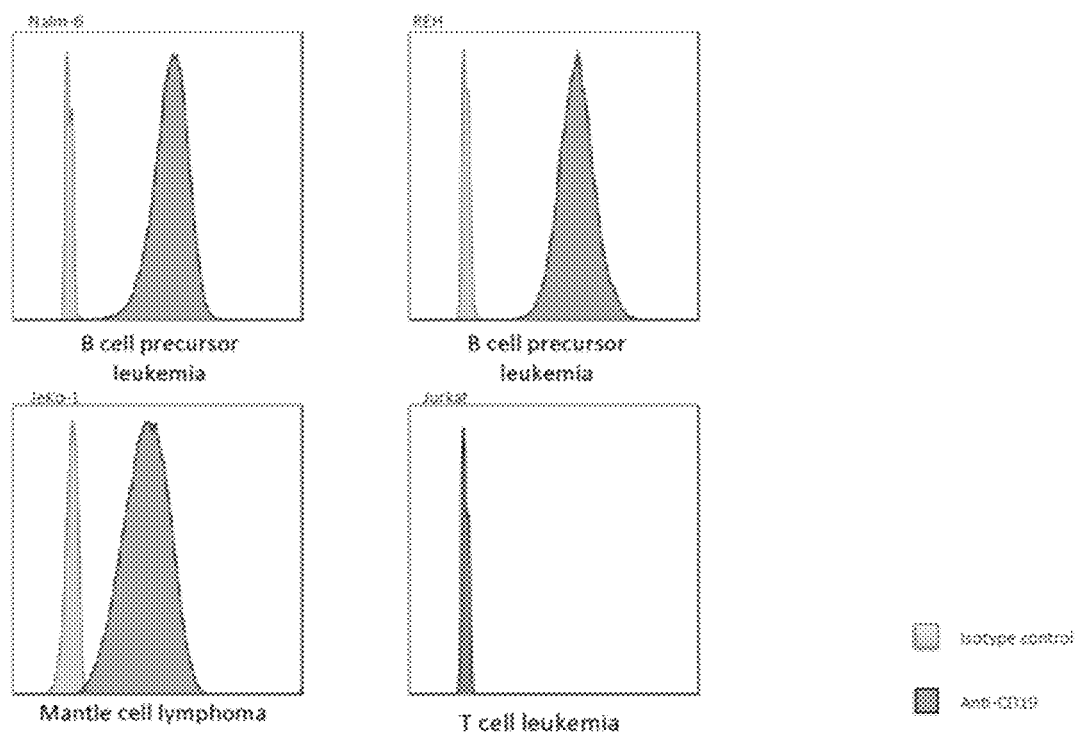

Fig. 13

HC

```
        1         10        20        30        40        50
HCg     XVQLXXSGGGLVQPGGSLXLSCAASGXXFXXYXXXWVRXAPGKGLXXXGX
HCm     QVQLQQSGGGLVQPGGSLKLSCAASGIDFSRYWMSWVRRAPGKGLEWIGE
HCpH    EVQLVESGGGLVQPGGSLRLSCAASGFTFDDYWMSWVRQAPGKGLEWVGE
hHC01   EVQLVESGGGLVQPGGSLRLSCAASGFTFSRYWMSWVRQAPGKGLVWVGE
hHC02   EVQLVESGGGLVQPGGSLRLSCAASGFTFSRYWXSWVRQAPGKGLVWVGE
hHC03   EVQLVESGGGLVQPGGSLRLSCAASGFTFSRYXMXWVRQAPGKGLVXVGX
hHC04   EVQLVESGGGLVQPGGSLRLSCAASGFTFSRYWISWVRQAPGKGLVWVGE
hHC05   EVQLVESGGGLVQPGGSLRLSCAASGFTFSRYWFSWVRQAPGKGLVWVGE
hHC06   EVQLVESGGGLVQPGGSLRLSCAASGFTFSRYWISWVRQAPGKGLVWVGE
hHC07   EVQLVESGGGLVQPGGSLRLSCAASGFTFSRYWFSWVRQAPGKGLVWVGE 51        60        70        80        90       100
HCg     INPXXSTINYAPSLKXXFXISRDNAKNTLYLQMXXXRSEDTAXYYCASXX
HCm     INPDSSTINYAPSLKDKFIISRDNAKNTLYLQMSKVRSEDTALYYCASLY
HCpH    INPDSSTINYAPSLKGRFTISRDNAKNTLYLQMNSLRAEDTAVYYCASLY
hHC01   INPDSSTINYAPSLKDKFTISRDNAKNTLYLQMNSLRAEDTAVYYCASLY
hHC02   INPXXSTINYAPSLKDKFTISRDNAKNTLYLQMNSLRAEDTAVYYCASLY
hHC03   INPDSSTINYAPSLKDKFTISRDNAKNTLYLQMNSLRAEDTAVYYCASXX
hHC04   INPNSSTINYAPSLKDKFTISRDNAKNTLYLQMNSLRAEDTAVYYCASLY
hHC05   INPNSSTINYAPSLKDKFTISRDNAKNTLYLQMNSLRAEDTAVYYCASLY
hHC06   INPSSSTINYAPSLKDKFTISRDNAKNTLYLQMNSLRAEDTAVYYCASLY
hHC07   INPSSSTINYAPSLKDKFTISRDNAKNTLYLQMNSLRAEDTAVYYCASLY 101       110
HCg     XDYGDXXDYWGQGTXVTVSS
HCm     YDYGDAMDYWGQGTSVTVSS
HCpH    YDYGDAMDYWGQGTLVTVSS
hHC01   YDYGDAMDYWGQGTLVTVSS
hHC02   XDYGDAXDYWGQGTLVTVSS
hHC03   XDYGDXMDYWGQGTLVTVSS
hHC04   YDYGDAYDYWGQGTLVTVSS
hHC05   YDYGDAYDYWGQGTLVTVSS
hHC06   YDYGDAYDYWGQGTLVTVSS
hHC07   YDYGDAYDYWGQGTLVTVSS
```

X: Variable amino acid according to humanized sequences
HCg: General heavy chain variable sequence
HCm: mouse heavy chain variable sequence
HCpH: partially humanized heavy chain variable sequence

Fig. 14

LC

```
            1         10        20        30        40        50
LCg     XIVMTQSXXXXXXSXGXXVSXXCKASQSVXXXVXWXQQKPXQXPKXLIXX
LCm     DIVMTQSQRFMTTSVGDRVSVTCKASQSVDSNVAWYQQKPRQSPKALIFS
LCpH    DIVMTQSPATLSVSVGDEVTLTCKASQSVDSNVAWYQQKPGQAPKLLIYS
hLC01   EIVMTQSPATLSVSPGERATLSCKASQSVDSNVAWYQQKPGQAPRALIYS
hLC02   EIVMTQSPATLSVSPGERATLSCKASQSVXXNVAWYQQKPGQAPRALIYS
hLC03   EIVMTQSPATLSVSPGERATLSCKASQSVDXXVXWXQQKPGQAPRALIXX
hLC04   EIVMTQSPATLSVSPGERATLSCKASQSVESNVAWYQQKPGQAPRALIYS 51        60        70        80        90       100
LCg     XXXRXSGXPARFXGSXXGTXFTLTISXLQSEDXAXYXCXQXNNXPXTFGA
LCm     ASLRFSGVPARFTGSGSGTDFTLTISNLQSEDLAEYFCQQYNNYPLTFGA
LCpH    DDLRFSGVPARFSGSGSGTDFTLTISSLQSEDFAVYYCQQYNNYPLTFGA
hLC01   ASLRFSGIPARFSGSGSGTEFTLTISSLQSEDFAVYYCQQYNNYPLTFGA
hLC02   ASLRFSGIPARFSGSGSGTEFTLTISSLQSEDFAVYYCQQYNNYPLTFGA
hLC03   AXXRXSGIPARFSGSXXGTEFTLTISSLQSEDFAVYYCXQXNNXPXTFGA
hLC04   ASLRFSGIPARFSGSGSGTEFTLTISSLQSEDFAVYYCQQYNNYPLTFGA

101
LCg     GTKLELKR
LCm     GTKLELKR
LCpH    GTKLELKR
hLC01   GTKLELKR
hLC02   GTKLELKR
hLC03   GTKLELKR
hLC04   GTKLELKR
```

X: Variable amino acid according to either mouse or humanized sequences
LCg: General heavy chain variable sequence
LCm: mouse heavy chain variable sequence
LCpH: partially humanized heavy chain variable sequence Fig. 16
A
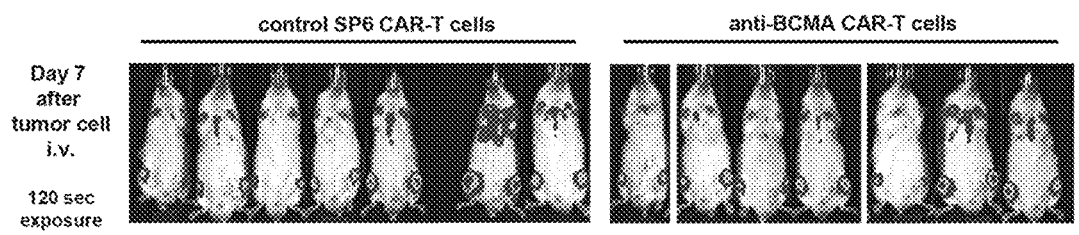
B
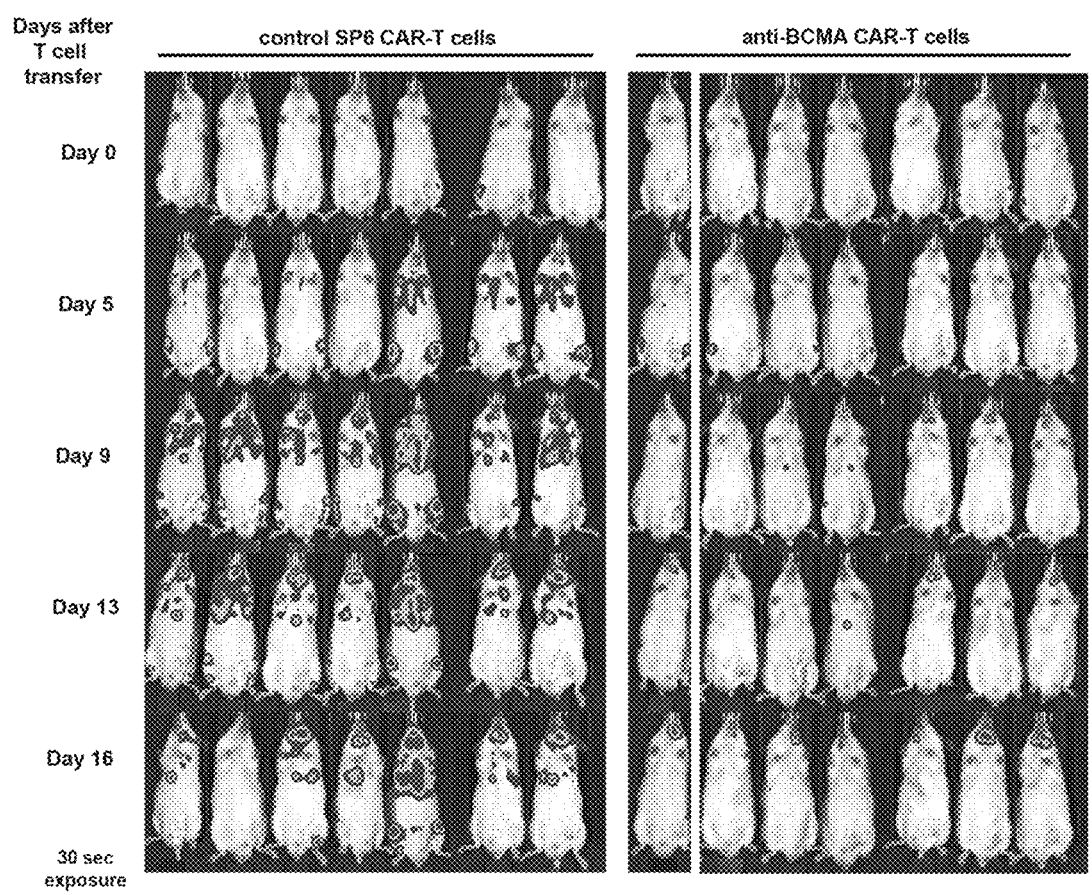
C
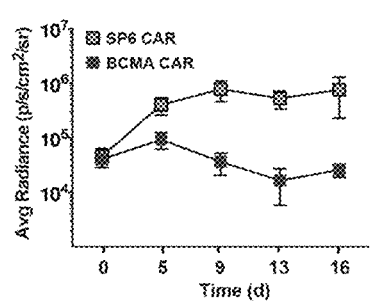

CHIMERIC ANTIGEN RECEPTOR AND CAR-T CELLS THAT BIND BCMA

The invention relates to an isolated chimeric antigen receptor polypeptide (CAR), wherein the CAR comprises an extracellular antigen-binding domain, comprising an antibody or antibody fragment that binds a B Cell Maturation Antigen (BCMA) polypeptide. The CAR preferably binds an epitope comprising one or more amino acids of residues 13 to 32 of the N-terminus of human BCMA. The invention further relates to a nucleic acid molecule encoding the CAR of the invention, a genetically modified immune cell, preferably a T cell, expressing the CAR of the invention and the use of said cell in the treatment of a medical disorder associated with the presence of pathogenic B cells, such as a disease of plasma cells, memory B cells and/or mature B cells, in particular multiple myeloma, non-Hodgkin's lymphoma or autoantibody-dependent autoimmune diseases.

REFERENCE TO SEQUENCE LISTING

A Sequence Listing submitted as an ASCII text file via EFS-Web is hereby incorporated by reference in accordance with 37 C.F.R. § 1.52(e). The name of the ASCII text file for the Sequence Listing is 55583943 1.TXT, the date of creation of the ASCII text file is May 11, 2022, and the size of the ASCII text file is 124 KB.

BACKGROUND OF THE INVENTION

In cancer immunotherapy, adoptive transfer of T cells (ATT) genetically modified to recognize tumor-specific or tumor-associated antigens is a promising approach in order to eradicate tumor and tumor stem cells. Thus, in contrast to traditional chemo-, radiation- and surgical therapies, tumor recurrence can be potentially avoided. Moreover, novel pathway-selective drugs often allow for excellent tumor control, but the disease course usually switches to a chronic phase without definite tumor elimination.

The advent of genetically modified T cells that express CARs has proven a tremendous success in B cell lymphoma/leukemia treatment, despite the fact that patients were heavily pre-treated and had previously received several lines of chemotherapies, antibody therapies or even autologous/allogeneic bone marrow transplantations. Thus, ATT with CAR-T cells was used successfully as salvage therapy.

CARs are synthetic, engineered immunoglobulin-derived receptors that can recognize surface antigens in an MHC-independent fashion. Unlike TCRs, CARs have a broader range of affinities that can engage the target antigen without necessarily exhibiting cross-reactivity. The target antigens must be surface-deposited and can include tumor-associated proteins, carbohydrates or even glycolipids. Another advantage of CAR-T cells is their rapid generation by transduction of autologous T cells, which can be either of CD4+ or CD8+ origin. CARs can be produced "off-the-shelf" and their targets are typically broadly expressed (>90%) in a defined tumor entity, as shown for CD19+ B-cell leukemias and lymphomas. It has been suggested that CAR T cells act as a "living drug" that could be maintained even after a single T cell infusion.

A strong medical demand exists for the chimeric antigen receptor (CAR)-T cell product described herein. Firstly, multiple myeloma is an incurable B cell non-Hodgkin lymphoma (B-NHL) which is derived from a malignantly transformed plasma cell clone. As a peculiarity, tumor cells localize predominantly to the bone marrow. This disease is the most frequent tumor of bone and bone marrow, has a 10-year survival rate of 50% among intensely treated younger patients, and is responsible for 2% of annual deaths from cancer. The incidence rate is 5/100.000, and the median age at diagnosis is 70 years, indicating that in many patients' co-morbidities exist that preclude intense and prolonged chemotherapies. The standard of care is chemotherapy, either alone or in combination with autologous stem cell transplantation, immunomodulatory drugs, local irradiation, proteasome inhibitors, and for very few patients allogeneic stem cell transplantation is applicable. Despite intense treatments with the aforementioned modalities, the disease usually relapses and after multiple lines of therapies, secondary resistance develops.

Secondly, the much larger group of classical B-NHL contain diverse entities of neoplasias derived from B lymphocytes that usually home to secondary lymphatic organs such as diffuse large B cell lymphoma (DLBCL), follicular lymphoma (FL), and a subgroup of chronic lymphocytic leukemia (CLL). While the total incidence rate of all NHL is about 10-12/100.000 (>85% of B cell origin), most of them are diseases of adults with a substantial increase in the elderly. The demographic development would predict that total numbers will increase due to aging of Western societies. Clinically, B-NHL are heterogeneous and can be distinguished by an aggressive and indolent course. Substantial progress has been made over the last 15 years in the treatment of B-NHL, the standard of care is combined antibody/chemotherapy, either alone or in combination with autologous stem cell transplantation, immunomodulatory drugs, irradiation, proteasome inhibitors, signaling pathway inhibitors, and for very few patients allogeneic stem cell transplantation applies. Because in many B-NHL entities median age at diagnosis is >55-60 years, co-morbidities also exist that preclude intense and extended chemotherapies or even allogeneic bone marrow transplantations.

The advent of adoptive CAR-T cell therapies targeted at the broadly expressed CD19 antigen on lymphoma B cells has made it possible to overcome these limitations and currently, about 20 CD19 CAR-T cell studies are registered at the FDA for the treatment of B-NHL and B-ALL. Although major breakthroughs were already achieved in clinical trials on CLL in 2011 and on B-ALL in 2013, to the best knowledge of the inventors permission to use identical CD19 CAR-products in Germany has been granted only very recently by biomedical companies. In other EU countries (e.g. Austria), clinical trials using CD19 CAR T-cells are also under way. More importantly, in anti-CD19 antibody or CAR-T cell therapies directed against B-NHL resistance occurs due to antigen loss. Because treatment resistance is observed after multiple lines of chemo-/immunotherapy, alternative target structures are urgently warranted.

For the indication multiple myeloma, two anti BCMA-CAR products have been described previously and have entered phase I clinical studies. These studies do not prove anti-BCMA CAR applicability to B-NHL. Regarding B-NHL, anti-BCMA targeted therapies represent possible alternatives, in particular when anti-CD19 CARs have failed. Other immunotherapy strategies targeted at multiple myeloma and tested in clinical studies are anti-CD19 CARs, NY-ESO1 and MAGE-A1-directed, TCR-transduced T cells. In stark contrast to BCMA as tumor target, frequencies of eligible patients are far lower because these target antigens are expressed in less than 10% of the cases. Other targeted therapies include anti-CD38 and anti-SLAMF7 antibodies, conceptually these therapies are completely different because antibodies are not self-sustained, do not form memory and to our knowledge, are not yet proven to mediate sufficient tumor eradication.

In addition, the ability to specifically target plasma cells would be of great benefit for the treatment of autoimmune diseases. Mild forms of autoimmune disease are usually initially treated with nonsteroidal anti-inflammatory drugs (NSAID) or disease-modifying anti-rheumatic drugs (DMARD). More severe forms of Systemic Lupus Erythematosus (SLE), involving organ dysfunction due to active disease, usually are treated with steroids in conjunction with strong immunosuppressive agents such as cyclophosphamide, a cytotoxic agent that targets cycling cells.

Only recently Belimumab, an antibody targeting the cytokine BAFF, which is found at elevated levels in serum of patients with autoimmune diseases, received approval by the Food and Drug Administration (FDA) for its use in SLE. However, only newly formed B cells rely on BAFF for survival in humans, whereas memory B cells and plasma cells are less susceptible to selective BAFF inhibition (Jacobi et al. (2010) Arthritis Rheum 62:201-210). For rheumatoid arthritis (RA), TNF inhibitors were the first licensed biological agents, followed by Abatacept, Rituximab, and Tocilizumab and others: they suppress key inflammatory pathways involved in joint inflammation and destruction, which, however, comes at the price of an elevated infection risk due to relative immunosuppression (Chan et al. (2010) Nat Rev Immunol 10:301-316, Keyser (2011) Curr Rheumatol Rev 7:77-87).

Only recently, CAR-T cells were also discussed as a targeted approach to treat autoantibody-mediated diseases (Ellebrecht et al. (2016) Science 353:179-184). Long-lived, sessile plasma cells residing in survival niches in the bone marrow are often resistant to conventional immunosuppressive and cytotoxic drugs as well as to therapies targeting B cells and their activation. In particular, Rituximab appears unsuitable for such a treatment, as its target antigen CD20 is not expressed on plasma cells. This therapeutic challenge could be met by employing anti-BCMA CAR-T cell constructs, as BCMA is expressed on long-lived plasma cells.

At present, a number of other anti-BCMA CAR constructs have been described in the art. In 2013, the group of James N. Kochenderfer published the first anti-BCMA CAR-transduced T cell approach, a pre-clinical study using in vitro assays and mouse testing (Carpenter et al., 2013; Clin Cancer Res; 19(8); 2048-2060). In June 2015, Bluebird Bio and Celgene announced their collaboration to focus on developing BCMA CAR-T cell therapies. Phase I clinical trial enrollment has started in January 2016 for multiple myeloma patients. In early 2016, Abramson Cancer Center of the University of Pennsylvania started participant recruitment for a Phase I study using anti-BCMA CAR-transduced T cells in the treatment of multiple myeloma patients (ClinicalTrials.gov Identifier: NCT02546167). CARs directed to BCMA have been described in WO 2016/014789, WO 2016/014565 and WO 2013/154760. WO 2015/128653 also discloses CAR sequences that bind BCMA, in which the portion of the CAR responsible for epitope recognition is a variant of the APRIL ligand, which shows improved binding to BCMA compared to wild-type APRIL. Alternative therapeutic strategies relate to an anti-CD38 CAR. BCMA-binding antibodies are disclosed in WO 2015/166073 and WO 2014/068079.

Although a number of potential alternative therapies are in development, a significant need remains for providing effective means for addressing medical disorders associated with the presence of pathogenic B cells, in particular multiple myeloma, non-Hodgkin's lymphoma or autoantibody-dependent autoimmune diseases.

SUMMARY OF THE INVENTION

In light of the prior art the technical problem underlying the invention was the provision of an agent suitable for treating diseases associated with pathogenic B cells.

This problem is solved by the features of the independent claims. Preferred embodiments of the present invention are provided by the dependent claims.

Therefore, the invention relates to an isolated chimeric antigen receptor polypeptide (CAR), wherein the CAR comprises:
  i. an extracellular antigen-binding domain, comprising an antibody or antibody fragment that binds a B Cell Maturation Antigen (BCMA) polypeptide,
  ii. a transmembrane domain, and
  iii. an intracellular domain,
and wherein said CAR binds an epitope comprising one or more amino acids of residues 13 to 32 of the N-terminus of BCMA.

The present invention therefore relates to a genetically modified immune cell, preferably a T cell, expressing the CAR of the invention and the use of said cell in the treatment of a medical disorder associated with the presence of pathogenic B cells.

The present invention therefore provides a preferably autologous T cell suitable for transplantation comprising an anti-BCMA CAR for the treatment of distinct stages of mature B-NHLs and multiple myeloma. In preferred embodiments of the immunotherapy approach of the present invention, patient-derived T cells are transduced, preferably retrovirally, to express an artificial immune receptor as described herein, composed of an extracellular antibody-derived antigen recognition part, fused to a transmembrane section, and followed by intracellular signaling domains. The construct described herein confers transduced T cells with anti-tumor cytolytic capacity.

As shown for other clinical CAR-T cell transfers, the present invention is characterized in that the anti-BCMA CAR-T cells based on the CAR described herein have predictable, tolerable and manageable side effects. Preclinical testing of the BCMA CAR-T cells described herein shows selectivity for the tumor-associated antigen BCMA. T cells equipped with the anti-BCMA CAR have a high affinity and avidity and recognize and destroy multiple myeloma cells while sparing normal hematopoietic cells. In a preferred embodiment, the transfer of autologous T cells prevents the possibility of graft-versus-host-disease. Memory CAR-T cell formation, which is important for the prevention of a relapse, can potentially develop.

Due to the high affinity and avidity of the anti-BCMA CAR-T cell described herein, even low BCMA-expressing mature B-NHLs can be recognized, allowing for T cell activation and tumor cell killing.

In preferred embodiments such mature B-NHL entities include certain stages of FL (follicular lymphoma), DLBCL (diffuse large B cell lymphoma), mantle cell lymphoma (MCL), and CLL (chronic lymphocytic leukemia).

The antigen recognition part of the CAR described herein is preferably based upon a humanized antibody described in WO/2015/166073. The antibody described therein was used to construct a number of CAR constructs that retain the high affinity and specificity for BCMA. The high affinity and specificity enable a reduction in off-target reactivity, providing an advantage over other BCMA CAR constructs. It was a surprising result that the high specificity and affinity of the original antibody could be maintained in the CAR as described herein to target B cells expressing even very low amounts of BCMA antigen.

The CAR of the present invention preferably binds an epitope comprising one or more amino acids of residues 13 to 32 of the N-terminus of BCMA. In other embodiments, binding to other epitopes of BCMA, in particular the N-terminus of BCMA is also possible.

The present invention also encompasses various signaling domains. The exchange of signaling domains meets the demands for either a strong and rapid effector phase (CD28 co-stimulatory domain), or a long-lasting relapse control as secured by a T cell memory population (4-1BB signaling domain). As demonstrated herein, the various signaling domains may be exchanged in multiple configuration, providing a CAR with flexibility with respect to its design without loss of the advantageous binding properties.

The anti-BCMA CAR-T cell product described herein is characterised by unique properties. Due to the low nanomolar affinity of the extracellular domain of the CAR-T cell construct, the anti-BCMA CAR as described herein has an unrivaled high affinity and confers extremely high specificity and avidity to T cells. These properties enable CAR-T cells to i) recognize, ii) be activated against, and iii) kill tumor target cells with high and, surprisingly, low BCMA surface expression.

The number of BCMA antigens expressed on the surfaces of tumor cells can be quantified by using an anti-BCMA antibody coupled to a fluorescent-dye in conjunction with Quantibrite beads (from Becton Dicksinson). The preferred method applied to quantify BCMA antigens expressed on the surfaces of tumor cells is "fluorescence activated cell sorting/cell analysis" (FACS). Fluorescence intensity of beads correlates exactly with the numbers of fluorescent antibodies bound to cells, and this is a measure for the number of BCMA molecules on cells. Myeloma cell-associated fluorescence densities are typically at least 2-3 $\log_{10}$-fold higher compared to low fluorescent B-NHL cells, showing that BCMA antigen densities can also vary over a range of at least 2-3 $\log_{10}$-fold.

None of the competing anti-BCMA CARs has proven reactivity against B-NHL other than multiple myeloma cells or in very rare cases, Burkitt-lymphoma. Therefore, the anti-BCMA CAR exhibits reactivity against an unprecedented diversity of B-NHLs. These properties represent unexpected and surprising benefits with respect to CAR-T therapy. Typical expectations of a skilled person require a high number of target antigens to be expressed, in order to enable CAR-T targeting. The CAR-Ts employing the CARs of the invention show unprecedented activity against B cells with low expression levels of target antigen.

In preferred embodiments, in combination with the MP71-vector and a gamma-retrovirus expression system, an unusually high transduction rate for human T cells can be achieved.

Preferred Embodiments Regarding the BCMA Epitope Bound by the CAR

The CAR of the present invention is directed preferably towards an epitope comprising one or more amino acids of residues 13 to 32 of the N-terminus of human BCMA. The amino acid sequence of residues 13 to 32 of CD269 are shown in SEQ ID No. 33. The N-terminus sequence of CD269 is provided in SEQ ID No. 32. The extracellular domain of CD269 is provided as SEQ ID No. 31.

An antigen comprising the extracellular domain of CD269 according to SEQ ID No. 31 was used in vaccination in order to generate the binding specificity of the mouse and chimeric antibody described herein and previously (WO/2014/068079) that has been modified for use in the CAR format in the present invention. Use of the entire CD269 protein, or fragments thereof comprising either a membrane-bound or intracellular domain, as an antigen during antibody generation could produce antibodies that bind concealed or intracellular domains of CD269, thereby rendering such agents unsuitable or disadvantageous for therapeutic application. The CAR of the present invention is therefore defined by its binding to the extracellular portion of CD269. The specific epitope within the extracellular domain also represents a preferred novel and unexpected characterising feature of the invention.

Fab fragments prepared from mouse or chimeric antibodies from the present CAR was derived were crystallized in complex with the purified BCMA extracellular domain and the complex structure solved. The structural analysis has revealed detailed information of the epitope of the binding region of the antibody/CAR of the present invention and its biological relevance. The binding of an epitope comprising one or more amino acids of residues 13 to 32 of BCMA of the extracellular domain by the antibody of the present invention is an advantageous property due to its high binding specificity and extracellular location. To the knowledge of the inventor, no CAR has been previously described that binds this region.

In one embodiment the CAR of the present invention is characterised in that the CAR binds an epitope comprising one or more of amino acids 13, 15, 16, 17, 18, 19, 20, 22, 23, 26, 27 or 32 of CD269 (BCMA). In another embodiment the CAR of the present invention is characterised in that the antibody binds an epitope consisting of amino acids 13, 15, 16, 17, 18, 19, 20, 22, 23, 26, 27 and 32 of CD269 (BCMA). These residues represent the amino acids that interact directly with the antibody of the present invention, as identified by the crystal structure data provided herein. The numbering of these residues has been carried out with respect to SEQ ID No. 32, which provides the N-terminal sequence of human BCMA.

As disclosed previously, the affinity of the antibodies from which the CAR of the present invention was derived is surprisingly high and comparatively better than similar approaches attempted in the prior art. The CAR of the present invention is therefore defined by a high affinity not seen in other anti-BCMA CAR molecules. A Kd in the pM range (as shown below) is commonly accepted as an outstanding affinity not to be expected in common practice.

In another aspect, the humanized antibody or antibody fragment, from which the CAR of the invention is derived, binds BCMA with high affinity, for example when measured by surface plasmon resonance, such as Biacore, the antibody binds to human BCMA with an affinity of 100 nM, 90, 80, 70, 60, 50, 40, 30 nM or less, or 20 nM or less, or an affinity of 15 nM or less, or an affinity of 5 nM or less, or an affinity of 1000 pM or less, or an affinity of 500 pM or less, or an affinity of 100 pM or less, or 80 pM or less, or for example about 50 pM. The CAR of the present invention therefore exhibits corresponding affinities.

In a further embodiment the antibody, from which the CAR of the invention was derived, binds to human CD269 when measured by surface plasmon resonance, such as Biacore, of between about 1 pM and about 100 nM, or between about 100 pM and about 50 nM, or between about 200 pM and about 20 nM. The CAR of the present invention therefore exhibits corresponding affinities.

In one embodiment the CAR and/or CAR-T of the present invention is characterised in that the CAR binds cells that express BCMA, wherein said BCMA is detectable on the cell surface, and wherein BCMA is present on the cell surface in 1-4 $\log_{10}$-fold, preferably 2-3 $\log_{10}$-fold, lower amounts compared to multiple myeloma cells, preferably compared to those multiple myeloma cell lines used in the examples demonstrated herein. Examples of such cells, without being limited thereto, are non-Hodgkin's lymphoma (B-NHL) cells, such as DOHH-2, SU-DHL4, JEKO-1, JVM-3 and/or MEC-1 cell lines.

Preferred Embodiments Regarding the CAR Sequences:

In one embodiment the isolated chimeric antigen receptor polypeptide (CAR) of the invention is characterised in that the antigen-binding domain comprises a variable heavy chain (VH), said VH comprising:
  a heavy chain complementary determining region 1 (H-CDR1) with at least 80% sequence identity to SEQ ID NO 1 (GFTFSRYW),
  a heavy chain complementary determining region 2 (H-CDR2) with at least 80% sequence identity to SEQ ID NO 2 (INPSSSTI), and
  a heavy chain complementary determining region 3 (H-CDR3) with at least 80% sequence identity to SEQ ID NO 3 (ASLYYDYGDAYDY),
  and a variable light chain (VL), said VL comprising:
  a light chain complementary determining region 1 (L-CDR1) with at least 80% sequence identity to SEQ ID NO 4 (QSVESN),
  a light chain complementary determining region 2 (L-CDR2) with at least 80% sequence identity to SEQ ID NO 5 (SAS), and
  a light chain complementary determining region 3 (L-CDR3) with at least 80% sequence identity to SEQ ID NO 6 (QQYNNYPLT).

In one embodiment the isolated chimeric antigen receptor polypeptide (CAR) of the invention is characterised in that the antigen-binding domain comprises a variable heavy chain (VH), said VH comprising:
  a heavy chain complementary determining region 1 (H-CDR1) with at least 80% sequence identity to SEQ ID NO 25 (RYWFS),
  a heavy chain complementary determining region 2 (H-CDR2) with at least 80% sequence identity to SEQ ID NO 26 (EINPSSSTINYAPSLKDK), and
  a heavy chain complementary determining region 3 (H-CDR3) with at least 80% sequence identity to SEQ ID NO 27 (SLYYDYGDAYDYW),
  and a variable light chain (VL), said VL comprising:
  a light chain complementary determining region 1 (L-CDR1) with at least 80% sequence identity to SEQ ID NO 28 (KASQSVESNVA),
  a light chain complementary determining region 2 (L-CDR2) with at least 80% sequence identity to SEQ ID NO 29 (SASLRFS), and
  a light chain complementary determining region 3 (L-CDR3) with at least 80% sequence identity to SEQ ID NO 30 (QQYNNYPLTFG).

The CDR sequences recited above under SEQ ID NO 25-30 represent embodiments obtained using alternative parameters for defining the CDR regions, and encompassing for example additional flanking amino acids in comparison to SEQ ID NO 1-6.

The CDR sequences of SEQ ID NO 1-6 and 25-30 may also be defined such that a polypeptide sequence is encompassed by the invention with at least 70%, 75%, 80%, 85%, 90%, or at least 95% sequence identity to the specific sequences listed.

In one embodiment the isolated chimeric antigen receptor polypeptide (CAR) of the invention is characterised in that said CAR comprises a VH domain that comprises CDR sequences of:
  GFTFSRYW (H-CDR1; SEQ ID NO. 1);
  INPX$_2$X$_3$STI (H-CDR2; SEQ ID No. 7), wherein X$_2$X$_3$: SS, NS, TS, GS, KS, RS, SD, SN, DE; and
  ASLYX$_4$DYGDAX$_5$DY (H-CDR3; SEQ ID NO. 8), wherein X$_4$: Y, L, A, V, F, I, W, and/or X$_5$: Y, L, F, I, V, A, C,
  and a VL domain that comprises CDR sequences of:
  QSVX$_1$X$_2$N (L-CDR1; SEQ ID NO. 9), wherein X$_1$X$_2$: ES, SS, TS, QS, HS, DH;
  SAS (L-CDR2; SEQ ID NO 5); and
  QQYNNYPLTFG (L-CDR3; SEQ ID NO. 10).

In alternative embodiments the isolated chimeric antigen receptor polypeptide (CAR) of the invention comprises a VH domain that comprises CDR sequences of:
  RYWX$_1$S (H-CDR1; SEQ ID NO. 34), wherein X$_1$: I, F, L, V, Y. C, G, A, S, T);
  EINPX$_2$X$_3$STINYAPSLKDK (H-CDR2; SEQ ID No. 35), wherein X$_2$X$_3$: SS, NS, TS, GS, KS, RS, SD, SN, DE; and
  SLYX$_4$DYGDAX$_5$DYW (H-CDR3; SEQ ID NO. 36), wherein X$_4$: Y, L, A, V, F, I, W, and/or X$_5$: Y, L, F, I, V, A, C,
  and a VL domain that comprises CDR sequences of:
  KASQSVX$_1$X$_2$NVA (L-CDR1; SEQ ID NO. 37), wherein X$_1$X$_2$: ES, SS, TS, QS, HS, DH;
  SASLRFS (L-CDR2; SEQ ID NO 29); and
  QQYNNYPLTFG (L-CDR3; SEQ ID NO. 30).

The CDR sequences recited above under SEQ ID NO 34-37 represent embodiments obtained using alternative parameters for defining the CDR regions, and for example encompassing additional flanking amino acids in comparison to SEQ ID NO 1-6.

In one embodiment the isolated chimeric antigen receptor polypeptide (CAR) of the invention is characterised in that said CAR comprises the following sequences:

```
                                     (SEQ ID NO. 1)
H-CDR1: GFTFSRYW, (SEQ ID NO. 2)
H-CDR2: INPSSSTI, (SEQ ID NO. 3)
H-CDR3: ASLYYDYGDAYDY, (SEQ ID NO. 4)
L-CDR1: QSVESN, (SEQ ID NO. 5)
L-CDR2: SAS,
and (SEQ ID NO. 6)
L-CDR3: QQYNNYPLT.
```

In one embodiment the isolated chimeric antigen receptor polypeptide (CAR) of the invention comprises CDR sequences of:

```
                                    (SEQ ID NO. 25)
    H-CDR1: RYWFS, (SEQ ID NO. 26)
    H-CDR2: EINPSSSTINYAPSLKDK, (SEQ ID NO. 27)
    H-CDR3: SLYYDYGDAYDYW, (SEQ ID NO. 28)
    L-CDR1: KASQSVESNVA, (SEQ ID NO. 29)
    L-CDR2: SASLRFS,
    and (SEQ ID NO. 30)
    L-CDR3: QQYNNYPLTFG,
```

In one embodiment the isolated chimeric antigen receptor polypeptide (CAR) of the invention is characterised in that said CAR comprises a VH domain with at least 80% sequence identity to SEQ ID NO 11

(EVQLVESGGGLVQPGGSLRLSCAASGFTFSRYWFSWVRQAPGKGLVWVG

EINPSSSTINYAPSLKDKFTISRDNAKNTLYLQMNSLRAEDTAVYYCASL

YYDYGDAYDYWGQGTLVTVSS);

and a VL domain with at least 80% sequence identity to SEQ ID NO 12

(EIVMTQSPATLSVSPGERATLSCKASQSVESNVAWYQQKPGQAPRALIY

SASLRFSGIPARFSGSGSGTEFTLTISSLQSEDFAVYYCQQYNNYPLTFG

AGTKLELK).

SEQ ID NO 11 and 12 represent the "full length" VH and VL domains of the preferred CAR. Sequences with at least 70%, preferably 80%, 85%, 90% or at least 95% sequence identity to SEQ ID NO 11 and 12, in particular when such sequence variants exhibit the desired BCMA binding specificity (functionally analogous/equivalent), are encompassed by the scope of the present invention.

In one embodiment the isolated chimeric antigen receptor (CAR) polypeptide comprising the VH and VL sequences of SEQ ID NO 11 and 12, or sequences with at least 80% identity to SEQ ID NO 11 and 12, comprises at least W36, E50, L99, Y100, Y101 and A106 of SEQ ID NO 11, and at least S31, A34, S50, L53, Q89, Y91, Y94 and L96 of SEQ ID NO 12.

The amino acid residues listed above represent those that are known to interact directly with the target BCMA epitope. The invention is therefore related to CARs in which sequence variation in the VH and VL, within at least 70%, preferably 80%, 85%, 90% or at least 95% sequence identity to SEQ ID NO 11 and 12, occurs, but the VH and VL domains comprise at least those residues known to interact with the target epitope.

In one embodiment the isolated chimeric antigen receptor (CAR) polypeptide comprising the VH and VL sequences of SEQ ID NO 11 and 12, or sequences with at least 80% identity to SEQ ID NO 11 and 12, comprises at least the CDR sequences of SEQ ID NO 1, 7, 8, 9, 5 and 10, as described herein, preferably the CDR sequences of SEQ NO 1 to 6.

The invention is therefore related to CARs in which sequence variation in the VH and VL, within at least 70%, preferably 80%, 85%, 90% or at least 95% sequence identity to SEQ ID NO 11 and 12, occurs, but the VH and VL domains comprise at least the CDR sequences as described herein. The CDRs may represent any sequence named as a CDR herein, in particular those of SEQ ID NO 1-6 or SEQ ID NO 25-30.

In a preferred embodiment the isolated chimeric antigen receptor polypeptide (CAR) of the present invention is characterised in that when said CAR is expressed in a genetically modified immune cell, preferably a T lymphocyte, said immune cell binds BCMA on the surface of a non-Hodgkin's lymphoma (B-NHL) via said CAR and is activated, thereby inducing cytotoxic activity against said B-NHL.

In a preferred embodiment the isolated chimeric antigen receptor polypeptide (CAR) of the present invention is characterised in that the B cell lymphoma is a non-Hodgkin's lymphoma (B-NHL) cell, such as DOHH-2, SU-DHL4, JEKO-1, JVM-3 and/or MEC-1 cell lines.

The CAR of the present invention is characterised by the surprising property that even very low levels of BCMA on the surface of a cell may lead to CAR binding, T cell activation and cytotoxicity against the bound cell. This represents a significant advantage compared to CARs as commonly described. Typically, a CAR requires a large number of surface antigens in order to enable activation of the CAR and subsequent cytotoxic activity. The CAR of the present invention is therefore associated with unexpected benefits in light of CARs known in the art.

The derivatization of the mouse, chimeric and/or human antibody described previously, in order to generate the CAR as described herein, may in some embodiments provide this advantage. In some embodiments the features of the BCMA epitope preferably lead to this advantage. In other embodiments the high affinity and specificity of the VH and VL fragments described herein enable the sensitivity of the present CAR. It was however unexpected that this property would arise in combination with a CAR from the earlier description of the antibodies. It was entirely surprising that the particular sequences provided herein, preferably the CDR regions of the VL and VH regions involved in binding, exhibit the specific and strong binding sufficient to enable activation of a CAR-T cell against cells with minimal BCMA expression.

It was unexpected that the VH and VL fragments described herein could be arranged in multiple configurations in the CAR as described herein and still maintain high specificity and high affinity for the target epitope. As shown below and in FIG. 3, the CAR may be configured in the VH-VL or VL-VH configuration, with variation in the linker, hinge, transmembrane domain, co-stimulatory domain and/or activation domains, and still maintain its efficacy. This surprising feature of the invention enables greater flexibility in the design of CARs directed against BCMA, thereby enabling further modification and/or optimization of the CAR structure on the basis of the VH and VL domains described herein, if any further development should be necessary or desired.

In a preferred embodiment the isolated chimeric antigen receptor polypeptide (CAR) of the present invention is characterised in that when said CAR is expressed in a genetically modified immune cell, preferably a T lymphocyte, said immune cell binds BCMA on the surface of a multiple myeloma cell (MM) via said CAR and is activated, thereby inducing cytotoxic activity against said MM cell.

Preferred MM cells are those disclosed herein. In a preferred embodiment the CAR as described herein shows effective binding and cytotoxic activity against both MM and B-NHL. In light of the prior art it would not have been expected by a skilled person that the CARs described herein would be capable of exhibiting activity against both of these cell types.

Preferred Embodiments Regarding Humanized VH and VL Domains

As disclosed in detail herein and previously (WO/2015/166073), the sequence of the antibody J22.9-xi was humanized in order to provide a more compatible reagent for administration in human subjects. Various humanized sequence variants of J22.9-xi have been generated and tested for their binding affinity and specificity to both human and cynomolgus BCMA. In preferred embodiments the CAR of the present invention incorporates these humanized sequences. The results from binding assays conducted with the corresponding antibodies demonstrate that the humanized sequences maintain the desired binding properties of the chimeric reagent J22.9-xi. In the below sequences the underlined regions represent the CDRs or putative CDRs, depending on the method used for CDR determination.

Preferred Embodiments Regarding Humanized VH Variants

Additional information is provided below on the humanized VH and VL sequences preferably incorporate by the CAR of the present invention.

Chimeric Sequence:

```
HC mouse (SEQ ID No. 38):
                                               (SEQ ID No. 38)
QVQLQQSGGGLVQPGGSLKLSCAASGIDFSRYWMSWVRRAPGKGLEWIGE

INPDSSTINYAPSLKDKFIISRDNAKNTLYLQMSKVRSEDTALYYCASLY

YDYGDAMDYWGQGTSVTVSS
```

The HC mouse sequence represents the variable region of the heavy chain (VH) originally developed for the chimeric antibody J22.9-xi, which comprises VL and VH domains obtained from a mouse antibody, capable of binding an epitope of the extracellular domain of CD269 (BCMA), and the VL and VH domains are fused to human CL and CH domains, respectively. In some embodiments the CAR may incorporate the HC mouse sequence or CDRs thereof.

Partially Humanized Sequences:

```
HC partially humanized (SEQ ID No. 39):
EVQLVESGGGLVQPGGSLRLSCAASGFTFDDYWMSWVRQAPGKGLEWVGE

INPDSSTINYAPSLKGRFTISRDNAKNTLYLQMNSLRAEDTAVYYCASLY

YDYGDAMDYWGQGTLVTVSS
```

The HC partially humanized sequence represents a modified amino acid sequence (via amino acid substitutions) in comparison to the chimeric antibody disclosed herein, whereby the VL and VH binding regions have been modified with respect to their sequence to make them more suitable for administration in humans.

Humanized VH Sequence:

```
hHC01
                                               (SEQ ID No. 40)
EVQLVESGGGLVQPGGSLRLSCAASGFTFSRYWMSWVRQAPGKGLWVVGE

INPDSSTINYAPSLKDKFTISRDNAKNTLYLQMNSLRAEDTAVYYCASLY

YDYGDAMDYWGQGTLVTVSS
```

Humanized VH Sequence with Removal of Post Translational Modification Motifs:

```
hHC02
                                               (SEQ ID No. 41)
EVQLVESGGGLVQPGGSLRLSCAASGFTFSRYWX₁SWVRQAPGKGLVWVG

EINPX₂X₃STINYAPSLKDKFTISRDNAKNTLYLQMNSLRAEDTAVYYCA

SLYX₄DYGDAX₅DYWGQGTLVTVSS
```

Wherein:

$X_1$: I, F, L, V, Y. C, G, A, S, T, preferably I or F;

$X_2X_3$: SS, NS, TS, GS, KS, RS, SD, SN, DE, preferably SS;

$X_4$: Y, L, A, V, F, I, W, preferably Y; and/or $X_5$: Y, L, F, I, V, A, C, preferably Y;

The "hHC01" and "hHC02" humanized sequences represent preferred amino acid sequences for the present CAR that comprise sequence changes in comparison to both the original chimeric sequence and the partially humanized sequences described herein.

The PTM mutations are intended to remove potentially detrimental post translational modification motifs from said proteins, whilst maintaining the advantageous binding properties. The positions 1, 5, 6, 19, 27, 28, 34, 39, 46, 48, 54, 69, 84, 85, 86, 88, 93, 107 and/or 115 of hHC01 and hHC02 are preferably mutated (substituted) in comparison to the original chimeric sequence. The importance of the substitution relates primarily to the resulting amino acid, not the originating amino acid. The change may therefore also be carried out from the corresponding amino acid of the original chimeric amino acid or other variant, such as the partially humanized sequences.

The following substitutions are preferred in some embodiments, and differ in comparison to the chimeric (SEQ ID No 38) sequence:

the amino acid M34 of the HC (VH) sequence is substituted with any amino acid, preferably I, L, F, V, Y. C, G, A, S, T;

the amino acid E46 of the HC (VH) sequence is substituted with V;

the amino acids D54 and S55 of the HC (VH) sequence is substituted with any amino acid combination, preferably SS, TS, GS, KS, RS, SD, SN, DE;

the amino acid Y101 of the HC (VH) sequence is substituted with any amino acid, preferably L, A, V, F, I, W; and/or the amino acid M107 of the HC (VH) sequence is substituted with any amino acid, preferably L, Y, F, I, V, A, C.

Sequences that May be Modified at Those Residues Required for Direct Interaction with BCMA:

```
hHC03 - modified amino acids involved in
interaction with BCMA (SEQ ID No 42):
```
EVQLVESGGGLVQPGGSLRLSCAASGFTFSRY$X_1$M$X_2$WVRQAPGKGLV$X_3$

VG$X_4$INPDSSTINYAPSLKDKFTISRDNAKNTLYLQMNSLRAEDTAVYYC

AS$X_5X_6X_7$DYGD$X_8$MDYWGQGTLVTVSS

Wherein preferred amino acids are:
$X_1$: W, F, Y, preferred W;
$X_2$: S, T, N, Q, D, E, preferred S;
$X_3$: W, F, Y, preferred W;
$X_4$: E, Q, preferred E;
$X_5$: L, I, V, G, A, preferred L;
$X_6$: Y, X, preferred Y;
$X_7$: Y, F, L, I, V, M, preferred Y; and/or
$X_8$: A, G, V, preferred A.

The "hHC03" humanized sequence represents preferred amino acid sequences that comprise amino acid sequence changes in comparison to both the original chimeric sequence and the partially humanized sequence. These sequence changes are intended to reflect potential changes in the amino acids that bind the BCMA target, which may be substituted, whilst maintaining the advantageous binding properties. The importance of the substitution relates primarily to the resulting amino acid, not the originating amino acid. The change may therefore also be carried out from the corresponding amino acid of the original chimeric amino acid or other variant.

For example:
- the amino acid W33 of the HC (VH) sequence is W, F, Y;
- the amino acid S35 of the HC (VH) sequence is S, T, N, Q, D, E;
- the amino acid W47 of the HC (VH) sequence is W, F, Y;
- the amino acid E50 of the HC (VH) sequence is E, Q;
- the amino acid L99 of the HC (VH) sequence is L, I, V, G, A;
- the amino acid Y100 of the HC (VH) sequence is Y, X;
- the amino acid Y101 of the HC (VH) sequence is Y, F, L, I, V, M; and/or
- the amino acid A106 of the HC (VH) sequence is A, G, V.

In general, any change to a CDR region made during humanization may also be considered as a feature of a CDR sequence when considered independently of the framework sequence as a whole. Such modified CDR sequences may be considered defining features of the present invention, either within or independent of their context in the entire framework region described herein. For example, the CDR sequences identified by underline in the hHC01 to hHC03 may be considered a defining feature of the invention independently of the surrounding variable region sequence.

Specific Examples of Humanized HC (VH) Sequences:

```
hHC04 (SEQ ID NO 43):
EVQLVESGGGLVQPGGSLRLSCAASGFTFSRYWISWVRQAPGKGLVWVGE

INPNSSTINYAPSLKDKFTISRDNAKNTLYLQMNSLRAEDTAVYYCASLY

YDYGDAYDYWGQGTLVTVSS hHC05 (SEQ ID NO 44):
EVQLVESGGGLVQPGGSLRLSCAASGFTFSRYWFSWVRQAPGKGLVWVGE

INPNSSTINYAPSLKDKFTISRDNAKNTLYLQMNSLRAEDTAVYYCASLY

YDYGDAYDYWGQGTLVTVSS
```

-continued

```
hHC06 (SEQ ID NO 45):
EVQLVESGGGLVQPGGSLRLSCAASGFTFSRYWISWVRQAPGKGLVWVGE

INPSSSTINYAPSLKDKFTISRDNAKNTLYLQMNSLRAEDTAVYYCASLY

YDYGDAYDYWGQGTLVTVSS hHC07 (SEQ ID NO 46):
EVQLVESGGGLVQPGGSLRLSCAASGFTFSRYWFSWVRQAPGKGLVWVGE

INPSSSTINYAPSLKDKFTISRDNAKNTLYLQMNSLRAEDTAVYYCASLY

YDYGDAYDYWGQGTLVTVSS
```

In order to remove a potential post-translational modification site in the humanized J22.9, residue D54 of the heavy chain CDR2 was mutated to asparagine (N), creating a new potential modification site for N-linked glycosylation (e. g. hHC04, 05). The mutated heavy chain containing N54 can be glycosylated. The corresponding IgG, J22.9-FNY, nevertheless bound BCMA in FACS and ELISA, and was crystallized in complex with BCMA. It is surprising that such a large extension of the side chain would not disrupt binding to BCMA and it could be expected from these observations that multiple and various amino acid substitutions would be tolerated at this position, potentially also derivatizations other than sugars.

Alignments:

A CLUSTAL W (1.83) multiple sequence alignment of the various substituted positions within the HC sequence provides appropriate sequence comparisons in FIG. 13. The "General sequence" represents an HC sequence, whereby each X represents a potential amino acid change to any given amino acid. Preferred amino acid substitutions are those described above for each of the potentially mutated positions.

Preferred Embodiments Regarding Humanized VL Variants

Chimeric Sequence:

```
LC mouse (SEQ ID No. 47):
DIVMTQSQRFMTTSVGDRVSVTCKASQSVDSNVAWYQQKPRQSPKALIF

SASLRFSGVPARFTGSGSGTDFTLTISNLQSEDLAEYFCQQYNNYPLTF

GAGTKLELKR
```

The LC mouse sequence represents the variable region of the light chain (VL) originally developed for the chimeric antibody J22.9-xi, which comprises VL and VH domains obtained from a mouse antibody, capable of binding an epitope of the extracellular domain of CD269 (BCMA). In some embodiments the mouse VL domain or CDRs thereof may be employed in the CAR of the present invention.

Partially Humanized Sequences:

```
LC partially humanized (SEQ ID NO 48):
DIVMTQSPATLSVSVGDEVTLTCKASQSVDSNVAWYQQKPGQAPKLLIY

SDDLRFSGVPARFSGSGSGTDFTLTISSLQSEDFAVYYCQQYNNYPLTF

GAGTKLELKR
```

The LC partially humanized sequence represents a modified sequence (via amino acid substitutions) in comparison to the chimeric antibody, whereby the VL and VH binding regions have been modified with respect to their sequence to make them more suitable for administration in humans.

Humanized VL Sequence:

```
hLC01 (SEQ ID NO 49):
EIVMTQSPATLSVSPGERATLSCKASQSVDSNVAWYQQKPGQAPRALIYS

ASLRFSGIPARFSGSGSGTEFTLTISSLQSEDFAVYYCQQYNNYPLTFGA

GTKLELKR
```

Humanized VL Sequence with Removal of Post Translational Modification Motifs:

```
hLC02 (SEQ ID NO 50):
EIVMTQSPATLSVSPGERATLSCKASQSVX₁X₂NVAWYQQKPGQAPRALI

YSASLRFSGIPARFSGSGSGTEFTLTISSLQSEDFAVYYCQQYNNYPLTF

GAGTKLELKR
```

Wherein:

$X_1X_2$: ES, SS, TS, QS, HS, DH, preferably ES.

The "hLC01" and "hLC02" humanized sequences represent preferred amino acid sequences that comprise amino acid sequence changes in comparison to both the original chimeric sequence and the partially humanized sequences described herein.

The PTM mutations are intended to remove potentially detrimental post translational modification motifs from said proteins, whilst maintaining the advantageous binding properties. The positions 1, 8, 9, 10, 13, 15, 17, 19, 20, 21, 22, 30, 41, 43, 45, 49, 58, 63, 70, 77, 83, 85 and/or 87 of hLC01 and hLC02 are preferably mutated (substituted) in comparison to the original chimeric sequence.) The importance of the substitution relates primarily to the resulting amino acid, not the originating amino acid. The change may therefore also be carried out from the corresponding amino acid of the original chimeric amino acid or other variant.

The following substitutions are preferred and differ from the chimeric and partially humanized sequences:
- the amino acid D1 of the LC (VL) sequence is substituted with E;
- the amino acid V15 of the LC (VL) sequence is substituted with P;
- the amino acid D17 of the LC (VL) sequence is substituted with E;
- the amino acid V19 of the LC (VL) sequence is substituted with A;
- the amino acid T22 of the LC (VL) sequence is substituted with S;
- the amino acids D30 and S31 of the LC (VL) sequence is substituted with any amino acid combination, preferably ES, SS, TS, QS, HS, DH;
- the amino acid V58 of the LC (VL) sequence is substituted with I; and/or
- the amino acid D70 of the LC (VL) sequence is substituted with E.

Sequences that May be Modified in their CDR Binding Regions at Those Residues Required for Interaction with BCMA:

```
hLC03 - modified amino acids involved in
interaction with BCMA (SEQ ID NO 51):
EIVMTQSPATLSVSPGERATLSCKASQSVDX₁X₂VX₃WX₄QQKPGQAPRA

LIX₅X₆AX₇X₈RX₉SGIPARFSGSX₁₀X₁₁GTEFTLTISSLQSEDFAVYY

CX₁₂QX₁₃NNX₁₄PX₁₅TFGAGTKLELKR
```

Wherein preferred amino acids are:
$X_1$: S, H, T, N, D, Q;
$X_2$: N, E, Q;
$X_3$: A, G, V, S, T, L, I;
$X_4$: Y, F, L, I, V, A, G;
$X_5$: Y, F, L;
$X_6$: S, T;
$X_7$: S, T, D, N, H, E, Q;
$X_8$: L, V, I, M;
$X_9$: F, L, I, V, Y, M;
$X_{10}$: G, X;
$X_{11}$: S, X;
$X_{12}$: Q, V, L, I, M;
$X_{13}$: Y, F, L, I, Q;
$X_{14}$: Y, F, R, Q, K; and/or
$X_{15}$: L, I, V, F.

The "hLC03 humanized sequence" represents preferred amino acid sequences that comprise amino acid sequence changes in comparison to both the original chimeric sequence and the partially humanized sequence. These sequence changes are intended to reflect potential changes in the amino acids that bind the BCMA target, which may be substituted, whilst maintaining the advantageous binding properties. The importance of the substitution relates primarily to the resulting amino acid, not the originating amino acid. The change may therefore also be carried out from the corresponding amino acid of the original chimeric amino acid or other variant.

For example:
- the amino acid S31 of the LC (VL) sequence is S, H, T, N, D, Q;
- the amino acid N32 of the LC (VL) sequence is N, E, Q;
- the amino acid A34 of the LC (VL) sequence is A, G, V, S, T, L, I;
- the amino acid Y36 of the LC (VL) sequence is Y, F, L, I, V, A, G;
- the amino acid Y49 of the LC (VL) sequence is Y, F, L;
- the amino acid S50 of the LC (VL) sequence is S, T;
- the amino acid S52 of the LC (VL) sequence is S, T, D, N, H, E, Q;
- the amino acid L53 of the LC (VL) sequence is L, V, I, M;
- the amino acid F55 of the LC (VL) sequence is F, L, I, V, Y, M;
- the amino acid G66 of the LC (VL) sequence is G, X;
- the amino acid S67 of the LC (VL) sequence is S, X;
- the amino acid Q89 of the LC (VL) sequence is Q, V, L, I, M;
- the amino acid Y91 of the LC (VL) sequence is Y, F, L, I, Q;
- the amino acid Y94 of the LC (VL) sequence is Y, F, R, Q, K; and/or
- the amino acid L96 of the LC (VL) sequence is L, I, V, F.

In general, any change to a CDR region may also be considered as a feature of a CDR sequence when considered independently of the framework sequence as a whole. Such modified CDR sequences may be considered defining features of the sequences employed herein, either within or independent of their context in the entire framework region described herein. For example, the CDR sequences identified by underline in the hLC01 to hLC03 may—in their unmodified or substituted form—be considered a defining feature of the invention independently of the surrounding variable sequences.

Example of Humanized LC Sequence:

hLC04 (SEQ ID NO 52):
EIVMTQSPATLSVSPGERATLSC<u>KASQSVESNVA</u>WYQQKPGQAPRALIY<u>S
ASLRFS</u>GIPARFSGSGSGTEFTLTISSLQSEDFAVYYC<u>QQYNNYPLTFGA
GTKLELKR</u>

Alignments:

A CLUSTAL W (1.83) multiple sequence alignment of the various potentially amended sites within the LC sequence provides appropriate sequence comparisons in FIG. 14. The "General sequence" represents an LC sequence, whereby each X represents a potential amino acid change. Preferred amino acid substitutions are those described above for each of the potentially mutated positions.

The present invention therefore relates to the humanized sequences according to hHC01, hHC02, hHC03, hHC04, hHC05, hHC06, hHC07, hLC01, hLC02, hLC03 and/or hLC04, or any given combination thereof.

All possible combinations of potential modifications for any given potentially variant residue proposed herein (as identified by X in the "general" sequence) are encompassed by the present invention. By combining one or more of these various substitutions, humanized variants may be generated that exhibit the desired binding properties of the chimeric antibody originally developed and demonstrated herein. The antibodies or parts thereof described herein also encompass a sequence with at least 80%, preferably 90%, sequence identity to those humanized sequences disclosed explicitly or disclosed through a sequence formula.

The invention further relates to CAR as described herein comprising a VH domain, wherein said VH domain comprises a sequence according to $X_1$VQL$X_2X_3$SGGGLV QPGGSL$X_4$LSCAASG$X_5X_6$F$X_7X_8$YWZ$_1$SWVR$X_9$APG-KGLEW$X_{10}$GEINPZ$_2$SSTINYAPSLK$X_{11}X_{12}$F$X_{13}$ISRD-NAKNTLYLQM$X_{14}X_{15}X_{16}$R$X_{17}$EDTA$X_{18}$YYCASLYY-DYGDAZ$_3$ DYWGQGT$X_{19}$VTVSS (SEQ ID No. 53), wherein X1: Q, E; X2: Q, V; X3: Q, E; X4: K, R; X5: I, F; X6: D, T; X7: S, D; X8: R, D; X9: R, Q; X10: I, V; X11: D, G; X12: K, R; X13: I, T; X14: S, N; X15: K, S; X16: V, L; X17: S, A; X18: L, V; X19: S, L;

and wherein at least one of $Z_1$: I, F, L, V, Y. C, G, A, S, T, preferably I or F; $Z_2$: S, N, T, G, K, R, D, preferably S and/or $Z_3$: Y, L, F, I, V, A, C, preferably Y;

and wherein said antibody or fragment thereof specifically binds an epitope of the extracellular domain of CD269 (BCMA).

This embodiment encompasses various humanized sequences for the CAR of the present invention, in particular the VH sequences thereof, all variants defined by the advantageous humanization carried out in the CDRs as described herein.

The invention further relates to an antibody or antibody fragment as described herein comprising a VL domain, wherein said VL domain comprises a sequence according to DIVMTQSX$_1X_2X_3X_4X_5X_6$SVGD$X_7$V$X_8X_9$TCKASQSV-ESNVAWYQQKP$X_{10}$Q$X_{11}$PK$X_{12}$LI$X_{13}$S$X_{14}$ $X_{15}$LRFSG-VPARF$X_{16}$GSGSGTDFILTIS$X_{17}$LQSED$X_{18}$A$X_{19}$Y$X_{20}$ CQQYNNYPLTFGAGTKLELK R (SEQ ID No. 54), wherein X1: Q, P; X2: R, A; X3: F, T; X4: M, L; X5: T, S; X6: T, V; X7: R, E; X8: S, T; X9: V, L; X10: R, G; X11: S, A; X12: A, L; X13: F, Y; X14: A, D; X15: S, D; X16: T, S; X17: N, S; X18: L, F; X19: E, V; X20: F, Y;

and wherein said antibody or fragment thereof specifically binds an epitope of the extracellular domain of CD269 (BCMA).

This embodiment encompasses various humanized sequences for the CAR of the present invention, in particular the VL sequences thereof, all variants defined by the advantageous humanization carried out in the CDRs as described herein.

In one embodiment the isolated chimeric antigen receptor polypeptide (CAR) of the present invention is characterised in that the extracellular antigen-binding domain comprises a linker polypeptide positioned between the VH and VL domains, wherein said linker is preferably selected from a Whitlow (SEQ ID NO 13; GSTSGSGKPGSGEGSTKG) or Gly-Ser (SEQ ID NO 14; SSGGGGSGGGGSGGGGS) linker, or linkers with at least 80% sequence identity to SEQ ID NO 13 or 14.

In one embodiment the isolated chimeric antigen receptor polypeptide (CAR) of the present invention is characterised in that said CAR comprises a spacer polypeptide positioned between the extracellular antigen-binding domain and the transmembrane domain, wherein said spacer is preferably selected from:

IgG1-CD28 spacer (SEQ ID NO 15;
PAEPKSPDKTHTCPPCPAPPVAGPSVFLFPPKPKDTLMIARTPEVTCVVV
DVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDK
SRWQQGNVFSCSVMHEALHNHYTQKSLSLSPGKK), IgG1Δ-4-1BB spacer (SEQ ID NO 16;
PAEPKSPDKTHTCPPCPAPPVAGPSVFLFPPKPKDTLMIARTPEVTCVVV
DVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDK
SRWQQGNVFSCSVMHEALHNHYTQKSLSSLSPGKK), IgG4 (Hi-CH2-CH3) spacer (SEQ ID NO 17;
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK), IgG4 (Hi-CH3) spacer (SEQ ID NO 18;
ESKYGPPCPPCPGQPREPQVYTLPPSQEEMTKNQVSLTCLVKGFYPSDIA
VEWESNGQPENNYKTTPPVLDSDGSFFLYSRLTVDKSRWQEGNVFSCSVM
HEALHNHYTQKSLSLSLGK), IgG4 (Hi) spacer (SEQ ID NO 19;
ESKYGPPCPPCP), or a spacer with at least 80% sequence identity to any one of SEQ ID NO 15 to 19;

In one embodiment the isolated chimeric antigen receptor polypeptide (CAR) of the present invention is characterised in that the transmembrane domain is preferably selected from a CD8a domain (SEQ ID NO 20; IYI- WAPLAGTCGVLLLSLVITLYC) or a CD28 domain (SEQ ID NO 21; FWVLVVVGGVLACYSLLVTVAFIIFWV), or transmembrane domains with at least 80% sequence identity to SEQ ID NO 20 or 21.

In one embodiment the isolated chimeric antigen receptor polypeptide (CAR) of the present invention is characterised in that the intracellular domain comprises a co-stimulatory domain, preferably selected from a 4-1BB co-stimulatory domain (SEQ ID NO 22; KRGRKKLLY-IFKQPFMRPVQTTQEEDGCSCRFPEEEEGGCEL) or a CD28 co-stimulatory domain (SEQ ID NO 23; RSKRSRLLHSDYMNMTPRRPGPTRKHYQPYAPPRD-FAAYRS), or a co-stimulatory domain with at least 80% sequence identity to SEQ ID NO 22 or 23; and/or In one embodiment the isolated chimeric antigen receptor polypeptide (CAR) of the present invention is characterised in that said CAR comprises a signaling domain, wherein said signaling domain is preferably selected from a CD3zeta (CD28 or 4-1BB) signaling domain (SEQ ID NO 24; LRVKFSRSADAPAYQQGQNQLYNELNLGRREEY-DVLDKRRGRDPEMGGKPRRKNPQEGLY NELQKDK-MAEAYSEIGMKGERRRGKGHDGLYQGLSTATKDTY-DALHMQALPPR), or a signaling domain with at least 80% sequence identity to SEQ ID NO 24.

In one embodiment the isolated chimeric antigen receptor (CAR) of the present invention is characterised in that said CAR comprises a tandem co-stimulatory domain, comprising a 4-1BB co-stimulatory domain (SEQ ID NO 22) and a CD28 co-stimulatory domain (SEQ ID NO 23), and a CD3zeta signaling/activation domain (SEQ ID NO 24).

In one embodiment the isolated chimeric antigen receptor polypeptide (CAR) of the present invention is characterised in that said CAR comprises a leader sequence, wherein said leader sequence is preferably selected from the IgK leader (SEQ ID NO 55; MDFQVQIFSFLLISASVIMSR) or the GMCSF leader (SEQ ID NO 56; MLLLVTSLLLCEL-PHPAFLLI), or a leader sequence with at least 80% sequence identity to SEQ ID NO 55 or 56.

A further aspect of the invention relates to an isolated nucleic acid molecule selected from the group consisting of:
a) a nucleic acid molecule comprising a nucleotide sequence
   which encodes an isolated chimeric antigen receptor (CAR) polypeptide as described herein, and/or
   comprising a sequence or sequence fragment of SEQ ID No. 66 and/or 67, or SEQ ID NO 86 to 94, or
b) a nucleic acid molecule which is complementary to a nucleotide sequence in accordance with a);
c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 80%;
d) a nucleic acid molecule which, as a consequence of the genetic code, is degenerated into a nucleotide sequence according to a) through c); and
e) a nucleic acid molecule according to a nucleotide sequence of a) through d) which is modified by deletions, additions, substitutions, translocations, inversions and/or insertions and functionally analogous/equivalent to a nucleotide sequence according to a) through d).

Preferred Amino Acid Sequences of the Present Invention:

| SEQ ID No. | Sequence | Description |
|---|---|---|
| 1 | GFTFSRYW | H-CDR1 |
| 2 | INPSSSTI | H-CDR2 |
| 3 | ASLYYDYGDAYDY | H-CDR3 |
| 4 | QSVESN | L-CDR1 |
| 5 | SASX<br>Wherein X is any amino acid, preferably L, or wherein the sequence is SAS, without definition of position X | L-CDR2 |
| 6 | QQYNNYPLT | L-CDR3 |
| 7 | INPX$_2$X$_3$STI<br>wherein X$_2$X$_3$: SS, NS, TS, GS, KS, RS, SD, SN, DE | H-CDR2 |
| 8 | ASLYX$_4$DYGDAX$_5$DY<br>wherein X$_4$: Y, L, A, V, F, I, W, and/or X$_5$: Y, L, F, I, V, A, C | H-CDR3 |
| 9 | QSVX$_1$X$_2$N<br>wherein X$_1$X$_2$: ES, SS, TS, QS, HS, DH | L-CDR1 |
| 10 | QQYNNYPLTFG | L-CDR3 |
| 11 | EVQLVESGGGLVQPGGSLRLSCAASGFTFSRYWFSWVRQAPGKGLV<br>WVGEINPSSSTINYAPSLKDKFTISRDNAKNTLYLQMNSLRAEDTAVYY<br>CASLYYDYGDAYDYWGQGTLVTVSS | VH domain |
| 12 | EIVMTQSPATLSVSPGERATLSCKASQSVESNVAWYQQKPGQAPRALI<br>YSASLRFSGIPARFSGSGSGTEFTLTISSLQSEDFAVYYCQQYNNYPLT<br>FGAGTKLELK | VL domain |

-continued

| SEQ ID No. | Sequence | Description |
|---|---|---|
| 13 | GSTSGSGKPGSGEGSTKG | Whitlow linker |
| 14 | SSGGGGSGGGGSGGGGS | Gly-Ser linker |
| 15 | PAEPKSPDKTHTCPPCPAPPVAGPSVFLFPPKPKDTLMIARTPEVTCV<br>VVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSRDE<br>LTKNQVSLTCLVKGFYPSDIAVEWESNGQPENNYKTTPPVLDSDGSFF<br>LYSKLTVDKSRWQQGNVFSCSVMHEALHNHYTQKSLSLSPGKK | IgG1-CD28 spacer |
| 16 | PAEPKSPDKTHTCPPCPAPPVAGPSVFLFPPKPKDTLMIARTPEVTCV<br>VVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSRDE<br>LTKNQVSLTCLVKGFYPSDIAVEWESNGQPENNYKTTPPVLDSDGSFF<br>LYSKLTVDKSRWQQGNVFSCSVMHEALHNHYTQKSLSSLSPGKK | IgG1Δ-4-1BB spacer |
| 17 | ESKYGPPCPPCPAPEFEGGPSVFLFPPKPKDTLMISRTPEVTCVVVDV<br>SQEDPEVQFNWYVDGVEVHNAKTKPREEQFNSTYRVVSVLTVLHQD<br>WLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYS<br>RLTVDKSRWQEGNVFSCSVMHEALHNHYTQKSLSLSLSLGK | IgG4 (Hi-CH2—CH3) spacer |
| 18 | ESKYGPPCPPCPGQPREPQVYTLPPSQEEMTKNQVSLTCLVKGFYPS<br>DIAVEWESNGQPENNYKTTPPVLDSDGSFFLYSRLTVDKSRWQEGNV<br>FSCSVMHEALHNHYTQKSLSLSLGK | IgG4 (Hi-CH3) spacer |
| 19 | ESKYGPPCPPCP | IgG4 (Hi) spacer |
| 20 | IYIWAPLAGTCGVLLLSLVITLYC | CD8α domain |
| 21 | FWVLVVVGGVLACYSLLVTVAFIIFWV | CD28 domain |
| 22 | KRGRKKLLYIFKQPFMRPVQTTQEEDGCSCRFPEEEEGGCEL | 4-1BB co-stimulatory domain |
| 23 | RSKRSRLLHSDYMNMTPRRPGPTRKHYQPYAPPRDFAAYRS | CD28 co-stimulatory domain |
| 24 | LRVKFSRSADAPAYQQGQNQLYNELNLGRREEYDVLDKRRGRDPEM<br>GGKPRRKNPQEGLYNELQKDKMAEAYSEIGMKGERRRGKGHDGLYQ<br>GLSTATKDTYDALHMQALPPR | CD3zeta (CD28 or 4-1BB) signaling domain |
| 25 | RYWFS | H-CDR1 |
| 26 | EINPSSSTINYAPSLKDK | H-CDR2 |
| 27 | SLYYDYGDAYDYW | H-CDR3 |
| 28 | KASQSVESNVA | L-CDR1 |
| 29 | SASLRFS | L-CDR2 |
| 30 | QQYNNYPLTFG | L-CDR3 |
| 31 | MAGQCSQNEYFDSLLHACIPCQLRCSSNTPPLTCQRYCNASVTNSVK<br>GTNALE | BCMA extracellular domain |
| 32 | MLQMAGQCSQNEYFDSLLHACIPCQLRCSSNTPPLTCQRYCNASVTN<br>SVKGTNALE | BCMA N-terminus sequence |
| 33 | YFDSLLHACIPCQLRCSSNT | BCMA antibody epitope—amino acids 13 to 32 of BCMA |

-continued

| SEQ ID No. | Sequence | Description |
|---|---|---|
| 34 | RYWX₁S<br>Wherein:<br>X₁: I, F, L, V, Y. C, G, A, S, T, preferably I or F | H-CDR1 |
| 35 | EINPX₂X₃STINYAPSLKDK<br>Wherein:<br>X₂X₃: SS, NS, TS, GS, KS, RS, SD, SN, DE, preferably SS | H-CDR2 |
| 36 | SLYX₄DYGDAX₅DYW<br>Wherein:<br>X₄: Y, L, A, V, F, I, W, preferably Y; and/or<br>X₅: Y, L, F, I, V, A, C, preferably Y | H-CDR3 |
| 37 | KASQSVX₁X₂NVA<br>Wherein:<br>X₁X₂: ES, SS, TS, QS, HS, DH, preferably ES | L-CDR1 |
| 38 | QVQLQQSGGGLVQPGGSLKLSCAASGIDFSRYWMSWVRRAPGKGLE<br>WIGEINPDSSTINYAPSLKDKFIISRDNAKNTLYLQMSKVRSEDTALYYC<br>ASLYYDYGDAMDYWGQGTSVTVSS | HC (VH) mouse |
| 39 | EVQLVESGGGLVQPGGSLRLSCAASGFTFDDYWMSWVRQAPGKGLE<br>WVGEINPDSSTINYAPSLKGRFTISRDNAKNTLYLQMNSLRAEDTAVYY<br>CASLYYDYGDAMDYWGQGTLVTVSS | HC partially humanized |
| 40 | EVQLVESGGGLVQPGGSLRLSCAASGFTFSRYWMSWVRQAPGKGLV<br>WVGEINPDSSTINYAPSLKDKFTISRDNAKNTLYLQMNSLRAEDTAVYY<br>CASLYYDYGDAMDYWGQGTLVTVSS | hHC01 |
| 41 | EVQLVESGGGLVQPGGSLRLSCAASGFTFSRYWX₁SWVRQAPGKGL<br>VWVGEINPX₂X₃STINYAPSLKDKFTISRDNAKNTLYLQMNSLRAEDTAV<br>YYCASLYX₄DYGDAX₅DYWGQGTLVTVSS<br>Wherein<br>X₁: I, F, L, V, Y. C, G, A, S, T, preferably I or F;<br>X₂X₃: SS, NS, TS, GS, KS, RS, SD, SN, DE, preferably SS;<br>X₄: Y, L, A, V, F, I, W, preferably Y; and/or<br>X₅: Y, L, F, I, V, A, C, preferably Y | hHC02 |
| 42 | EVQLVESGGGLVQPGGSLRLSCAASGFTFSRYX₁MX₂WVRQAPGKGL<br>VX₃VGX₄INPDSSTINYAPSLKDKFTISRDNAKNTLYLQMNSLRAEDTAV<br>YYCASX₅X₆X₇DYGDX₈MDYWGQGTLVTVSS<br>Wherein<br>X₁: W, F, Y, preferred W;<br>X₂: S, T, N, Q, D, E, preferred S;<br>X₃: W, F, Y, preferred W;<br>X₄: E, Q, preferred E;<br>X₅: L, I, V, G, A, preferred L;<br>X₆: Y, X, preferred Y;<br>X₇: Y, F, L, I, V, M, preferred Y; and/or<br>X₈: A, G, V, preferred A | hHC03 |
| 43 | EVQLVESGGGLVQPGGSLRLSCAASGFTFSRYWISWVRQAPGKGLV<br>WVGEINPNSSTINYAPSLKDKFTISRDNAKNTLYLQMNSLRAEDTAVYY<br>CASLYYDYGDAYDYWGQGTLVTVSS | hHC04 |
| 44 | EVQLVESGGGLVQPGGSLRLSCAASGFTFSRYWFSWVRQAPGKGLV<br>WVGEINPNSSTINYAPSLKDKFTISRDNAKNTLYLQMNSLRAEDTAVYY<br>CASLYYDYGDAYDYWGQGTLVTVSS | hHC05 |
| 45 | EVQLVESGGGLVQPGGSLRLSCAASGFTFSRYWISWVRQAPGKGLV<br>WVGEINPSSSTINYAPSLKDKFTISRDNAKNTLYLQMNSLRAEDTAVYY<br>CASLYYDYGDAYDYWGQGTLVTVSS | hHC06 |
| 46 | EVQLVESGGGLVQPGGSLRLSCAASGFTFSRYWFSWVRQAPGKGLV<br>WVGEINPSSSTINYAPSLKDKFTISRDNAKNTLYLQMNSLRAEDTAVYY<br>CASLYYDYGDAYDYWGQGTLVTVSS | hHC07 |
| 47 | DIVMTQSQRFMTTSVGDRVSVTCKASQSVDSNVAWYQQKPRQSPKA<br>LIFSASLRFSGVPARFTGSGSGTDFTLTISNLQSEDLAEYFCQQYNNYP<br>LTFGAGTKLELKR | LC (VL) mouse |
| 48 | DIVMTQSPATLSVSVGDEVTLTCKASQSVDSNVAWYQQKPGQAPKLLI<br>YSDDLRFSGVPARFSGSGSGTDFTLTISSLQSEDFAVYYCQQYNNYPL<br>TFGAGTKLELKR | LC partially humanized |

| SEQ ID No. | Sequence | Description |
|---|---|---|
| 49 | EIVMTQSPATLSVSPGERATLSCKASQSVDSNVAWYQQKPGQAPRAL IYSASLRFSGIPARFSGSGSGTEFTLTISSSLQSEDFAVYYCQQYNNYPL TFGAGTKLELKR | hLC01 |
| 50 | EIVMTQSPATLSVSPGERATLSCKASQSVX₁X₂NVAWYQQKPGQAPRA LIYSASLRFSGIPARFSGSGSGTEFTLTISSLQSEDFAVYYCQQYNNYP LTFGAGTKLELKR<br>Wherein:<br>X₁X₂: ES, SS, TS, QS, HS, DH, preferably ES. | hLC02 |
| 51 | EIVMTQSPATLSVSPGERATLSCKASQSVDX₁X₂VX₃WX₄QQKPGQAPR ALIX₅X₆AX₇X₈RX₉SGIPARFSGSX₁₀X₁₁GTEFTLTISSLQSEDFAVYYCX₁₂ QX₁₃NNX₁₄PX₁₅TFGAGTKLELKR<br>Wherein:<br>X₁: S, H, T, N, D, Q;<br>X₂: N, E, Q;<br>X₃: A, G, V, S, T, L, I;<br>X₄: Y, F, L, I, V, A, G;<br>X₅: Y, F, L;<br>X₆: S, T;<br>X₇: S, T, D, N, H, E, Q;<br>X₈: L, V, I, M;<br>X₉: F, L, I, V, Y, M;<br>X₁₀: G, X;<br>X₁₁: S, X;<br>X₁₂: Q, V, L, I, M;<br>X₁₃: Y, F, L, I, Q;<br>X₁₄: Y, F, R, Q, K; and/or<br>X₁₅: L, I, V, F | hLC03 |
| 52 | EIVMTQSPATLSVSPGERATLSCKASQSVESNVAWYQQKPGQAPRALI YSASLRFSGIPARFSGSGSGTEFTLTISSLQSEDFAVYYCQQYNNYPLT FGAGTKLELKR | hLC04 |
| 53 | X₁VQLX₂X₃SGGGLVQPGGSLX₄LSCAASGX₅X₆FX₇X₈YWZ₁SWVRX₉AP GKGLEWX₁₀GEINPZ₂SSTINYAPSLKX₁₁X₁₂FX₁₃ISRDNAKNTLYLQMX₁₄ X₁₅X₁₆RX₁₇EDTAX₁₈YYCASLYYDYGDAZ₃DYWGQGTX₁₉VTVSS<br>wherein X1: Q, E; X2: Q, V; X3: Q, E; X4: K, R; X5: I, F; X6: D, T; X7: S, D; X8: R, D; X9: R, Q; X10: I, V; X11: D, G; X12: K, R; X13: I, T; X14: S, N; X15: K, S; X16: V, L; X17: S, A; X18: L, V; X19: S, L;<br>and wherein at least one of Z₁: I, F, L, V, Y. C, G, A, S, T, preferably I or F; Z₂: S, N, T, G, K, R, D, preferably S and/or Z₃: Y, L, F, I, V, A, C, preferably Y; | VH hum Gen |
| 54 | DIVMTQSX₁X₂X₃X₄X₅X₆SVGDX₇VX₈X₉TCKASQSVESNVAWYQQKPX₁₀ QX₁₁PKX₁₂LIX₁₃SX₁₄X₁₅LRFSGVPARFX₁₆GSGSGTDFTLTISX₁₇LQSED X₁₈AX₁₉YX₂₀CQQYNNYPLTFGAGTKLELKR<br>wherein X1: Q, P; X2: R, A; X3: F, T; X4: M, L; X5: T, S; X6: T, V; X7: R, E; X8: S, T; X9: V, L; X10: R, G; X11: S, A; X12: A, L; X13: F, Y; X14: A, D; X15: S, D; X16: T, S; X17: N, S; X18: L, F; X19: E, V; X20: F, Y; | VL hum Gen |
| 55 | MDFQVQIFSFLLISASVIMSR | IgK leader |
| 56 | MLLLVTSLLLCELPHPAFLLI | GMCSF leader |
| 57 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKPAEPKSPDKTHTCPPCPAPP VAGPSVFLFPPKPKDTLMIARTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIA VEWESNGQPENNYKTTPPVLDSDGSFFLYSKLTVDKSRWQQGNVFS CSVMHEALHNHYTQKSLSLSPGKKDPKFWVLVVVGGVLACYSLLVTV AFIIFWVRSKRSRLLHSDYMNMTPRRPGPTRKHYQPYAPPRDFAAYR SLRVKFSRSADAPAYQQGQNQLYNELNLGRREEYDVLDKRRGRDPE MGGKPRRKNPQEGLYNELQKDKMAEAYSEIGMKGERRRGKGHDGLY QGLSTATKDTYDALHMQALPPR | Construct IX IX_MP71-hBCMA-VH-WL-VL_IgG1_CD28_CD3z |
| 58 | MDFQVQIFSFLLISASVIMSREIVMTQSPATLSVSPGERATLSCKASQS VESNVAWYQQKPGQAPRALIYSASLRFSGIPARFSGSGSGTEFTLTISS LQSEDFAVYYCQQYNNYPLTFGAGTKLELKGSTSGSGKPGSGEGSTK GEVQLVESGGGLVQPGGSLRLSCAASGFTFSRYWFSWVRQAPGKGL | Construct X X_MP71-hBCMA-VL-WL- |

-continued

| SEQ ID No. | Sequence | Description |
|---|---|---|
| | VWVGEINPSSSTINYAPSLKDKFTISRDNAKNTLYLQMNSLRAEDTAVY YCASLYYDYGDAYDYWGQGTLVTVSSPAEPKSPDKTHTCPPCPAPPV AGPSVFLFPPKPKDTLMIARTPEVTCVVVDVSHEDPEVKFNWYVDGVE VHNAKTKPREEQYNSTYRVVSVLTVLHQDWLNGKEYKCKVSNKALPA PIEKTISKAKGQPREPQVYTLPPSRDELTKNQVSLTCLVKGFYPSDIAV EWESNGQPENNYKTTPPVLDSDGSFFLYSKLTVDKSRWQQGNVFSC SVMHEALHNHYTQKSLSLSPGKKDPKFWVLVVVGGVLACYSLLVTVA FIIFWVRSKRSRLLHSDYMNMTPRRPGPTRKHYQPYAPPRDFAAYRSL RVKFSRSADAPAYQQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR | VH_IgG1_CD28_CD3z |
| 59 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKPAEPKSPDKTHTCPPCPAPP VAGPSVFLFPPKPKDTLMIARTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIA VEWESNGQPENNYKTTPPVLDSDGSFFLYSKLTVDKSRWQQGNVFS CSVMHEALHNHYTQKSLSLSPGKKDPKFWVLVVVGGVLACYSLLVTV AFIIFWVRSKRSRLLHSDYMNMTPRRPGPTRKHYQPYAPPRDFAAYR SLRVKFSRSADAPAYQQGQNQLYNELNLGRREEYDVLDKRRGRDPE MGGKPRRKNPQEGLYNELQKDKMAEAYSEIGMKGERRRGKGHDGLY QGLSTATKDTYDALHMQALPPR | Construct XI XI_MP71-hBCMA-VH-WL-VL_IgG1_CD28_CD3z_no_opt |
| 60 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKESKYGPPCPPCPAPEFEGGP SVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVM HEALHNHYTQKSLSLSLGKFWVLVVVGGVLACYSLLVTVAFIIFWVRSK RSRLLHSDYMNMTPRRPGPTRKHYQPYAPPRDFAAYRSLRVKFSRSA DAPAYQQGQNQLYNELNLGRREEYDVLDKRRGRDPEMGGKPRRKNP QEGLYNELQKDKMAEAYSEIGMKGERRRGKGHDGLYQGLSTATKDTY DALHMQALPPR | Construct XII XII_new_cuts_MP71-hBCMA-VH-WL-VL_IgG4_CD28_CD3z |
| 61 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKESKYGPPCPPCPGQPREPQV YTLPPSQEEMTKNQVSLTCLVKGFYPSDIAVEWESNGQPENNYKTTP PVLDSDGSFFLYSRLTVDKSRWQEGNVFSCSVMHEALHNHYTQKSLS LSLGKFWVLVVVGGVLACYSLLVTVAFIIFWVRSKRSRLLHSDYMNMT PRRPGPTRKHYQPYAPPRDFAAYRSLRVKFSRSADAPAYQQGQNQL YNELNLGRREEYDVLDKRRGRDPEMGGKPRRKNPQEGLYNELQKDK MAEAYSEIGMKGERRRGKGHDGLYQGLSTATKDTYDALHMQALPPR | Construct XIII XIII_new_cuts_MP71-hBCMA-VH-WL-VL_IgG4_HI_CH3_CD28_CD3z |
| 62 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKESKYGPPCPPCPFWVLVVVG GVLACYSLLVTVAFIIFWVRSKRSRLLHSDYMNMTPRRPGPTRKHYQP YAPPRDFAAYRSLRVKFSRSADAPAYQQGQNQLYNELNLGRREEYDV LDKRRGRDPEMGGKPRRKNPQEGLYNELQKDKMAEAYSEIGMKGER RRGKGHDGLYQGLSTATKDTYDALHMQALPPR | Construct XIV XIV_new_cuts_MP71-hBCMA-VH-WL-VL_IgG4_HI_CD28_CD3z |
| 63 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKPAEPKSPDKTHTCPPCPAPP VAGPSVFLFPPKPKDTLMIARTPEVTCVVVDVSHEDPEVKFNWYVDGV | Construct XV XV_MP71-hBCMA-VH-WL-VL_IgGdelta_CD8_4-1BB_CD3z |

| SEQ ID No. | Sequence | Description |
|---|---|---|
| | EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFS<br>CSVMHEALHNHYTQKSLSSLSPGKKIYIWAPLAGTCGVLLLSLVITLYC<br>KRGRKKLLYIFKQPFMRPVQTTQEEDGCSCRFPEEEEGGCELLRVKF<br>SRSADAPAYQQGQNQLYNELNLGRREEYDVLDKRRGRDPEMGGKPR<br>RKNPQEGLYNELQKDKMAEAYSEIGMKGERRRGKGHDGLYQGLSTA<br>TKDTYDALHMQALPPR | |
| 64 | MDFQVQIFSFLLISASVIMSREIVMTQSPATLSVSPGERATLSCKASQS<br>VESNVAWYQQKPGQAPRALIYSASLRFSGIPARFSGSGSGTEFTLTISS<br>LQSEDFAVYYCQQYNNYPLTFGAGTKLELKGSTSGSGKPGSGEGSTK<br>GEVQLVESGGGLVQPGGSLRLSCAASGFTFSRYWFSWVRQAPGKGL<br>VWVGEINPSSSTINYAPSLKDKFTISRDNAKNTLYLQMNSLRAEDTAVY<br>YCASLYYDYGDAYDYWGQGTLVTVSSPAEPKSPDKTHTCPPCPAPPV<br>AGPSVFLFPPKPKDTLMIARTPEVTCVVVDVSHEDPEVKFNWYVDGVE<br>VHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAV<br>EWESNGQPENNYKTTPPVLDSDGSFFLYSKLTVDKSRWQQGNVFSC<br>SVMHEALHNHYTQKSLSSLSPGKKIYIWAPLAGTCGVLLLSLVITLYCK<br>RGRKKLLYIFKQPFMRPVQTTQEEDGCSCRFPEEEEGGCELLRVKFS<br>RSADAPAYQQGQNQLYNELNLGRREEYDVLDKRRGRDPEMGGKPRR<br>KNPQEGLYNELQKDKMAEAYSEIGMKGERRRGKGHDGLYQGLSTAT<br>KDTYDALHMQALPPR | Construct XVI<br>XVI_MP71-<br>hBCMA-VL-<br>WL-<br>VH_IgGdelta_CD8_4-<br>1BB_CD3z |
| 65 | MDFQVQIFSFLLISASVIMSREVQLVESGGGLVQPGGSLRLSCAASGF<br>TFSRYWFSWVRQAPGKGLVWVGEINPSSSTINYAPSLKDKFTISRDNA<br>KNTLYLQMNSLRAEDTAVYYCASLYYDYGDAYDYWGQGTLVTVSSGS<br>TSGSGKPGSGEGSTKGEIVMTQSPATLSVSPGERATLSCKASQSVES<br>NVAWYQQKPGQAPRALIYSASLRFSGIPARFSGSGSGTEFTLTISSLQS<br>EDFAVYYCQQYNNYPLTFGAGTKLELKPAEPKSPDKTHTCPPCPAPP<br>VAGPSVFLFPPKPKDTLMIARTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFS<br>CSVMHEALHNHYTQKSLSSLSPGKKIYIWAPLAGTCGVLLLSLVITLYC<br>KRGRKKLLYIFKQPFMRPVQTTQEEDGCSCRFPEEEEGGCELLRVKF<br>SRSADAPAYQQGQNQLYNELNLGRREEYDVLDKRRGRDPEMGGKPR<br>RKNPQEGLYNELQKDKMAEAYSEIGMKGERRRGKGHDGLYQGLSTA<br>TKDTYDALHMQALPPR | Construct XVII<br>XVII_MP71-<br>hBCMA-VH-<br>WL-<br>VL_IgGdelta_CD8_4-<br>1BB_CD3z_no_opt |

Preferred Nucleotide Sequences:

| | | |
|---|---|---|
| 66 | gaggtgcagctggtggaatctggcggaggactggtgcagcctggcggctctctgagactgtcttgtgc<br>cgccagcggcttcaccttcagccggtactggtttagctgggtgcgccaggcccctggcaagggactcg<br>tgtgggtgggagagatcaaccccagcagcagcaccatcaactacgcccccagcctgaaggacaa<br>gttcaccatcagcagagacaacgccaagaacaccctgtacctgcagatgaacagcctgcgggccg<br>aggacaccgccgtgtactattgtgccagcctgtactacgactacggcgacgcctacgattactgggc<br>cagggcacactggtgactgttagctcc | Codon<br>optimized VH |
| 67 | Gagatcgtgatgacacagagccctgccaccctgagcgtgtccccaggcgaaagagctaccctgag<br>ctgcaaggccagccagagcgtggaaagcaacgtggcctggtatcagcagaagcccggcagggct<br>cctcggggcctgatctacagcgccagcctgagattcagcggcatccccgccaggtttagcggctctgg<br>cagcggcaccgagttcaccctgacaatcagcagcctgcagagcgaggactttgccgtgtattactgc<br>cagcagtacaacaactacccccctgaccttcggagccggcaccaagctggagctgaag | Codon<br>optimized VL |
| 68 | gaagtgcagctggtcgaatctggaggaggcctggttcagcctggtggcagccttaggctctcttgtgca<br>gcctctggcttttaccttctcacggtattggttcagctgggtgagacaggctccagggaaaggtctggtgt<br>gggtaggggagataaaccccagcagcagcacgatcaactatgctccgtcactgaaagacaagttc<br>accatttccgcgataatgccaagaacactctctacttgcagatgaattcccttcgagccgaggataca<br>gcggtgtactactgcgccagtctgtactacgactatggggacgcatacgactattggggacaaggca<br>cactggtgactgttagctcc | VH without<br>Codon<br>Optimization -<br>mAb scFv |
| 69 | Gagatcgtgatgacccagtctcctgctaccctgagcgtttctcccggtgaaagggccacactcagctg<br>caaagcctctcaaagcgtggagagcaatgtcgcctggtatcagcagaaacctggccaagctccgag<br>agcactgatctattccgcgtcattgcgcttttcggcataccagcacggtttagtggctcagggagtggg<br>actgagttcactctgacgattagctcccttcagtcagaggatttcgccgtgtactactgtcagcagtacaa<br>caactatccccctcacattcggagctggaaccaagctggaactgaag | VL without<br>Codon<br>Optimization -<br>mAb scFv |

| | | |
|---|---|---|
| 70 | atggatttccaggtgcagatcttcagcttcctgctgatctccgccagcgtgatcatgagccgc | IgK leader |
| 71 | atgcttctcctggtgacaagccttctgctctgtgagttaccacacccagcattcctcctgatc | GMCSF leader |
| 72 | ggcagcaccagcggctccggcaagcctggctctggcgagggcagcacaaaggga | Whitlow linker |
| 73 | tctagcggcggaggcggatctggcggggaggatctgggggaggcggctct | Gly-Ser linker |
| 74 | Cctgccgagcctaagagccccgacaagacccacacctgtcccccttgtcctgcccctccagtggctg gccctagcgtgttcctgttccccccaaagcccaaggataccctgatgatcgcccggaccccgaagtc acatgcgtggtggtggacgtgagccacgaagaccctgaggtcaagttcaactggtacgtggacggc gtggaggtgcataatgccaagacaaagccgcgggaggagcagtacaacagcacgtaccgtgtggt cagcgtcctcaccgtcctgcaccaggactggctgaatggcaaggagtacaagtgcaaggtctccaa caaagccctcccagccccatcgagaaaaccatctccaaagccaaagggcagccccgagaacc acaggtgtacaccctgcccccatcccgggatgagctgaccaagaaccaggtcagcctgacctgcct ggtcaaaggcttctatcccagcgacatcgccgtggagtgggagagcaatgggcagccggagaaca actacaagaccacgcctcccgtgctggactccgacggctccttcttcctctacagcaagctcaccgtgg acaagagcaggtggcagcaggggaacgtcttctcatgctccgtgatgcatgaggctctgcacaacca ctacacgcagaagagcctctccctgtctccgggtaaaaaa | IgG1 - CD28 Backbone spacer |
| 75 | Cctgccgagcctaagagccccgacaagacccacacctgtcccccttgtcctgcccctccagtggctg gccctagcgtgttcctgttccccccaaagcccaaggataccctgatgatcgcccggaccccgaagtc acatgcgtggtggtggacgtgagccacgaagaccctgaggtcaagttcaactggtacgtggacggc gtggaggtgcataatgccaagacaaagccgcgggaggagcagtacaacagcacgtaccgtgtggt cagcgtcctcaccgtcctgcaccaggactggctgaatggcaaggagtacaagtgcaaggtctccaa caaagccctcccagccccatcgagaaaaccatctccaaagccaaagggcagccccgagaacc acaggtgtacaccctgcccccatcccgggatgagctgaccaagaaccaggtgtccctgacctgcctc gtgaagggcttctaccctccagatatcgccgtggaatgggagagcaatggccagccggagaacaac tacaagaccacccccctgtgctggacagcgacggctcattcttcctgtacagcaagctgacagtgga caagagccggtggcagcagggcaacgtgttcagctgcagcgtgatgcacgaggctctgcacaacc actacacccagaagtccctgagcagcctgagcccaggcaagaag | IgG1Δ-4-1BB Backbone spacer |
| 76 | Gagagcaagtacggccctccctgcccccttgccctgccccgagttcgagggcggacccagcgtg ttcctgttccccccaagcccaagacacctgatgatcagccggaccccgaggtgacctgcgtgg tggtggacgtgagccaggaagatcccgaggtccagttcaattggtacgtggacggcgtggaagtgca caacgccaagaccaagccagagaggaacagttcaacagcacctaccgggtggtgtctgtgctga ccgtgctgcaccaggactggctgaacggcaaagaatacaagtgcaaggtgtccaacaagggcctg cccagcagcatcgaaaagaccatcagcaaggccaagggccagcctcgcgagccccaggtgtaca ccctgcctccctcccaggaagagatgaccaagaaccaggtgtccctgacctgcctggtgaagggctt ctaccccagcgacatcgccgtggagtgggagagcaacggccagcctgagaacaactacaagacc accccctccgtgctggacagcgacggcagcttcttcctctacagccggctgaccgtggacaagagcc ggtggcaggaaggcaacgtctttagctgcagcgtgatgcacgaggccctgcacaaccactacaccc agaagagcctgagcctgtccctgggcaag | IgG4 (Hi-CH2—CH3) spacer |
| 77 | Gagagcaagtacggccctccctgcccccttgccctggccagcctcgcgagccccaggtgtacacc ctgcctccctcccaggaagagatgaccaagaaccaggtgtccctgacctgcctggtgaagggcttct accccagcgacatcgccgtggagtgggagagcaacggccagcctgagaacaactacaagacca ccccctccgtgctggacagcgacggcagcttcttcctctacagccggctgaccgtggacaagagccg gtggcaggaaggcaacgtctttagctgcagcgtgatgcacgaggccctgcacaaccactacaccca gaagagcctgagcctgtccctgggcaag | IgG4 (Hi-CH3) spacer |
| 78 | Gagagcaagtacggccctccctgcccccttgccct | IgG4 (Hi) spacer |
| 79 | Atctacatctgggcccctctggccggcacctgtggcgtgctgctgctgtctctcgtgatcacactgtactgc | CD8α transmembrane domain |
| 80 | Ttttgggtgctggtggtggttggtggagtcctggcttgctatagcttgctagtaacagtggcctttattattttc tgggtg | CD28 transmembrane domain |
| 81 | aagcggggcagaaagaagctgctgtacatcttcaagcagcccttcatgcggcccgtgcagaccacc caggaagaggacggctgctcctgcagattccccgaggaagaaggcggctgcgagctg | 4-1BB Co-stimulatory domain |
| 82 | Aggagtaagaggagcaggctcctgcacagtgactacatgaacatgactccccgccgccccgggcc caccccgcaagcattaccagccctatgccccaccacgcgacttcgcagcctatcgctcc | CD28 (constructs IX-XI) Co-stimulatory domain |
| 83 | Aggagtaagaggagcaggctcctgcacagtgactacatgaacatgactccccgtcgacccgggcc caccccgcaagcattaccagccctatgccccaccacgcgacttcgcagcctatcgctcc | CD28 (constructs XII-XIV) (additional cleavage site for SalI added) Co-stimulatory domain |

| | | |
|---|---|---|
| 84 | Ctgagagtgaagttcagcaggagcgcagacgcccccgcgtaccagcagggccagaaccagctct<br>ataacgagctcaatctaggacgaagagaggagtacgatgtttggacaagagacgtggccgggac<br>cctgagatgggggaaagccgagaaggaagaaccctcaggaaggcctgtacaatgaactgcaga<br>aagataagatggcggaggcctacagtgagattgggatgaaaggcgagcgccggaggggcaagg<br>ggcacgatggcctttaccagggtctcagtacagccaccaaggacacctacgacgcccttcacatgca<br>ggccctgccccctcgctga | CD3zeta<br>(CD28)<br>Signaling<br>domain |
| 85 | ctgcgcgtgaagttttctagaagcgccgacgcccctgcctaccagcagggccagaaccagctgtaca<br>acgagctgaacctgggcagacggaagagtacgacgtgctggataagcgggagaggccgggacc<br>ctgagatgggcggcaagcctagaagaaagaaccccaggaaggcctgtataacgaactgcagaa<br>agacaagatggccgaggcctacagcgagatcggaatgaagggcgagcggagaagaggcaagg<br>ccacgatggactgtaccagggcctgagcaccgccaccaaggacacctatgacgccctgcacatg<br>caggctctgccccccaga | CD3zeta (4-<br>1BB) Signaling<br>domain |
| 86 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagcagctactggttagctgggtgcgccaggccccgtcaagggactcgtgtgggtg<br>ggagagatcaaccccagcagcagcaccatcaactacgccccagcctgaaggacaagttcaccat<br>cagcagagacaacgccaagaacaccctgtacctgcagatgaacagcctgcgggccgaggacac<br>cgccgtgtactattgtgccagcctgtactacgactacggcgacgcctacgattactggggccagggca<br>cactggtgactgttagctccggcagcaccagcggctccggcaagcctggctctggcgagggcagca<br>caaaggggagatcgtgatgacacagagccctgccaccctgagcgtgtcccaggcgaaagagct<br>accctgagctgcaaggccagcagagcgtggaaagcaacgtggcctggtatcagcagaagcccg<br>gacaggctcctcgggccctgatctacagcgccagcctgagattcagcggcatccccgccaggtttag<br>cggctctggcagcggcaccgagttcacccctgacaatcagcgcctgaagatcagcggagactttgccgt<br>gtattactgccagcagtacaacaactaccccctgaccttcggagccggcaccaagctggagctgaa<br>gcctgccgagcctaagagccccgacaagacccacacctgtcccccttgtcctgcccctccagtggct<br>ggccctagcgtgttcctgttccccccaaagcccaaggataccctgatgatcgcccggacccccgaag<br>tcacatgcgtggtggtggacgtgagccacgaagaccctgaggtcaagttcaactggtacgtggacgg<br>cgtggaggtgcataatgccaagacaaagccgcgggaggagcagtacaacagcacgtaccgtgtg<br>gtcagcgtcctcaccgtcctgcaccaggactggctgaatggcaaggagtacaagtgcaaggtctcca<br>acaaagccctcccagccccatcgagaaaaccatctccaaagccaaagggcagccccgagaac<br>cacaggtgtacaccctgcccccatcccgggatgagctgaccaagaaccaggtcagcctgacctgcc<br>tggtcaaaggcttctatcccagcgacatcgccgtggagtgggagagcaatgggcagccggagaac<br>aactacaagaccacgcctcccgtgctggactccgacggctccttcttcctctacagcaagctcaccgtg<br>gacaagagcaggtggcagcaggggaacgtcttctcatgctccgtgatgcatgaggctctgcacaacc<br>actacacgcagaagagcctctccctgtctccgggtaaaaaagatcccaaattttgggtgctggtggtg<br>gttggtggagtcctggccttgctatagcttgctagtaacagtggcctttattattttctgggtgaggagtaaga<br>ggagcaggctcctgcacagtgactacatgaacatgactccccgccgcccccgggcccacccgcaag<br>cattaccagccctatgccccaccacgcgacttcgcagcctatcgctccctgagagtgaagttcagcag<br>gagcgcagacgcccccgcgtaccagcagggccagaaccagctctataacgagctcaatctaggac<br>gaagagaggagtacgatgtttggacaagagacgtggccgggaccctgagatgggggaaagcc<br>gagaaggaagaaccctcaggaaggcctgtacaatgaactgcagaaagataagatggcggaggc<br>ctacagtgagattgggatgaaaggcgagcgccggaggggcaaggggcacgatggcctttaccagg<br>gtctcagtacagccaccaaggacacctacgacgcccttcacatgcaggccctgccccctcgctga | Construct IX<br>IX_MP71-<br>hBCMA-VH-<br>WL-<br>VL_IgG1_CD28_CD3z |
| 87 | atggatttccaggtgcagatcttcagcttcctgctgatctccgccagcgtgatcatgagccgcgagatcg<br>tgatgacacagagccctgccaccctgagcgtgtcccaggcgaaagagctaccctgagctgcaag<br>gccagcagagcgtggaaagcaacgtggcctggtatcagcagaagcccggacaggctcctcggg<br>ccctgatctacagcgccagcctgagattcagcggcatccccgccaggtttagcggctctggcagcgg<br>caccgagttcaccctgacaatcagcagctgcagagcgaggactttgccgtgtattactgccagcagt<br>acaacaactaccccctgaccttcggagccggcaccaagctggagctgaaggggcagcaccagcgg<br>ctccggcaagcctggctctggcgagggcagcacaaagggagaggtgcagctggtggaatctggcg<br>gaggactggtgcagcctggcggctctctgagactgtcttgtgccgccagcggcttcaccttcagcggt<br>actggtttagctgggtgcgccaggccccctggcaagggactcgtgtgggtgggagagatcaaccca<br>gcagcagcaccatcaactacgccccagcctgaaggacaagttcaccatcagcagagacaacgc<br>caagaacaccctgtacctgcagatgaacagcctgcgggccgaggacaccgccgtgtactattgtgc<br>cagcctgtactacgactacggcgacgcctacgattactggggccagggcacactggtgactgttagct<br>ccgctgccgagcctaagagccccgacaagacccacacctgtcccccttgtcctgcccctccagtggct<br>ggccctagcgtgttcctgttccccccaaagcccaaggataccctgatgatcgcccggacccccgaag<br>tcacatgcgtggtggtggacgtgagccacgaagaccctgaggtcaagttcaactggtacgtggacgg<br>cgtggaggtgcataatgccaagacaaagccgcgggaggagcagtacaacagcacgtaccgtgtg<br>gtcagcgtcctcaccgtcctgcaccaggactggctgaatggcaaggagtacaagtgcaaggtctcca<br>acaaagccctcccagccccatcgagaaaaccatctccaaagccaaagggcagccccgagaac<br>cacaggtgtacaccctgcccccatcccgggatgagctgaccaagaaccaggtcagcctgacctgcc<br>tggtcaaaggcttctatcccagcgacatcgccgtggagtgggagagcaatgggcagccggagaac<br>aactacaagaccacgcctcccgtgctggactccgacggctccttcttcctctacagcaagctcaccgtg<br>gacaagagcaggtggcagcaggggaacgtcttctcatgctccgtgatgcatgaggctctgcacaacc<br>actacacgcagaagagcctctccctgtctccgggtaaaaaagatcccaaattttgggtgctggtggtg<br>gttggtggagtcctggccttgctatagcttgctagtaacagtggcctttattattttctgggtgaggagtaaga<br>ggagcaggctcctgcacagtgactacatgaacatgactccccgccgcccccgggcccacccgcaag<br>cattaccagccctatgccccaccacgcgacttcgcagcctatcgctccctgagagtgaagttcagcag<br>gagcgcagacgcccccgcgtaccagcagggccagaaccagctctataacgagctcaatctaggac<br>gaagagaggagtacgatgtttggacaagagacgtggccgggaccctgagatgggggaaagcc<br>gagaaggaagaaccctcaggaaggcctgtacaatgaactgcagaaagataagatggcggaggc<br>ctacagtgagattgggatgaaaggcgagcgccggaggggcaaggggcacgatggcctttaccagg<br>gtctcagtacagccaccaaggacacctacgacgcccttcacatgcaggccctgccccctcgctga | Construct X<br>X_MP71-<br>hBCMA-VL-<br>WL-<br>VH_IgG1_CD28_CD3z |

| | | |
|---|---|---|
| 88 | atggatttccaggtgcagatcttcagcttcctgctgatctccgccagcgtgatcatgagccgcgaagtgc<br>agctggtcgaatctggaggaggcctggttcagcctggtggcagcctaggctctcttgtgcagcctctgg<br>ctttaccttctcacggtattggttcagctgggtgagacaggctccagggaaaggtctggtgtgggtaggg<br>gagatataaaccccagcagcagcacgatcaactatgctccgtcactgaaagacaagttcaccatttccc<br>gcgataatgccaagaacactctctacttgcagatgaatt cccttcgcgccgaggatacagcggtgtact<br>actgcgccagtctgtactacgactatggggacgcatacgactattggggacaaggcacactggtgac<br>tgttagctccggcagcaccagcggctccggcaagcctggctctggcgagggcagcacaaagggag<br>agatcgtgatgacccagtctcctgctaccctgagcgtttctcccggtgaaagggccacactcagctgca<br>aagcctctcaaagcgtggagagcaatgtcgcctggtatcgcctggtatcagcagaaacctggccaagctccgagag<br>cactgatctattccgcgtcattgcgcttttccggcataccagcacggtttagtggctcagggagtgggact<br>gagttcactctgacgattagctcccttcagtcagaggatttcgccgtgtactactgtcagcagtacaaca<br>actatcccctcacattcggagctggaaccaagctggaactgaagcctgccgagcctaagagcccg<br>acaagacccacacctgtccccccttgtcctgcccctccagtggctggcccagcgtgttcctgttccccc<br>aaagcccaaggatacccttgatgatcgcccggacccccgaagtcacatcgcgtggtggtggacgtgag<br>ccacgaagaccctgaggtcaagttcaactggtacgtggacggcgtggaggtgcataatgccaagac<br>aaagccgcggaggagcagtacaacagcacgtaccgtgtggtcagcgtcctcaccgtcctgcacc<br>aggactggctgaatggcaaggagtacaagtgcaaggtctccaacaaagcccctccaagcccccatc<br>gagaaaaccatctccaaagccaaagggcagccccgagaaccacaggtgtacaccctgcccccat<br>cccgggatgagctgaccaagaaccaggtcagcctgacctgcctggtcaaaggcttctatcccagcg<br>acatcgccgtggagtgggagagcaatgggcagccggagaacaactacaagaccacgcctcccgt<br>gctggactccgacggctccttcttcctctacagcaagctcaccgtggacaagagcaggtggcagcag<br>gggaacgtcttctcatgctccgtgatgcatgaggctctgcacaaccactacacgcagaagagcctctc<br>cctgtctccgggtaaaaaagatcccaaattttgggtgctggtggtggttggtggagtcctggcttgctata<br>gcttgctagtaacagtggcctttattattttctgggtgaggagtaagaggagcaggctcctgcacagtga<br>ctacatgaacatgactccccgccgccccgggcccacccgcaagcattaccagccctatgccccacc<br>acgcgacttcgcagcctatcgctccctgagagtgaagttcagcaggagcgcagacgcccccgcgt<br>ccagcagggccagaaccagctctataacgagctcaatctaggacgaagagaggagtacgatgttttt<br>ggacaagagacgtggccgggaccctgagatggggggaaagccgagaaggaagaaccctcagg<br>aaggcctgtacaatgaactgcagaaagataagatggcggaggcctacagtgagattgggatgaaa<br>ggcgagcgccggaggggcaaggggcacgatggcctttacccaggggtctcagtacagccaccaagg<br>acacctacgacgcccttcacatgcaggccctgccccctcgctga | Construct XI<br>XI_MP71-<br>hBCMA-VH-<br>WL-<br>VL_IgG1_CD28_CD3z_no_opt |
| 89 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtgcgccaggcccctggcaagggactcgtgtgggtg<br>ggagagatcaaccccagcagcagcaccatcaactacgccccagcctgaaggacaagttccaccat<br>cagcagagacaacgccaagaacaccctgtacctgcagatgaacagcctgcgggccgaggacac<br>cgccgtgtactattgtgccagcctgtactacgactacggcgacgcctacgattactgggccagggca<br>cactggtgactgttagctccggcagcaccagcggctccggcaagcctggctctggcgagggcagca<br>caaagggagagatcgtgatgacacagagccctgccaccctgagcgtgtcccaggcgaaagagct<br>accctgagctgcaaggccagcagagcgtggaaagcaacgtggcctggtatcagcagaagcccg<br>gacaggctcctcgggccctgatctacagcgccagcctgagattcagcggcatccccgccaggttttcc<br>ggatctggcagcggcaccgagttcaccctgacaatcagcagcctgcagagcgaggactttgccgtgt<br>attactgccagcagtacaacaactacccccctgaccttcggagccggcaccaagctggagctgaagg<br>agagcaagtacggcccctcctgcccccccttgccctgccccgagttcgagggcggaccagcgtgtt<br>cctgttccccccaagcccaaggacacccctgatgatcagccggacccccgaggtgacctgcgtggt<br>ggtggacgtgagccaggaagatccggaggtccagttcaattggtacgtggacggcgtggaagtgca<br>caacgccaagaccaagcccagagaggaacagttcaacagcacctaccgggtggtgtctgtgctga<br>ccgtgctgcaccaggactggctgaacggcaaagaatacaagtgcaaggtgtccaacaagggcctg<br>cccagcagcatcgaaaagaccatcagcaaggccaagggccagcctcgcgagccccaggtgtaca<br>ccctgcctccctcccaggaagagatgaccaagaaccaggtgtccctgacctgcctggtgaaggcttc<br>taccccagcgacatcgccgtggagtgggagagcaacggccagcctgagaacaactacaagacc<br>accccctccgtgctggacagcgacggcagcttcttcctctacagccggctgaccgtggacaagagcc<br>ggtggcaggaaggcaacgtctttagctgcagcgtgatgcacgaggccctgcacaaccactacaccc<br>agaagagcctgagcctgtccctgggcaagtttttgggtgctggtggtggttcctggcttgctat<br>agcttgctagtaacagtggcctttattattttctgggtgaggagtaagaggagcaggctcctgcacagtg<br>actacatgaacatgactccccgtcgacccgggcccacccgcaagcattaccagccctatgccccac<br>cacgcgacttcgcagcctatcgctccctgagagtgaagttcagcaggagcgcagacgcccccgcgt<br>accagagggccagaaccagctctataacgagctcaatctaggacgaagagaggagtacgatgtt<br>tggacaagagacgtggccgggaccctgagatggggggaaagccgagaaggaagaaccctcagg<br>aaggcctgtacaatgaactgcagaaagataagatggcggaggcctacagtgagattgggatgaaa<br>ggcgagcgccggaggggcaaggggcacgatggcctttacccaggggtctcagtacagccaccaagg<br>acacctacgacgcccttcacatgcaggccctgccccctcgctga | Construct XII<br>XII_new_cuts_MP71-<br>hBCMA-<br>VH-WL-<br>VL_IgG4_CD28_CD3z |
| 90 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtgcgccaggcccctggcaagggactcgtgtgggtg<br>ggagagatcaaccccagcagcagcaccatcaactacgccccagcctgaaggacaagttccaccat<br>cagcagagacaacgccaagaacaccctgtacctgcagatgaacagcctgcgggccgaggacac<br>cgccgtgtactattgtgccagcctgtactacgactacggcgacgcctacgattactgggccagggca<br>cactggtgactgttagctccggcagcaccagcggctccggcaagcctggctctggcgagggcagca<br>caaagggagagatcgtgatgacacagagccctgccaccctgagcgtgtcccaggcgaaagagct<br>accctgagctgcaaggccagcagagcgtggaaagcaacgtggcctggtatcagcagaagcccg<br>gacaggctcctcgggccctgatctacagcgccagcctgagattcagcggcatccccgccaggttttcc<br>ggatctggcagcggcaccgagttcaccctgacaatcagcagcctgcagagcgaggactttgccgtgt<br>attactgccagcagtacaacaactacccccctgaccttcggagccggcaccaagctggagctgaagg<br>agagcaagtacggcccctcctgcccccccttgcctggccagcctcgcgagccccaggtgtacccct<br>gcctcccctcccaggaagagatgaccaagaaccaggtgtccctgacctgcctggtgaagggcttctac<br>cccagcgacatcgccgtggagtgggagagcaacggccagcctgagaacaactacaagaccac | Construct XIII<br>XIII_new_cuts_MP71-<br>hBCMA-VH-<br>WL-<br>VL_IgG4_HI_CH3_CD28_CD3z |

|   |   |   |
|---|---|---|
| | cctcccgtgctggacagcgacgtgcagcttcttcctctacagccggctgaccgtggacaagagccggt<br>ggcaggaaggcaacgtctttagctgcagcgtgatgcacgaggccctgcacaaccactacacccag<br>aagagcctgagcctgtccctgggcaagtttggggtgctggtggtggttggtggagtcctggcttgctatag<br>cttgctagtaacagtggcctttattattttctgggtgaggagtaagaggagcaggctcctgcacagtgact<br>acatgaacatgactccccgtcgacccgggccacccgcaagcattaccagccctatgccccaccac<br>gcgacttcgcagcctatcgctccctgagagtgaagttcagcaggagcgcagacgccccgcgtacc<br>agcagggccagaaccagctctataacgagctcaatctaggacaagagaggagtacgatgttttgg<br>acaagagacgtggccgggaccctgagatgggggaaagccgagaaggaagaaccctcaggaa<br>ggcctgtacaatgaactgcagaaagataagatggcggaggcctacagtgagattgggatgaaagg<br>cgagcgccggaggggcaaggggcacgatggcctttaccagggtctcagtacagccaccaaggac<br>acctacgacgccttcacatgcaggccctgcccctcgctga | |
| 91 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtcgccaggccctggcaagggactcgtgtgggtg<br>ggagagatcaaccccagcagcagcaccatcaactacgccccagcctgaaggacaagttcaccat<br>cagcagagacaacgccaagaacaccctgtacctgcagatgaacagcctgcgggccgaggacac<br>cgccgtgtactattgtgccagcctgtactacgactacggcgacgcctacgattactggggccagggca<br>cactggtgactgttagctccggcagcaccagcggctccggcaagcctggctctggcgagggcagca<br>aaagggagagatcgtgatgacacagagccctgccaccctgagcgtgtcccaggcgaaagagct<br>accctgagctgcaaggccagcagagcgtggaaagcaacgtggcctggtatcagcagaagcccg<br>gacaggctcctcgggcctgatctacagcgccagcctgagattcagcggcatcccgccaggttttcc<br>ggatctggcagcggcaccgagttcaccctgacaatcagcagcctgcagagcgaggactttgccgtgt<br>attactgccagcagtacaacaactacccctgaccttcggagccggcaccaagctggagctgaagg<br>agagcaagtacggccctccctgccccccttgcccttttgggtgctggtggtggttggtggagtcctggct<br>tgctatagcttgctagtaacagtggcctttattattttctgggtgaggagtaagaggagcaggctcctgca<br>cagtgactacatgaacatgactccccgtcgacccgggccacccgcaagcattaccagccctatgcc<br>ccaccacgcgacttcgcagcctatcgctccctgagagtgaagttcagcaggagcgcagacgccccc<br>gcgtaccagcagggccagaaccagctctataacgagctcaatctaggacaagagaggagtacg<br>atgttttggacaagagacgtggccgggaccctgagatgggggaaagccgagaaggaagaaccc<br>tcaggaaggcctgtacaatgaactgcagaaagataagatggcggaggcctacagtgagattgggat<br>gaaaggcgagcgccggaggggcaaggggcacgatggcctttaccagggtctcagtacagccacc<br>aaggacacctacgacgccttcacatgcaggccctgcccctcgctga | Construct XIV<br>XIV_new_cuts_MP71-<br>hBCMA-VH-<br>WL-<br>VL_IgG4_HI_CD28_CD3z |
| 92 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtcgccaggccctggcaagggactcgtgtgggtg<br>ggagagatcaaccccagcagcagcaccatcaactacgccccagcctgaaggacaagttcaccat<br>cagcagagacaacgccaagaacaccctgtacctgcagatgaacagcctgcgggccgaggacac<br>cgccgtgtactattgtgccagcctgtactacgactacggcgacgcctacgattactggggccagggca<br>cactggtgactgttagctccggcagcaccagcggctccggcaagcctggctctggcgagggcagca<br>aaagggagagatcgtgatgacacagagccctgccaccctgagcgtgtcccaggcgaaagagct<br>accctgagctgcaaggccagcagagcgtggaaagcaacgtggcctggtatcagcagaagcccg<br>gacaggctcctcgggcccctgatctacagcgccagcctgagattcagcggcatcccgccaggtttag<br>cggctctggcagcggcaccgagttcaccctgacaatcagcagcctgcagagcgaggactttgccgt<br>gtattactgccagcagtacaacaactacccctgaccttcggagccggcaccaagctggagctgaa<br>ggctgccgagcctaagcccccgacaagacccacacctgtcctgcccctccagtggct<br>ggccctagcgtgttcctgttccccccaaagcccaaggatacccctgatgatcgcccggaccccgaag<br>tcacatgcgtggtggtggacgtgagccacgaagaccctgaggtcaagttcaactggtacgtggacgg<br>cgtggaggtgcataatgccaagacaaagccgcgggaggagcagtacaacagcacgtaccgtgtg<br>gtcagcgtcctcaccgtcctgcaccaggactggctgaatggcaaggagtacaagtgcaaggtctcca<br>acaaagccctcccagccccatcgagaaaaccatctccaaagccaaagggcagccccgagaac<br>cacaggtgtacaccctgccccatcccgggatgagctgaccaagaaccaggtgtccctgacctgcct<br>cgtgaagggcttctacccctccgatatcgccgtggaatgggagagcaatggccagcccgagaacaa<br>ctacaagaccaccccctgtgctggacgaacggctcattcttcctgtacagcaagctgacagtgg<br>acaagagccggtggcagcaggggaacgtgttcagctgcagcgtgatgcacgaggctctgcacaac<br>cactacacccagaagtccctgagcagcctgagcccaggcaagaagatctacatctgggcccctctg<br>gccggcacctgtgcgtgctgctgctgtctcgtgatcacactgtactgcaagcggggcagaaagaa<br>gctgctgtacatcttcaagcagccctttcatgcggccgtgcagacccaccaggaagaggacggctgc<br>tcctgcagattccccgaggaagaagaaggcggctgcgagctgctgcgcgtgaagttttctagaagcg<br>ccgacgcccctgcctaccagcaggggcagaaccagctgtacaacgagctgaacctgggcagacg<br>ggaagagtacgacgtgctggataagcggagaggccgggaccctgagatgggcggcaagcctaga<br>agaaagaaccccaggaaggcctgtataacgaactgcagaaagacaagatggccgaggcctac<br>agcgagatcggaatgaaggcgagcggagaaggcaaggcacgatggactgtaccaggg<br>cctgagcaccgccaccaaggacacctatgacgccctgcacatgcaggctctgcccccaga | Construct XV<br>XV_MP71-<br>hBCMA-VH-<br>WL-<br>VL_IgGdelta_CD8_4-<br>1BB_CD3z |
| 93 | atggatttccaggtgcagatcttcagcttcctgctgatctccgccagcgtgatcatgagccgcgagatcg<br>tgatgacacagagccctgccaccctgagcgtgtcccaggcgaaagagctaccctgagctgcaag<br>gccagcagagcgtggaaagcaacgtggcctggtatcagcagaagcccaggctcctcgg<br>ccctgatctacagcgccagcctgagattcagcggcatcccgccaggtttagcggctctggcagcgg<br>caccgagttcaccctgacaatcagcagcctgcagagcgaggactttgccgtgtattactgccagcagt<br>acaacaactacccctgaccttcggagccggcaccaagctggagctgaagggcagcaccagcgg<br>ctccggcaagcctggctctggcgagggcagcacaaagggagaggtgcagctggtggaatctggcg<br>gaggactggtgcagcctggcggctctctgagactgtcttgtgccgccagcggcttcaccttcagccggt<br>actggtttagctgggtcgccaggccctggcaagggactcgtgtgggtgggagagatcaaccca<br>gcagcagcaccatcaactacgccccagcctgaaggacaagttcaccatcagcagagacaacgc<br>caagaacaccctgtacctgcagatgaacagcctgcgggccgaggacaccgccgtgtactattgtgc<br>cagcctgtactacgactacggcgacgcctacgattactggggccagggcacactggtgactgttagct<br>cccctgccgagcctaagagccccgacaagacccacacctgtcccccttgtcctgcccctccagtggct | Construct XVI<br>XVI_MP71-<br>hBCMA-VL-<br>WL-<br>VH_IgGdelta_CD8_4-<br>1BB_CD3z |

```
   ggccctagcgtgttcctgttcccccaaagcccaaggatacctgatgatcgcccggaccccgaag
   tcacatgcgtggtggtggacgtgagccacgaagaccctgaggtcaagttcaactggtacgtggacgg
   cgtggaggtgcataatgccaagacaaagccgcgggaggagcagtacaacagcacgtaccgtgtg
   gtcagcgtcctcaccgtcctgcaccaggactggctgaatggcaaggagtacaagtgcaaggtctcca
   acaaagccctcccagccccatcgagaaaaccatctccaaagccaaagggcagccccgagaac
   cacaggtgtacaccctgccccatcccgggatgagctgaccaagaaccaggtgtccctgacctgcct
   cgtgaagggcttctacccctccgatatcgccgtggaatgggagagcaatggccagcccgagaacaa
   ctacaagaccaccccctgtgctggacagcgacggctcattcttcctgtacagcaagctgacagtgg
   acaagagccggtggcagcagggcaacgtgttcagctgcagcgtgatgcacgaggctctgcacaac
   cactacacccagaagtccctgagcagcctgagcccaggcaagaagatctacatctgggccctctg
   gccggcacctgtggcgtgctgctgctgtctcgtgatcacactgtactgcaagcggggcagaaagaa
   gctgctgtacatcttcaagcagcccttcatgcggcccgtgcagaccacccaggaagaggacggctgc
   tcctgcagattccccgaggaagaagaaggcggctgcgagctgctgcgcgtgaagttttctagaagcg
   ccgacgcccctgcctaccagcagggccagaaccagctgtacaacctgaacctgggcagacg
   ggaagagtacgacgtgctggataagcggagaggccgggaccctgagatgggcggcaagcctaga
   agaaagaaccccaggaaggcctgtataacgaactgcagaaagacaagatggccgaggcctac
   agcgagatcggaatgaagggcgagcggagaagaggcaagggccacgatggactgtaccaggg
   cctgagcaccgccaccaaggacacctatgacgccctgcacatgcaggctctgcccccccaga
```

| 94 | ```
atggatttccaggtgcagatcttcagcttcctgctgatctccgccagcgtgatcatgagccgcgaagtgc
agctggtcgaatctggaggaggcctggttcagcctggtggcagccttaggctctcttgtgcagcctctgg
ctttaccttctcacggtattggttcagctgggtgagacaggctccagggaaaggtctggtgtgggtaggg
gagataaaccccagcagcagcacgatcaactatgctccgtcactgaaagacaagttcaccatttccc
gcgataatgccaagaacactctctacttgcagatgaattcccttcgagccgaggatacagcggtgtact
actgcgccagtctgtactacgactatggggacgcatacgactattggggacaagcacactggtgac
tgttagctccggcagcaccagcggctccggcaaggctggctgcggaggccacaaagggag
agatcgtgatgacccagtctcctgctaccctgagcgtttctcccggtgaaaggccacactcagctgca
aagcctctcaaagcgtggagagcaatgtcgcctggtatcagcagaaacctggccaagctccgagag
cactgatctattccgcgtcattgcgcttttccggcataccagcacggtttagtggctcagggagtgggact
gagttcactctgacgattagctccttcagtcagaggatttcgccgtgtactactgtcagcagtacaaca
actatcccctcacattcggagctggaaccaagctggaactgaagcctgccgagcctaagagcccg
acaagacccacacctgtcccccttgtcctgcccctccagtggctggccctagcgtgttcctgttccccc
aaagcccaaggatacctgatgatcgcccggaccccgaagtcacatgcgtggtggtggacgtgag
ccacgaagaccctgaggtcaagttcaactggtacgtggacggcgtggaggtgcataatgccaagac
aaagccgcgggaggagcagtacaacagcacgtaccgtgtggtcagcgtcctcaccgtcctgcacc
aggactggctgaatggcaaggagtacaagtgcaaggtctccaacaaagccctcccagccccatc
gagaaaaccatctccaaagccaaagggcagccccgagaaccacaggtgtacaccctgccccat
cccgggatgagctgaccaagaaccaggtgtccctgacctgcctcgtgaagggcttctacccctccgat
atcgccgtggaatgggagagcaatggccagcccgagaaccaactacaagaccacccccctgtgct
ggacagcgacggctcattcttcctgtacagcaagctgacagtggacaagagccggtggcagcagg
gcaacgtgttcagctgcagcgtgatgcacgaggctctgcacaaccactacacccagaagtccctga
gcagcctgagcccaggcaagaagatctacatctgggcccctctggccggcacctgtggcgtgctgct
gctgtctctcgtgatcacactgtactgcaagcggggcagaaagaagctgctgtacatcttcaagcagc
ccttcatgcggcccgtgcagaccacccaggaagaggacggctgctcctgcagattccccgaggaag
aagaaggcggctgcgagctgctgcgcgtgaagttttctagaagcgccgacgcccctgcctaccagc
agggccagaaccagctgtacaacgagctgaacctgggcagacgggaagagtacgacgtgctgga
taagcggagaggccgggaccctgagatgggcggcaagcctagaagaaagaaccccaggaag
gcctgtataacgaactgcagaaagacaagatggccgaggcctacagcgagatcggaatgaaggg
cgagcggagaagaggcaagggccacgatggactgtaccagggcctgagcaccgccaccaagga
cacctatgacgccctgcacatgcaggctctgcccccccaga
``` | Construct XVII<br>XVII_MP71-<br>hBCMA-VH-<br>WL-<br>VL_IgGdelta_CD8_4-<br>1BB_CD3z_no_opt |
|---|---|---|

A further aspect of the invention relates to a vector comprising a nucleic acid molecule as described herein, preferably a viral vector, more preferably a gamma retroviral vector.

A further aspect of the invention relates to a genetically modified immune cell comprising a nucleic acid molecule or vector as described herein, and/or expressing a CAR as described herein, wherein the immune cell is preferably selected from the group consisting of a T lymphocyte or an NK cell, more preferably cytotoxic T lymphocytes.

In a preferred embodiment the genetically modified immune cell comprising a nucleic acid molecule or vector as described herein, and/or expressing a CAR as described herein, is characterised in that it is CD4+ and/or CD8+ T cell, preferably a mixture of CD4+ and CD8+ T cells. These T cell populations, and preferably the composition comprising both CD4+ and CD8+ transformed cells, show particularly effective cytolytic activity against various malignant B cells, such as multiple myeloma and B-NHL, preferably against those cells and/or the associated medical conditions described herein.

In a preferred embodiment the genetically modified immune cells comprising a nucleic acid molecule or vector as described herein, and/or expressing a CAR as described herein, are CD4+ and CD8+ T cells, preferably in a ration of 1:10 to 10:1, more preferably in a ratio of 5:1 to 1:5, 2:1 to 1:2 or 1:1. Administration of BCMA-directed modified CAR-T cells expressing the CAR described herein at the ratios mentioned, preferably at a 1:1 CD4+/CD8+ ratio, lead to beneficial characteristics during treatment of the diseases mentioned herein, for example these ratios lead to improved therapeutic response and reduced toxicity.

In a preferred embodiment the immune cells intended for administering in treatment of the diseases mentioned herein are genetically modified with a nucleic acid as described herein, encoding and expressing the anti-BCMA CAR as described herein, using a "Sleeping beauty" transposon system, in particular a sleeping beauty transposase. The Sleeping Beauty transposon system is a synthetic DNA transposon designed to introduce precisely defined DNA sequences into the chromosomes of vertebrate animals, in the context of the present invention for the purposes of modifying immune cells to express the CAR as described herein. The sleeping beauty transposons combine the advantages of viruses and naked DNA. Viruses have been evolutionarily selected based on their abilities to infect and replicate in new host cells. Simultaneously, cells have evolved major molecular defense mechanisms to protect themselves against viral infections. Avoiding the use of viruses is also important for social and regulatory reasons. The use of non-viral vectors such as the sleeping beauty system therefore avoids many, but not all, of the defenses that cells employ against vectors. For this reason, the sleeping beauty system enables particularly effective and safe genetic modification of the immune cells for administration to a patient.

A further aspect of the invention relates to an immune cell as described herein comprising a nucleic acid molecule or vector as described herein, and/or expressing a CAR as described herein, for use as a medicament in the treatment of a medical disorder associated with the presence of pathogenic B cells, such as a disease of plasma cells, memory B cells and/or mature B cells, in particular multiple myeloma or non-Hodgkin's lymphoma.

In one embodiment the medical use of the immune cell is characterised in that the medical disorder to be treated is multiple myeloma.

In one embodiment the medical use of the immune cell is characterised in that the medical disorder to be treated is non-Hodgkin's lymphoma.

In one embodiment the medical use of the immune cell is characterised in that the medical condition to be treated is associated with pathogenic mature B cells. To the knowledge of the inventors, no previous disclosure is apparent in the art that teaches that such mature B cells can be effectively targeted by a BCMA CAR-T, as described herein. Some of the tested tumor cell lines demonstrated in the examples below relate to mature B cells and are not necessarily of the memory type. In comparison, immature B cells would be those that give rise to acute lymphatic leukemia. The invention therefore also encompasses a method of treatment for the medical disorders disclosed herein, comprising the administration of a therapeutically effective amount of a CAR or a therapeutic agent comprising the CAR of the present invention to a subject in need of such treatment.

A further aspect of the invention relates to a pharmaceutical composition comprising the CAR or therapeutic agent comprising a CAR as described herein together with a pharmaceutically acceptable carrier.

DETAILED DESCRIPTION OF THE INVENTION

Multiple myeloma, also referred to as plasmocytoma, is a currently incurable B cell lymphoma which is derived from a malignantly transformed plasma cell clone. This disease constitutes the most frequent tumor of bone and bone marrow, has a median life-expectancy of seven years and is responsible for 2% of annual deaths from cancer. The malignant transformation is believed to occur in germinal centers of secondary lymphoid organs at a developmental stage where B cells have completed VDJ-rearrangement and isotype switching. The median age at diagnosis is 70 years, indicating that in many patients co-morbidities exist that preclude intensive and prolonged chemo- or radiotherapies. Moreover, allogeneic bone marrow transplantations are usually excluded for this patient cohort. The disease is characterized clinically by osteolytic lesions, hypercalcemia, hematopoietic insufficiency, amyloid deposition, renal failure, excessive antibody heavy and/or light chain production, hyper viscosity, infections, bleeding disorders. The standard of care is chemotherapy, either alone or in combination with autologous stem cell transplantation, immunomodulators such as immunomodulatory drugs (IMIDs), local irradiation, proteasome inhibitors, and for a few patients allogeneic stem cell transplantation applies. Despite intensive treatments with the aforementioned modalities, the disease usually relapses and after multiple lines of therapies primary and secondary resistances develop.

The adoptive chimeric antigen receptor (CAR)-T cell therapies described herein targeted at the B cell maturation antigen (BCMA) can overcome these limitations in multiple myeloma because BCMA is highly expressed in multiple myeloma tumor cells, but not in normal B cells or precursor B cells. Secondly, in anti-CD19 antibody or anti-CD19 CAR-T cell therapies directed against B cell non-Hodgkin's lymphoma (B-NHL) resistances occur due to antigen loss. Because treatment resistance occurs after multiple lines of chemo-/immunotherapy in these B-NHLs, alternative target structures are warranted. For mature B-NHL, BCMA is a suitable target and therefore, the anti-BCMA CAR-T cells with a high affinity can be employed therapeutically even in B-NHL as specified below.

BCMA CAR-T cell transfers are selective for the tumor-associated antigen BCMA, applicable and effective even for the elderly and after multidrug resistances have appeared. They have predictable, tolerable and manageable side effects. Autologous T cells equipped with the anti-BCMA CAR have a high affinity and avidity and recognize and destroy multiple myeloma cells while sparing normal hematopoietic cells such as T cells, B cells and their bone marrow precursors; all myeloid cells and NK cells are likewise spared. Due to autologous transfer of T cells a graft-versus-host-disease cannot occur. Memory T cell formation which is important for the prevention of a relapse can develop. Due to the high affinity and avidity of the anti-BCMA CAR-T cell, even low BCMA-expressing mature B cell NHL can be recognized, allowing for T cell activation and tumor cell killing. Such mature B-NHL entities include certain stages of follicular lymphoma, diffuse large B-cell lymphoma, mantle cell lymphoma, and chronic lymphocytic leukemia.

The anti-BCMA CAR-T cell described herein is in some embodiments applicable to multiple myeloma and B-NHL patients who are not eligible for other therapies. More specifically: i) patients with multidrug resistances, ii) patients not eligible for allogeneic stem cell transplantation, iii) patients with co-morbidities that preclude further chemotherapies, iv) aged patients who do not tolerate chemotherapies, v) the CAR is applicable for salvage therapies even after progressive disease and multiple lines of other standard of care therapies have failed, vi) it is applicable even at very low antigen density on target tumor cells, where antibodies can fail, vii) a structure of the source antibody complexed with BCMA at near atomic resolution verifies its exquisite specificity, a biosafety feature not shown for other anti-BCMA CAR-T cells, and/or vii) it is applicable as a monotherapy which is not the case for antibodies.

For other anti-BCMA CAR-T cells described in the art their reactivity has only been shown for multiple myeloma cells and patients; in contrast, our anti-BCMA CAR has an unexpectedly high sensitivity even for low BCMA expressing B-NHL cell lines. Our anti-BCMA CAR confers extremely high avidity to T cells, necessary for anti-tumor efficacy. No other anti-BCMA CAR is reported to react against mature B-NHL, diffuse large B-cell lymphoma (DLBCL), defined stages of follicular lymphoma, mantle cell lymphoma, or chronic lymphocytic leukemia. The present invention demonstrates that our anti-BCMA CAR does not confer T cell-reactivity against physiological B cells, T cells, NK cells, endothelial cells, all myeloid cell lineages and their precursors. Thus, the present invention has an unprecedented low off-target reactivity on other hematopoietic tissues. In contrast to anti-CD38 CAR-T cells, our anti-BCMA CAR has no unwanted reactivity against myeloid cell precursors.

The amino acid sequence of the scFV fragment as described previously in WO/2015/166073 and in WO/2014/068079 has been modified i) in order to allow folding and expression in context of a transmembrane receptor structure; ii) the order of the light and heavy chain fragments has been inverted, iii) the linker sequence between heavy and light chains has been lengthened. Modifications enable sufficient surface expression on T cells and still maintain proper antigen binding.

Due to the low nanomolar affinity of the original FSY IgG, which is the antibody template for the scFv-part of the CAR-T cell construct, the invention is characterised in preferred embodiments in that the anti-BCMA CAR has an unexpectedly high affinity and confers extremely high specificity and avidity to T cells. High affinity and high avidity enable CAR-T cells to i) recognize, ii) be activated against, and iii) kill tumor target cells with high, intermediate and low BCMA surface expression. None of the aforementioned anti-BCMA CARs of the prior art have proven reactivity against B-NHL other than multiple myeloma cells. Therefore, the anti-BCMA CAR of the present invention is a specific and highly active reagent against an unprecedented diversity of B-NHLs with low levels/numbers of BCMA molecules.

In combination with a retroviral vector, preferably the MP71-vector and a gamma-retrovirus expression system, an unusually high transduction rate for human T cells can be achieved.

Another distinct advantage of the present invention is the detailed knowledge of the BCMA epitope recognized by the scFv fragment of the CAR. So far, no other antibody-based invention or publication has identified a BCMA epitope. Thus, the anti-BCMA CAR as described herein exhibits a substantially higher biosafety profile and no known off-target reactivity in vivo and in vitro.

Additionally, the inventors have exchanged signaling components of our CAR construct in an easy three step cloning that allows for a modular composition of clinically applicable anti-BCMA CARs.

In an in vitro co-culture system, anti-BCMA CAR-T cells of the invention become activated upon exposure to BCMA-expressing human B-NHL and multiple myeloma tumor cell lines. These T cells then develop an effector phenotype with high level secretion of IFN-gamma, a phenotype that is predictive of a cytotoxic activity.

Pre-clinical assessment involves i) in vitro cytotoxicity testing against suitable B-NHL cell lines and primary myeloma cells from patients, ii) in vivo testing of anti-BCMA CAR activity against xenotransplanted B-NHLs and multiple myeloma cell lines.

In the human setting in vivo, myeloma patients with the following characteristics are assessed via clinical phase I study: i) patients with multidrug resistances, ii) patients not eligible for allogeneic stem cell transplantation, iii) patients with co-morbidities that preclude further chemotherapies, iv) aged patients who do not tolerate chemotherapies, v) patients for salvage therapies after progressive disease has appeared, vi) patients where multiple lines of other standard of care therapies have failed, vii) patients with progressive disease after autologous stem cell transplantation, viii) patients with progressive disease after allogeneic stem cell transplantation, ix) as a bridging therapy before allogeneic stem cell transplantation.

Moreover, in the human setting, B-NHL patients with diffuse large B-cell lymphoma, follicular lymphoma, chronic lymphocytic leukemia, and mantle cell lymphoma with the following characteristics are assessed in a clinical phase I study: i) patients with multidrug resistances, ii) patients not eligible for allogeneic stem cell transplantation, iii) patients with co-morbidities that preclude further chemotherapies, iv) aged patients who do not tolerate chemotherapies, v) patients for salvage therapies after progressive disease has appeared and multiple lines of other standard of care therapies have failed, vi) patients with progressive disease after autologous stem cell transplantation, vii) patients with progressive disease after allogeneic stem cell transplantation, viii) as a bridging therapy before allogeneic stem cell transplantation, ix) patients exhibiting escape variants or mutants of CD19 and/or CD20 on tumor cells, such that current antibody therapies (anti CD20, Rituximab, anti CD19, Oletuzumab, BITE CD19/CD3, Blimatumomab) or anti-CD19 CAR therapies have lost/downregulated their target structures and become ineffective.

An additional and surprising aspect of the invention is an improved stability of the CAR as disclosed herein. The CAR polypeptide can readily be stored for extended periods under appropriate conditions without any loss of binding affinity.

Chimeric Antigen Receptors:

CARs are composed of an extracellular ectodomain derived from an antibody and an endodomain comprising signaling modules derived from T cell signaling proteins. In a preferred embodiment, the ectodomain preferably comprises variable regions from the heavy and light chains of an immunoglobulin configured as a single-chain variable fragment (scFv). The scFv is preferably attached to a hinge region that provides flexibility and transduces signals through an anchoring transmembrane moiety to an intracellular signaling domain. The transmembrane domains originate preferably from either CD8α or CD28. In the first generation of CARs the signaling domain consists of the zeta chain of the TCR complex. The term "generation" refers to the structure of the intracellular signaling domains. Second generation CARs are equipped with a single costimulatory domain originated from CD28 or 4-1BB. Third generation CARs already include two costimulatory domains, e.g. CD28, 4-1 BB, ICOS or OX40, CD3 zeta. The present invention preferably relates to a second or third generation CAR.

In various embodiments, genetically engineered receptors that redirect cytotoxicity of immune effector cells toward B cells are provided. These genetically engineered receptors referred to herein as chimeric antigen receptors (CARs). CARs are molecules that combine antibody-based specificity for a desired antigen (e.g., BCMA) with a T cell receptor-activating intracellular domain to generate a chimeric protein that exhibits a specific anti-BCMA cellular immune activity. As used herein, the term, "chimeric," describes being composed of parts of different proteins or DNAs from different origins.

CARs contemplated herein, comprise an extracellular domain (also referred to as a binding domain or antigen-binding domain) that binds to BCMA, a transmembrane domain, and an intracellular domain, or intracellular signaling domain. Engagement of the anti-BCMA antigen binding domain of the CAR with BCMA on the surface of a target cell results in clustering of the CAR and delivers an activation stimulus to the CAR-containing cell. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

In various embodiments, a CAR comprises an extracellular binding domain that comprises a humanized BCMA-specific binding domain; a transmembrane domain; one or more intracellular signaling domains. In particular embodiments, a CAR comprises an extracellular binding domain that comprises a humanized anti-BCMA antigen binding fragment thereof; one or more spacer domains; a transmembrane domain; one or more intracellular signaling domains.

The "extracellular antigen-binding domain" or "extracellular binding domain" are used interchangeably and provide a CAR with the ability to specifically bind to the target antigen of interest, BCMA. The binding domain may be derived either from a natural, synthetic, semi-synthetic, or recombinant source. Preferred are scFV domains.

"Specific binding" is to be understood as via one skilled in the art, whereby the skilled person is clearly aware of various experimental procedures that can be used to test binding and binding specificity. Methods for determining equilibrium association or equilibrium dissociation constants are known in the art. Some cross-reaction or background binding may be inevitable in many protein-protein interactions; this is not to detract from the "specificity" of the binding between CAR and epitope. "Specific binding" describes binding of an anti-BCMA antibody or antigen binding fragment thereof (or a CAR comprising the same) to BCMA at greater binding affinity than background binding. The term "directed against" is also applicable when considering the term "specificity" in understanding the interaction between antibody and epitope.

An "antigen (Ag)" refers to a compound, composition, or substance that can stimulate the production of antibodies or a T cell response in an animal. In particular embodiments, the target antigen is an epitope of a BCMA polypeptide. An "epitope" refers to the region of an antigen to which a binding agent binds. Epitopes can be formed both from contiguous amino acids or noncontiguous amino acids juxtaposed by tertiary folding of a protein.

"Single-chain Fv" or "scFv" antibody fragments comprise the VH and VL domains of antibody, wherein these domains are present in a single polypeptide chain and in either orientation {e.g., VL-VH or VH-VL). Generally, the scFv polypeptide further comprises a polypeptide linker between the VH and VL domains which enables the scFv to form the desired structure for antigen binding. In preferred embodiments, a CAR contemplated herein comprises antigen-specific binding domain that is an scFv and may be a murine, human or humanized scFv. Single chain antibodies may be cloned form the V region genes of a hybridoma specific for a desired target. In particular embodiments, the antigen-specific binding domain that is a humanized scFv that binds a human BCMA polypeptide. An illustrative example of a variable heavy chain that is suitable for constructing anti-BCMA CARs contemplated herein include, but are not limited to the amino acid sequence set forth in SEQ ID NO: 11. An illustrative example of a variable light chain that is suitable for constructing anti-BCMA CARs contemplated herein include, but is not limited to the amino acid sequence set forth in SEQ ID NO: 12.

Antibodies and Antibody Fragments:

The CAR comprises an extracellular antigen-binding domain, comprising an antibody or antibody fragment that binds a B Cell Maturation Antigen (BCMA) polypeptide. Antibodies or antibody fragments of the invention therefore include, but are not limited to polyclonal, monoclonal, bispecific, human, humanized or chimeric antibodies, single chain fragments (scFv), single variable fragments (ssFv), single domain antibodies (such as VHH fragments from nanobodies), Fab fragments, F(ab')$_2$ fragments, fragments produced by a Fab expression library, anti-idiotypic antibodies and epitope-binding fragments or combinations thereof of any of the above, provided that they retain similar binding properties of the CAR described herein, preferably comprising the corresponding CDRs, or VH and VL regions as described herein. Also mini-antibodies and multivalent antibodies such as diabodies, triabodies, tetravalent antibodies and peptabodies can be used in a method of the invention. The immunoglobulin molecules of the invention can be of any class (i.e. IgG, IgE, IgM, IgD and IgA) or subclass of immunoglobulin molecules. Thus, the term antibody, as used herein, also includes antibodies and antibody fragments comprised by the CAR of the invention, either produced by the modification of whole antibodies or synthesized de novo using recombinant DNA methodologies.

As used herein, an "antibody" generally refers to a protein consisting of one or more polypeptides substantially encoded by immunoglobulin genes or fragments of immunoglobulin genes. Where the term "antibody" is used, the term "antibody fragment" may also be considered to be referred to. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (L) (about 25 kD) and one "heavy" (H) chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively. Optionally, the antibody or the immunological portion of the antibody, can be chemically conjugated to, or expressed as, a fusion protein with other proteins.

The CARs of the invention are intended to bind against mammalian, in particular human, protein targets. The use of protein names may correspond to either mouse or human versions of a protein.

Affinities of binding domain polypeptides and CAR proteins according to the present disclosure can be readily determined using conventional techniques, e.g., by competitive ELISA (enzyme-linked immunosorbent assay), or by binding association, or displacement assays using labeled ligands, or using a surface-plasmon resonance device such as the Biacore.

Humanized antibodies comprising one or more CDRs of antibodies of the invention or one or more CDRs derived from said antibodies can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody.

See, for example, U.S. Pat. Nos. 4,816,567; 5,807,715; 5,866,692; 6,331,415; 5,530,101; 5,693,761; 5,693,762; 5,585,089; 6,180,370; 5,225,539; 6,548,640.

The term humanized antibody means that at least a portion of the framework regions, and optionally a portion of CDR regions or other regions involved in binding, of an immunoglobulin is derived from or adjusted to human immunoglobulin sequences. The humanized, chimeric or partially humanized versions of the mouse monoclonal antibodies can, for example, be made by means of recombinant DNA technology, departing from the mouse and/or human genomic DNA sequences coding for H and L chains or from cDNA clones coding for H and L chains. Humanized forms of mouse antibodies can be generated by linking the CDR regions of non-human antibodies to human constant regions by recombinant DNA techniques (Queen et al., 1989; WO 90/07861). Alternatively the monoclonal antibodies used in the method of the invention may be human monoclonal antibodies. Human antibodies can be obtained, for example, using phage-display methods (WO 91/17271; WO 92/01047).

As used herein, humanized antibodies refer also to forms of non-human (e.g. murine, camel, llama, shark) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin.

As used herein, human or humanized antibody or antibody fragment means an antibody having an amino acid sequence corresponding to that of an antibody produced by a human and/or has been made using any of the techniques for making human antibodies known in the art or disclosed herein. Human antibodies or fragments thereof can be selected by competitive binding experiments, or otherwise, to have the same epitope specificity as a particular mouse antibody. The humanized antibodies of the present invention surprisingly share the useful functional properties of the mouse antibodies to a large extent. Human polyclonal antibodies can also be provided in the form of serum from humans immunized with an immunogenic agent. Optionally, such polyclonal antibodies can be concentrated by affinity purification using amyloid fibrillar and/or non-fibrillar polypeptides or fragments thereof as an affinity reagent. Monoclonal antibodies can be obtained from serum according to the technique described in WO 99/60846.

Variable Regions and CDRs

A variable region of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies.

There are a number of techniques available for determining CDRs, such as an approach based on cross-species sequence variability (i.e., Kabat et al. Sequences of Proteins of Immunological Interest, (5th ed., 1991, National Institutes of Health, Bethesda Md.)); and an approach based on crystallographic studies of antigen-antibody complexes (Al-lazikani et al. (1997) J. Molec. Biol. 273:927-948). Alternative approaches include the IMGT international ImMunoGeneTics information system, (Marie-Paule Lefranc). The Kabat definition is based on sequence variability and is the most commonly used method. The Chothia definition is based on the location of the structural loop regions, wherein the AbM definition is a compromise between the two used by Oxford Molecular's AbM antibody modelling software (refer www.bioinf.org.uk: Dr. Andrew C. R. Martin's Group). As used herein, a CDR may refer to CDRs defined by one or more approach, or by a combination of these approaches.

In some embodiments, the invention provides an antibody or fragment thereof incorporated into a CAR, wherein said antibody or fragment thereof comprises at least one CDR, at least two, at least three, or more CDRs that are substantially identical to at least one CDR, at least two, at least three, or more CDRs of the antibody of the invention. Other embodiments include antibodies which have at least two, three, four, five, or six CDR(s) that are substantially identical to at least two, three, four, five or six CDRs of the antibodies of the invention or derived from the antibodies of the invention. In some embodiments, the at least one, two, three, four, five, or six CDR(s) are at least about 70%, 75%, 85%, 86%, 87%, 88%, 89%, 90%, 95%, 96%, 97%, 98%, or 99% identical to at least one, two or three CDRs of the antibody of the invention. It is understood that, for purposes of this invention, binding specificity and/or overall activity is generally retained, although the extent of activity may vary compared to said antibody (may be greater or lesser).

Additional Components of the CAR

In certain embodiments, the CARs contemplated herein may comprise linker residues between the various domains, added for appropriate spacing and conformation of the molecule, for example a linker comprising an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids.

Illustrative examples of linkers include glycine polymers; glycine-serine polymers; glycine-alanine polymers; alanine-serine polymers; and other flexible linkers known in the art, such as the Whitlow linker. Glycine and glycine-serine polymers are relatively unstructured, and therefore may be able to serve as a neutral tether between domains of fusion proteins such as the CARs described herein.

In particular embodiments, the binding domain of the CAR is followed by one or more "spacers" or "spacer polypeptides," which refers to the region that moves the antigen binding domain away from the effector cell surface to enable proper cell/cell contact, antigen binding and activation. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region. In one embodiment, the spacer domain comprises the CH2 and CH3 domains of IgG1 or IgG4.

The binding domain of the CAR may in some embodiments be followed by one or more "hinge domains," which play a role in positioning the antigen binding domain away from the effector cell surface to enable proper cell/cell contact, antigen binding and activation. A CAR may comprise one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8 alpha, CD4, CD28, PD1, CD 152, and CD7, which may be wild-type hinge regions from these molecules or may be altered. In another embodiment, the hinge domain comprises a PD1, CD 152, or CD8 alpha hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from the alpha, beta or zeta chain of the T-cell receptor, CD3ε, CD3ζ, CD4, CD5, CD8 alpha, CD9, CD 16, CD22, CD27, CD28, CD33, CD37, CD45, CD64, CD80, CD86, CD 134, CD 137, CD 152, CD 154, and PD1. In one embodiment, the CARs contemplated herein comprise a TM domain derived from CD8 alpha or CD28

In particular embodiments, CARs contemplated herein comprise an intracellular signaling domain. An "intracellular signaling domain," refers to the part of a CAR that participates in transducing the message of effective anti-BCMA CAR binding to a human BCMA polypeptide into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function.

CARs contemplated herein comprise one or more co-stimulatory signaling domains to enhance the efficacy, expansion and/or memory formation of T cells expressing CAR receptors. As used herein, the term, "co-stimulatory signaling domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen.

Polypeptides

"Peptide" "polypeptide", "polypeptide fragment" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring.

In various embodiments, the CAR polypeptides contemplated herein comprise a signal (or leader) sequence at the N-terminal end of the protein, which co-translationally or post-translationally directs transfer of the protein. Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Nucleic Acids

As used herein, the terms "polynucleotide" or "nucleic acid molecule" refers to messenger RNA (mRNA), RNA, genomic RNA (gRNA), plus strand RNA (RNA(+)), minus strand RNA (RNA(−)), genomic DNA (gDNA), complementary DNA (cDNA) or recombinant DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100%) sequence identity to any of the reference sequences described herein, typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

Polynucleotides can be prepared, manipulated and/or expressed using any of a variety of well-established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or MI 3 phage, and animal viruses. Examples of categories of animal viruses useful as vectors include, without limitation, retrovirus (including lentivirus), adenovirus, adeno-associated virus, herpesvirus {e.g., herpes simplex virus), poxvirus, baculovirus, papillomavirus, and papovavirus {e.g., SV40). Examples of expression vectors are pCIneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, the coding sequences of the chimeric proteins disclosed herein can be ligated into such expression vectors for the expression of the chimeric protein in mammalian cells. The "control elements" or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Vectors

In particular embodiments, a cell {e.g., an immune effector cell, such as a T cell) is transduced with a retroviral vector, e.g., a lentiviral vector, encoding a CAR. For example, an immune effector cell is transduced with a vector encoding a CAR that comprises a humanized anti-BCMA antibody or antigen binding fragment that binds a BCMA polypeptide, with a transmembrane and intracellular signaling domain, such that these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and *lenti* virus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus.

In a preferred embodiment the invention therefore relates to a method for transfecting cells with an expression vector encoding a CAR. For example, in some embodiments, the vector comprises additional sequences, such as sequences that facilitate expression of the CAR, such a promoter, enhancer, poly-A signal, and/or one or more introns. In preferred embodiments, the CAR-coding sequence is flanked by transposon sequences, such that the presence of a transposase allows the coding sequence to integrate into the genome of the transfected cell.

In some embodiments, the genetically transformed cells are further transfected with a transposase that facilitates integration of a CAR coding sequence into the genome of the transfected cells. In some embodiments the transposase is provided as DNA expression vector. However, in preferred embodiments, the transposase is provided as an expressible RNA or a protein such that long-term expression of the transposase does not occur in the transgenic cells. For example, in some embodiments, the transposase is provided as an mRNA (e.g., an mRNA comprising a cap and poly-A tail). Any transposase system may be used in accordance with the embodiments of the present invention. However, in some embodiments, the transposase is salmonid-type Tel-like transposase (SB). For example, the transposase can be the so called "Sleeping beauty" transposase, see e.g., U.S. Pat. No. 6,489,458, incorporated herein by reference. In some embodiments, the transposase is an engineered enzyme with increased enzymatic activity. Some specific examples of transposases include, without limitation, SB 10, SB 11 or SB 100× transposase (see, e.g., Mates et al, 2009, Nat Genet. 41(6):753-61, or U.S. Pat. No. 9,228,180, herein incorporated by reference). For example, a method can involve electroporation of cells with an mRNA encoding an SB 10, SB 11 or SB 100× transposase.

Sequence Variants:

Sequence variants of the claimed nucleic acids, proteins, antibodies, antibody fragments and/or CARs, for example those defined by % sequence identity, that maintain similar binding properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

The recitation "sequence identity" as used herein refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, He, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein sequence modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. Substitutions may be carried out that preferably do not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

Substitution variants have at least one amino acid residue in the antibody molecule removed and a different residue inserted in its place. The sites of greatest interest for substitutional mutagenesis include the hypervariable regions, but FR alterations are also contemplated. If such substitutions result in a change in biological activity, then more substantial changes, denominated "exemplary substitutions" in the table immediately below, or as further described below in reference to amino acid classes, may be introduced and the products screened.

Potential Amino Acid Substitutions:

| Original residue | Preferred conservative substitutions | Examples of exemplary substitutions |
|---|---|---|
| Ala (A) | Val | Val; Leu; Ile |
| Asg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn, Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citrulline and methionine sulfoxide which are neutral non-polar analogs, phenylglycine which is an aromatic neutral analog; cysteic acid which is a negatively charged analog and ornithine which is a positively charged amino acid analog. Like the naturally occurring amino acids, this list is not exhaustive, but merely exemplary of the substitutions that are well known in the art.

Genetically Modified Cells and Immune Cells

The present invention contemplates, in particular embodiments, cells genetically modified to express the CARs contemplated herein, for use in the treatment of B cell related conditions. As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably. As used herein, the term "gene therapy" refers to the introduction of extra genetic material in the form of DNA or RNA into the total genetic material in a cell that restores, corrects, or modifies expression of a gene, or for the purpose of expressing a therapeutic polypeptide, e.g., a CAR. In particular embodiments, the CARs contemplated herein are introduced and expressed in immune effector cells so as to redirect their specificity to a target antigen of interest, e.g., a BCMA polypeptide.

An "immune cell" or "immune effector cell" is any cell of the immune system that has one or more effector functions (e.g., cytotoxic cell killing activity, secretion of cytokines, induction of ADCC and/or CDC).

Immune effector cells of the invention can be autologous/autogeneic ("self") or non-autologous ("non-self," e.g., allogeneic, syngeneic or xenogeneic). "Autologous," as used herein, refers to cells from the same subject, and represent a preferred embodiment of the invention. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are autologous or allogeneic.

Illustrative immune effector cells used with the CARs contemplated herein include T lymphocytes. The terms "T cell" or "T lymphocyte" are art-recognized and are intended to include thymocytes, immature T lymphocytes, mature T lymphocytes, resting T lymphocytes, cytokine-induced killer cells (CIK cells) or activated T lymphocytes. Cytokine-induced killer (CIK) cells are typically CD3- and CD56-positive, non-major histocompatibility complex (MHC)-restricted, natural killer (NK)-like T lymphocytes. A T cell can be a T helper (Th) cell, for example a T helper 1 (ThI) or a T helper 2 (Th2) cell. The T cell can be a helper T cell (HTL; CD4+ T cell) CD4+ T cell, a cytotoxic T cell (CTL; CD8+ T cell), CD4+CD8+ T cell, CD4 CD8 T cell, or any other subset of T cells. Other illustrative populations of T cells suitable for use in particular embodiments include naive T cells and memory T cells.

For example, when reintroduced back to patients after autologous cell transplantation, the T cells modified with the CAR of the invention as described herein may recognize and kill tumor cells. CIK cells may have enhanced cytotoxic activity compared to other T cells, and therefore represent a preferred embodiment of an immune cell of the present invention.

As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro.

The present invention provides methods for making the immune effector cells which express the CAR contemplated herein. In one embodiment, the method comprises transfecting or transducing immune effector cells isolated from an individual such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before and/or after being genetically modified (i.e., transduced or transfected to express a CAR contemplated herein).

In particular embodiments, prior to in vitro manipulation or genetic modification of the immune effector cells described herein, the source of cells is obtained from a subject. In particular embodiments, the CAR-modified immune effector cells comprise T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation, antibody-conjugated bead-based methods such as MACS™ separation (Miltenyi). In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flow through centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells can be further isolated by positive or negative selection techniques. One method for use herein is cell sorting and/or selection via negative magnetic immunoadherence or flow cytometry that uses a cocktail of monoclonal antibodies directed to cell surface markers present on the cells negatively selected.

PBMC may be directly genetically modified to express CARs using methods contemplated herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells.

The immune effector cells, such as T cells, can be genetically modified following isolation using known methods, or the immune effector cells can be activated and expanded (or differentiated in the case of progenitors) in vitro prior to being genetically modified. In a particular embodiment, the immune effector cells, such as T cells, are genetically modified with the chimeric antigen receptors contemplated herein {e.g., transduced with a viral vector comprising a nucleic acid encoding a CAR) and then are activated and expanded in vitro. In various embodiments, T cells can be activated and expanded before or after genetic modification to express a CAR, using methods as described, for example, in U.S. Pat. Nos. 6,352,694; 6,534,055; 6,905,680; 6,692, 964; 5,858,358; 6,887,466; 6,905,681; 7, 144,575; 7,067, 318; 7, 172,869; 7,232,566; 7, 175,843; 5,883,223; 6,905, 874; 6,797,514; 6,867,041; and U.S. Patent Application Publication No. 20060121005.

In a further embodiment, a mixture of, e.g., one, two, three, four, five or more, different expression vectors can be used in genetically modifying a donor population of immune effector cells wherein each vector encodes a different chimeric antigen receptor protein as contemplated herein. The resulting modified immune effector cells forms a mixed population of modified cells, with a proportion of the modified cells expressing more than one different CAR proteins.

In one embodiment, the invention provides a method of storing genetically modified murine, human or humanized CAR protein expressing immune effector cells which target a BCMA protein, comprising cryopreserving the immune effector cells such that the cells remain viable upon thawing. A fraction of the immune effector cells expressing the CAR proteins can be cryopreserved by methods known in the art to provide a permanent source of such cells for the future treatment of patients afflicted with the B cell related condition. When needed, the cryopreserved transformed immune effector cells can be thawed, grown and expanded for more such cells.

Compositions and Formulations

The compositions contemplated herein may comprise one or more polypeptides, polynucleotides, vectors comprising same, genetically modified immune effector cells, etc., as contemplated herein. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions of the present invention comprise an amount of CAR-expressing immune effector cells contemplated herein. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cell effective to achieve the desired prophylactic result. Typically but not necessarily, since a prophylactic dose is used in subjects prior to or at an earlier stage of disease, the prophylactically effective amount is less than the therapeutically effective amount. The term prophylactic does not necessarily refer to a complete prohibition or prevention of a particular medical disorder. The term prophylactic also refers to the reduction of risk of a certain medical disorder occurring or worsening in its symptoms.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject {e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells may be administered. CAR expressing cell compositions may be administered multiple times at dosages within these ranges. The cells may be allogeneic, syngeneic, xenogeneic, or autologous to the patient undergoing therapy.

Generally, compositions comprising the cells activated and expanded as described herein may be utilized in the treatment and prevention of diseases that arise in individuals who are immunocompromised. In particular, compositions comprising the CAR-modified T cells contemplated herein are used in the treatment of B cell malignancies. The CAR-modified T cells of the present invention may be administered either alone, or as a pharmaceutical composition in combination with carriers, diluents, excipients, and/or with other components such as IL-2 or other cytokines or cell populations. In particular embodiments, pharmaceutical compositions contemplated herein comprise an amount of genetically modified T cells, in combination with one or more pharmaceutically or physiologically acceptable carriers, diluents or excipients.

Pharmaceutical compositions of the present invention comprising a CAR-expressing immune effector cell population, such as T cells, may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringers solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, compositions contemplated herein comprise an effective amount of CAR-expressing immune effector cells, alone or in combination with one or more therapeutic agents. Thus, the CAR-expressing immune effector cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

Therapeutic Methods

The genetically modified immune effector cells contemplated herein provide improved methods of adoptive immunotherapy for use in the treatment of B cell related conditions that include, but are not limited to immunoregulatory conditions and hematological malignancies.

In particular embodiments, compositions comprising immune effector cells comprising the CARs contemplated herein are used in the treatment of conditions associated with abnormal B cell activity, otherwise termed as a "medical disorder associated with the presence of pathogenic B cells".

As use herein, "medical disorder associated with the presence of pathogenic B cells" or "B cell malignancy" refers to a medical condition, such as cancer, that forms in B cells. In particular embodiments, compositions comprising CAR-modified T cells contemplated herein are used in the treatment of hematologic malignancies, including but not limited to B cell malignancies such as, for example, multiple myeloma (MM) and non-Hodgkin's lymphoma (NHL).

In another aspect of the present invention there is provided a CAR and CAR-T according to the invention as herein described for use in the treatment of a B-cell mediated or plasma cell mediated disease or antibody mediated disease or disorder selected from Multiple Myeloma (MM), chronic lymphocytic leukemia (CLL), Non-secretory multiple myeloma, Smoldering multiple myeloma, Monoclonal gammopathy of undetermined significance (MGUS), Solitary plasmacytoma (Bone, Extramedullar), Lymphoplasmacytic lymphoma (LPL), Waldenstrom's Macroglobulinemia, Plasma cell leukemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpasture's syndrome, Idiopathic thrombocytopenic purpura (ITP), Acute glomerulonephritis, Pemphigus and Pemphigoid disorders, and Epidermolysis bullosa acquisita; or any Non-Hodgkin's Lymphoma B-cell leukemia or Hodgkin's lymphoma (HL) with BCMA expression or any diseases in which patients develop neutralising antibodies to recombinant protein replacement therapy wherein said method comprises the step of administering to said patient a therapeutically effective amount of the CAR or CAR-T as described herein.

Multiple myeloma is a B cell malignancy of mature plasma cell morphology characterized by the neoplastic transformation of a single clone of these types of cells. These plasma cells proliferate in BM and may invade adjacent bone and sometimes the blood. Variant forms of multiple myeloma include overt multiple myeloma, smoldering multiple myeloma, plasma cell leukemia, non-secretory myeloma, IgD myeloma, osteosclerotic myeloma, solitary plasmacytoma of bone, and extramedullary Plasmacytoma.

Non-Hodgkin lymphoma encompasses a large group of cancers of lymphocytes (white blood cells). Non-Hodgkin lymphomas can occur at any age and are often marked by lymph nodes that are larger than normal, fever, and weight loss. Non-Hodgkin lymphomas can also present on extranodal sites, such as the central nervous system, mucosal tissues including lung, intestine, colon and gut. There are many different types of non-Hodgkin lymphoma. For example, non-Hodgkin's lymphoma can be divided into aggressive (fast-growing) and indolent (slow-growing) types. Although non-Hodgkin lymphomas can be derived from B cells and T-cells, as used herein, the term "non-Hodgkin lymphoma" and "B cell non-Hodgkin lymphoma" are used interchangeably. B cell non-Hodgkin lymphomas (NHL) include Burkitt lymphoma, chronic lymphocytic leukemia/small lymphocytic lymphoma (CLL/SLL), diffuse large B cell lymphoma, follicular lymphoma, immunoblastic large cell lymphoma, precursor B-lymphoblastic lymphoma, and mantle cell lymphoma. Lymphomas that occur after bone marrow or stem cell transplantation are usually B cell non-Hodgkin lymphomas.

Chronic lymphocytic leukemia (CLL) is an indolent (slow-growing) cancer that causes a slow increase in immature white blood cells called B lymphocytes, or B cells. Cancer cells spread through the blood and bone marrow, and can also affect the lymph nodes or other organs such as the liver and spleen. CLL eventually causes the bone marrow to fail. A different presentation of the disease is called small lymphocytic lymphoma and localizes mostly to secondary lymphoid organs, e.g. lymph nodes and spleen.

In one embodiment of the invention the CAR or immune cell expressing said CAR is intended for use in the treatment of an autoimmune disease, preferably an auto-antibody-dependent autoimmune disease, preferably an autoimmune disease with an inflammatory component, whereby the autoimmune disease is preferably selected from Takayasu Arteritis, Giant-cell arteritis, familial Mediterranean fever, Kawasaki disease, Polyarteritis *nodosa*, cutanous Polyarteritis

*nodosa*, Hepatitis-associated arteritis, Behcet's syndrome, Wegener's granulomatosis, ANCA-vasculitidies, Churg-Strauss syndrome, microscopic polyangiitis, Vasculitis of connective tissue diseases, Hennoch-Schönlein purpura, Cryoglobulinemic vasculitis, Cutaneous leukocytoclastic angiitis, Tropical aortitis, Sarcoidosis, Cogan's syndrome, Wiskott-Aldrich Syndrome, Lepromatous arteritis, Primary angiitis of the CNS, Thromboangiitis obliterans, Paraneoplastic ateritis, Urticaria, Dego's disease, Myelodysplastic syndrome, Eythema elevatum diutinum, Hyperimmunoglobulin D, Allergic Rhinitis, Asthma bronchiale, chronic obstructive pulmonary disease, periodontitis, Rheumatoid Arthritis, atherosclerosis, Amyloidosis, Morbus Chron, Colitis ulcerosa, Autoimmune Myositis, Diabetes mellitus, Guillain-Barre Syndrome, histiocytosis, Osteoarthritis, atopic dermatitis, periodontitis, chronic rhinosinusitis, Psoriasis, psoriatic arthritis, Microscopic colitis, Pulmonary fibrosis, glomerulonephritis, Whipple's disease, Still's disease, erythema nodosum, otitis, cryoglobulinemia, Sjogren's syndrome, Lupus erythematosus, preferably systemic lupus erythematosus (SLE), aplastic anemia, Osteomyelofibrosis, chronic inflammatory demyelinating polyneuropathy, Kimura's disease, systemic sclerosis, chronic periaortitis, chronic prostatitis, idiopathic pulmonary fibrosis, chronic granulomatous disease, Idiopathic achalasia, bleomycin-induced lung inflammation, cytarabine-induced lung inflammation, Autoimmunthrombocytopenia, Autoimmunneutropenia, Autoimmunhemolytic anemia, Autoimmunlymphocytopenia, Chagas' disease, chronic autoimmune thyroiditis, autoimmune hepatitis, Hashimoto's Thyroiditis, atropic thyroiditis, Graves disease, Autoimmune polyglandular syndrome, Autoimmune Addison Syndrome, Pemphigus vulgaris, Pemphigus *foliaceus*, Dermatitis herpetiformis, Autoimmune alopecia, Vitiligo, Antiphospholipid syndrome, Myasthenia gravis, Stiff-man syndrome, Goodpasture's syndrome, Sympathetic ophthalmia, Folliculitis, Sharp syndrome and/or Evans syndrome, in particular hay fever, periodontitis, atherosclerosis, rheumatoid arthritis, most preferably SLE.

Systemic lupus erythematosus (SLE), also known as lupus, is an autoimmune disease in which the body's immune system attacks healthy tissue in various parts of the body. Symptoms vary between people and may be mild to severe. Common symptoms include painful and swollen joints, fever, chest pain, hair loss, mouth ulcers, swollen lymph nodes, feeling tired, and a red rash which is most commonly on the face.

As used herein, the terms "individual" and "subject" are often used interchangeably and refer to any animal that exhibits a symptom of a disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a B cell malignancy, that can be treated with the gene therapy vectors, cell-based therapeutics, and methods disclosed elsewhere herein. Suitable subjects include laboratory animals (such as mouse, rat, rabbit, or guinea pig), farm animals, and domestic animals or pets (such as a cat or dog). Non-human primates and, preferably, human patients, are included. Typical subjects include human patients that have a B cell malignancy, have been diagnosed with a B cell malignancy, or are at risk or having a B cell malignancy.

As used herein "treatment" or "treating," includes any beneficial or desirable effect on the symptoms or pathology of a disease or pathological condition, and may include even minimal reductions in one or more measurable markers of the disease or condition being treated.

Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" or "prophylactic" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In one embodiment, a method of treating a B cell related condition in a subject in need thereof comprises administering an effective amount, e.g., therapeutically effective amount of a composition comprising genetically modified immune effector cells contemplated herein. The quantity and frequency of administration will be determined by such factors as the condition of the patient, and the type and severity of the patient's disease, although appropriate dosages may be determined by clinical trials.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

FIGURES

The invention is demonstrated by way of the example by the examples and figures disclosed herein. The figures provided herein represent particular embodiments of the invention and are not intended to limit the scope of the invention. The figures are to be considered as providing a further description of possible and potentially preferred embodiments that enhance the technical support of one or more non-limiting embodiments.

FIG. 1: Schematic representation of preferred CAR structures.

FIG. 2: Schematic representation of preferred CAR constructs IX, X; XI, XV, XVI, XVII.

FIG. 3: List of preferred constructs and potential combinations of the various structural elements of the CARs as described herein.

FIG. 4: Sequence comparisons between the mAb binding regions and the preferred humanized sequences employed in the present CAR.

Figure 5:
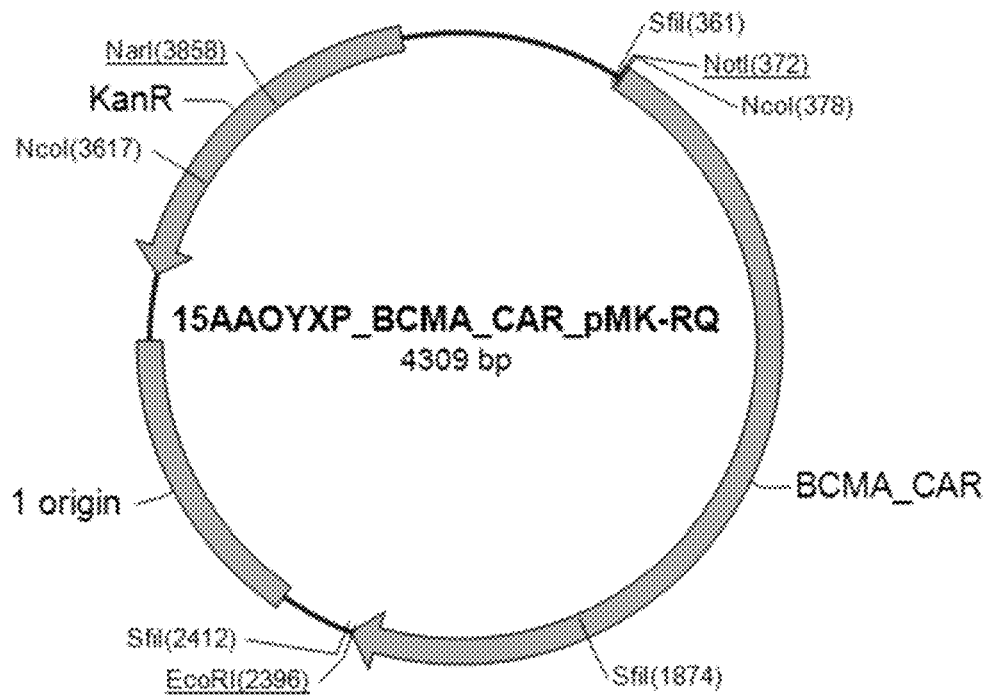

FIG. 5: GeneArt™ Plasmid with the BCMA-CAR Sequence.

Figure 6:
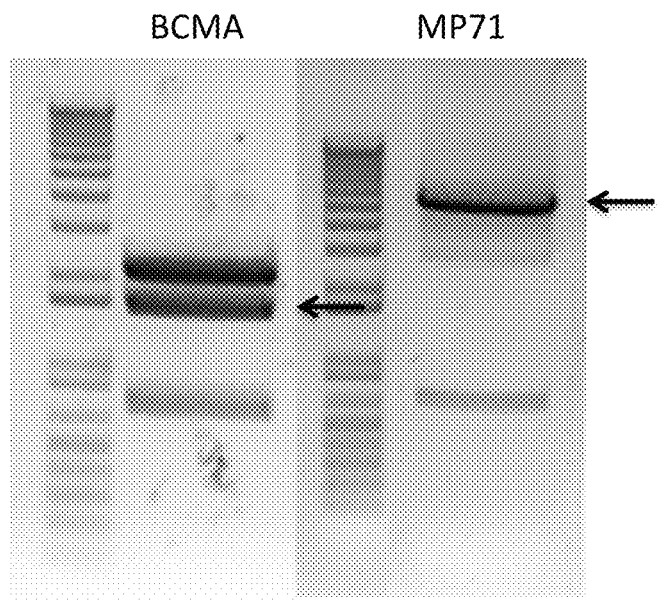

FIG. 6: Gel electrophoresis of the construct and vectors after restriction.

Figure 7:
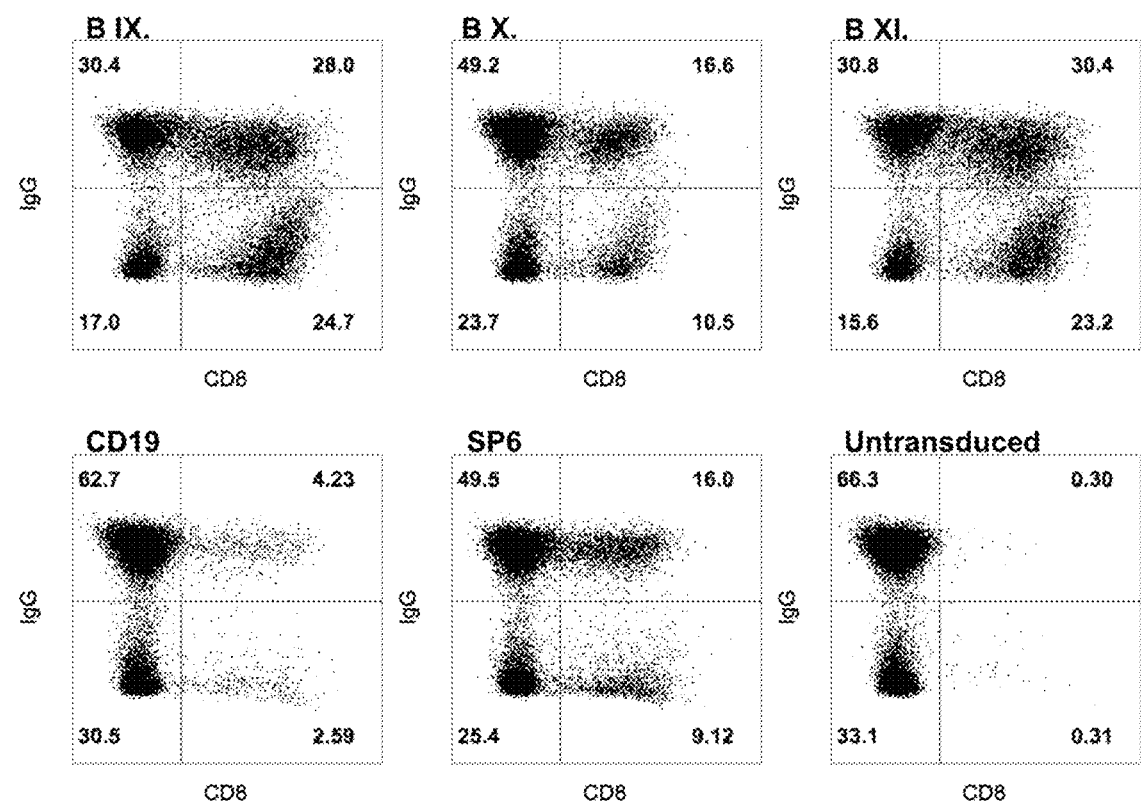

FIG. 7: Confirmation of BCMA CAR-expression on human T cells following retroviral transduction: CAR Expression, constructs IX-XII, CD19, SP6.

Figure 8:
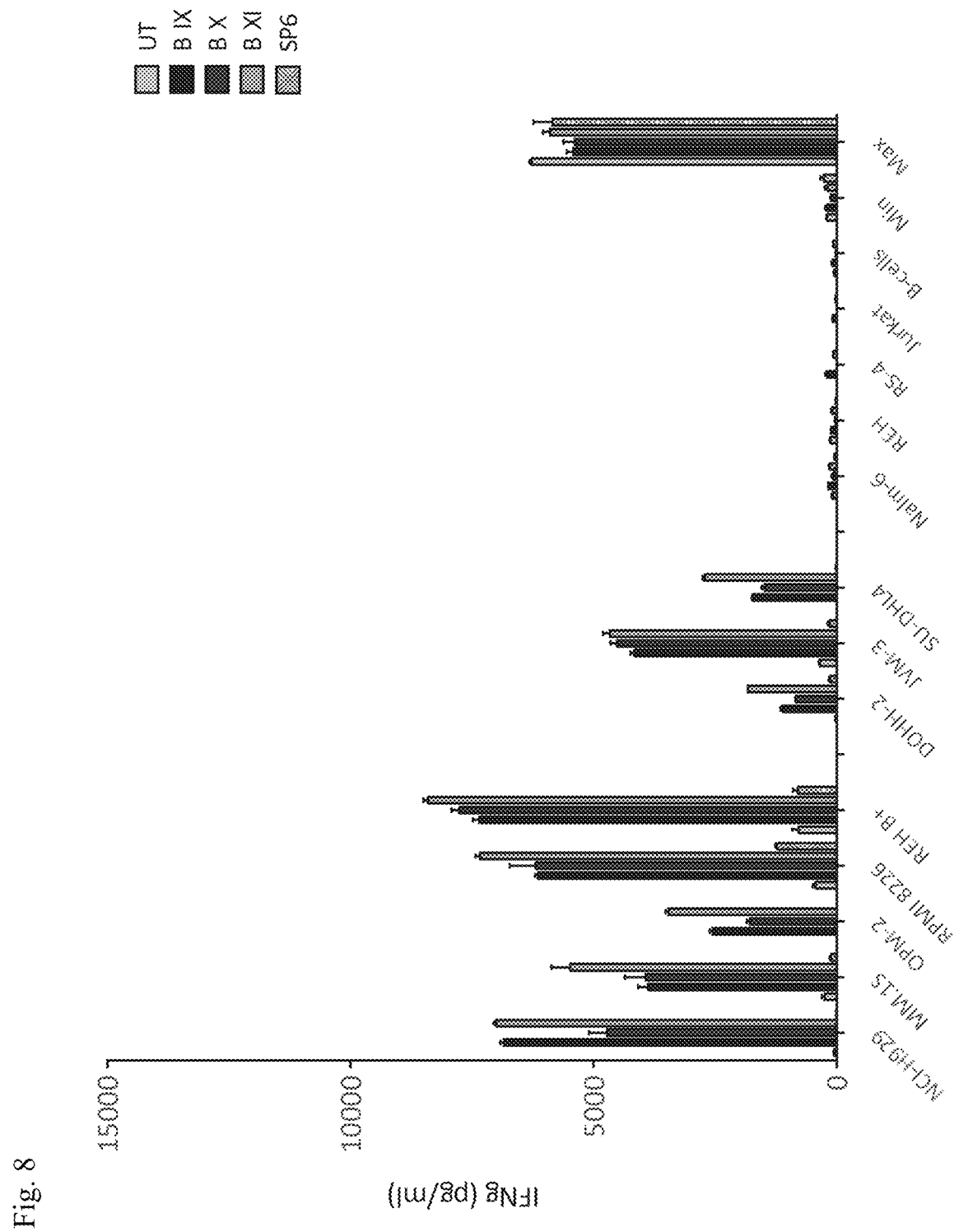

FIG. 8: Co-cultures of CAR-transduced human T cells with different target cell lines show specific T cell activation by distinct BCMA$^+$ multiple myeloma (MM) and B-NHL cell lines. Functional in vitro co-cultivation and IFN-gamma ELISA.

Figure 9:
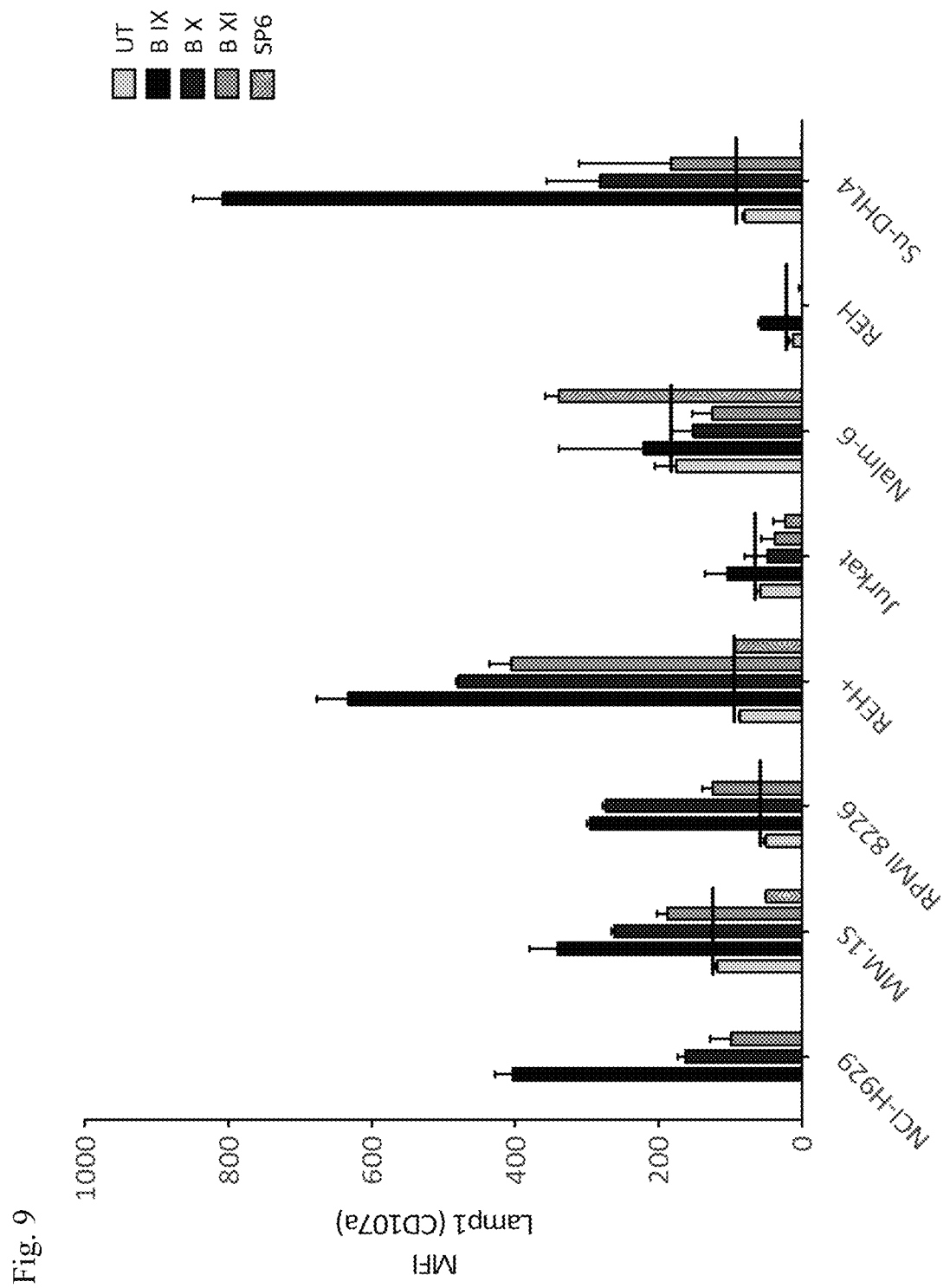

FIG. 9: CD107a (LAMP1) staining of co-cultured CAR-T cells with multiple myeloma cells: detection of activated degranulating CD8$^+$ T cells upon antigen-specific (BCMA) stimulation by flow cytometry. Functional in vitro co-cultivation and LAMP1 detection, as determined by FACS.

Figure 10:
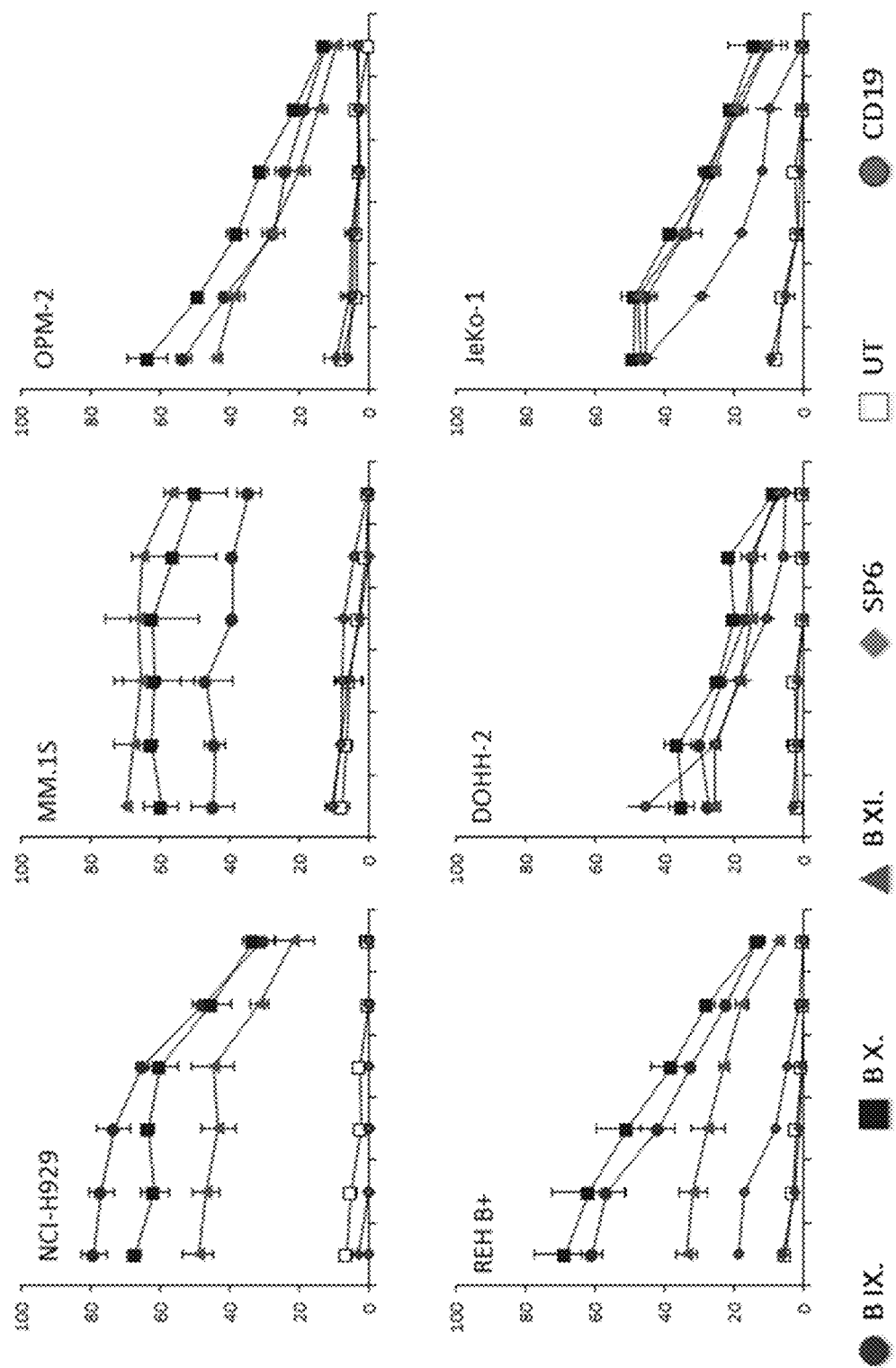
Figure 10:
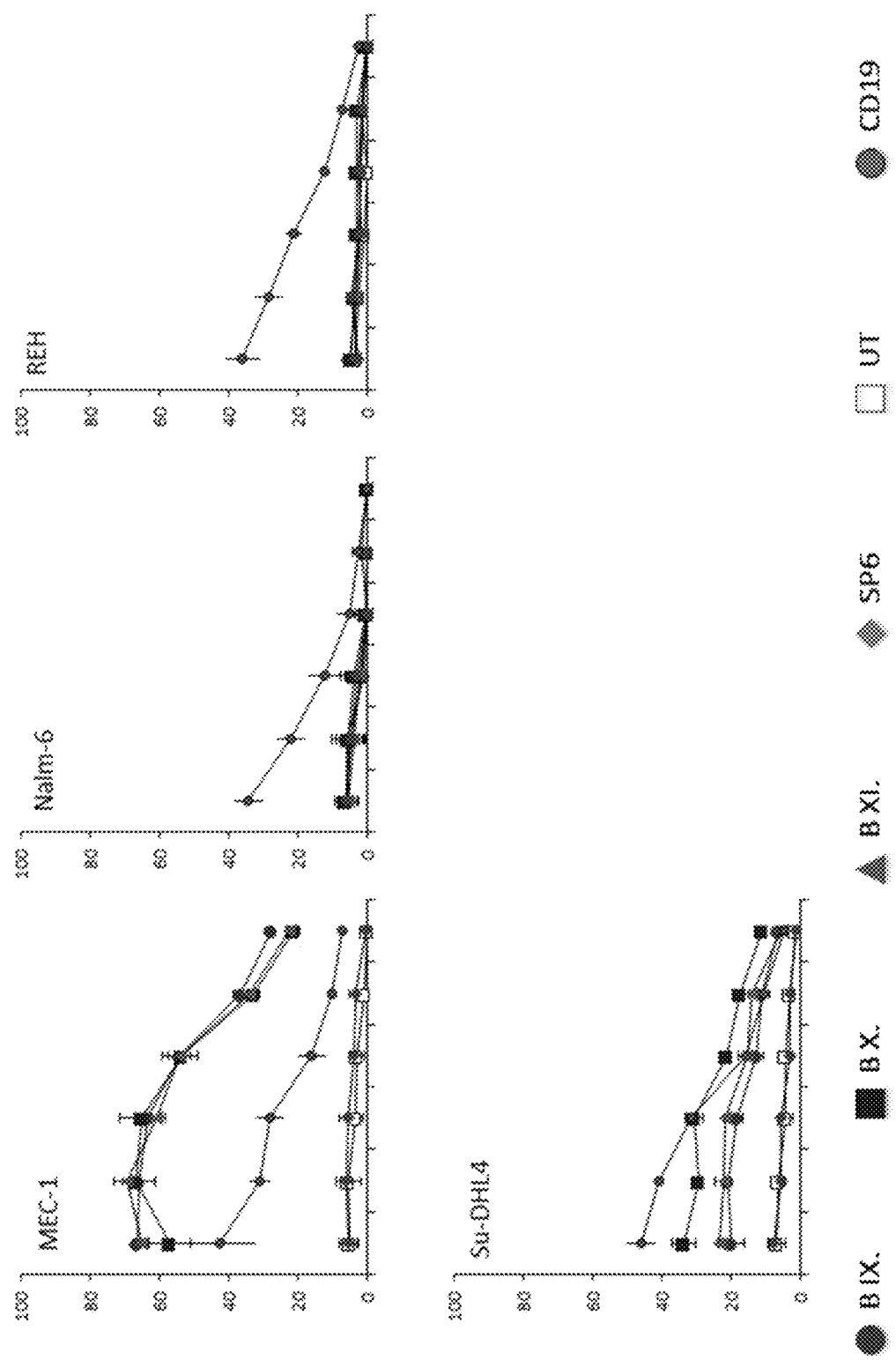

FIG. 10: Cytotoxicity assays reveal selective killing of BCMA-positive cell lines; essentially no killing was seen in BCMA-negative cell lines. Functional in vitro co-cultivation and 51Cr release assay.

FIG. 11: BCMA and CD19 expression on the cell types assessed in the functional assays. Also shown are the results of MACS-based B-Cell isolation from PBMCs, together with anti-BCMA and anti-CD19 staining.

Figure 12:
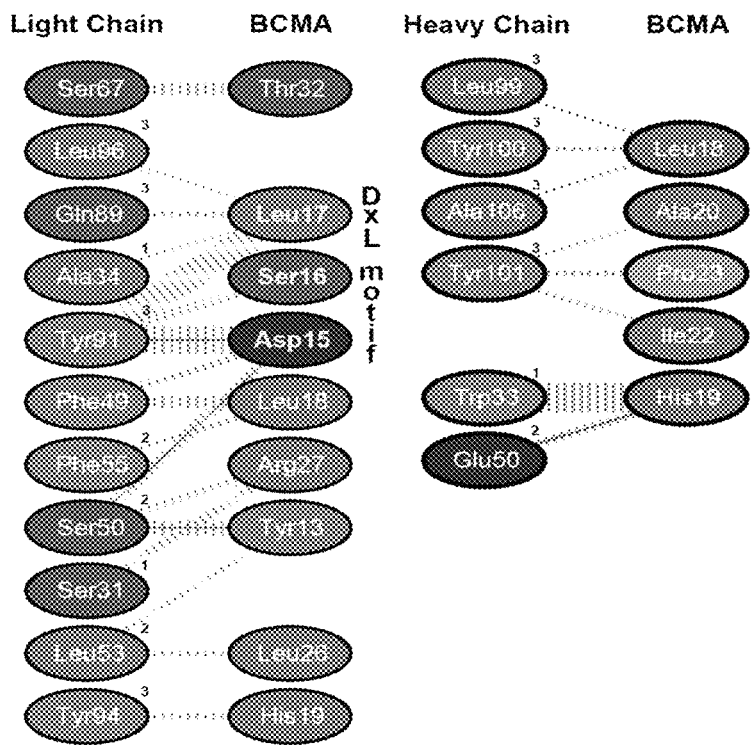

FIG. 12: Schematic representation of the binding interaction between the scFV of the CAR and the BCMA epitope.

FIG. 13: Sequence alignment of preferred humanized sequences of the HC compared to J22.9-xi.

FIG. 14: Sequence alignment of preferred humanized sequences of the LC compared to J22.9-xi.

Figure 15:
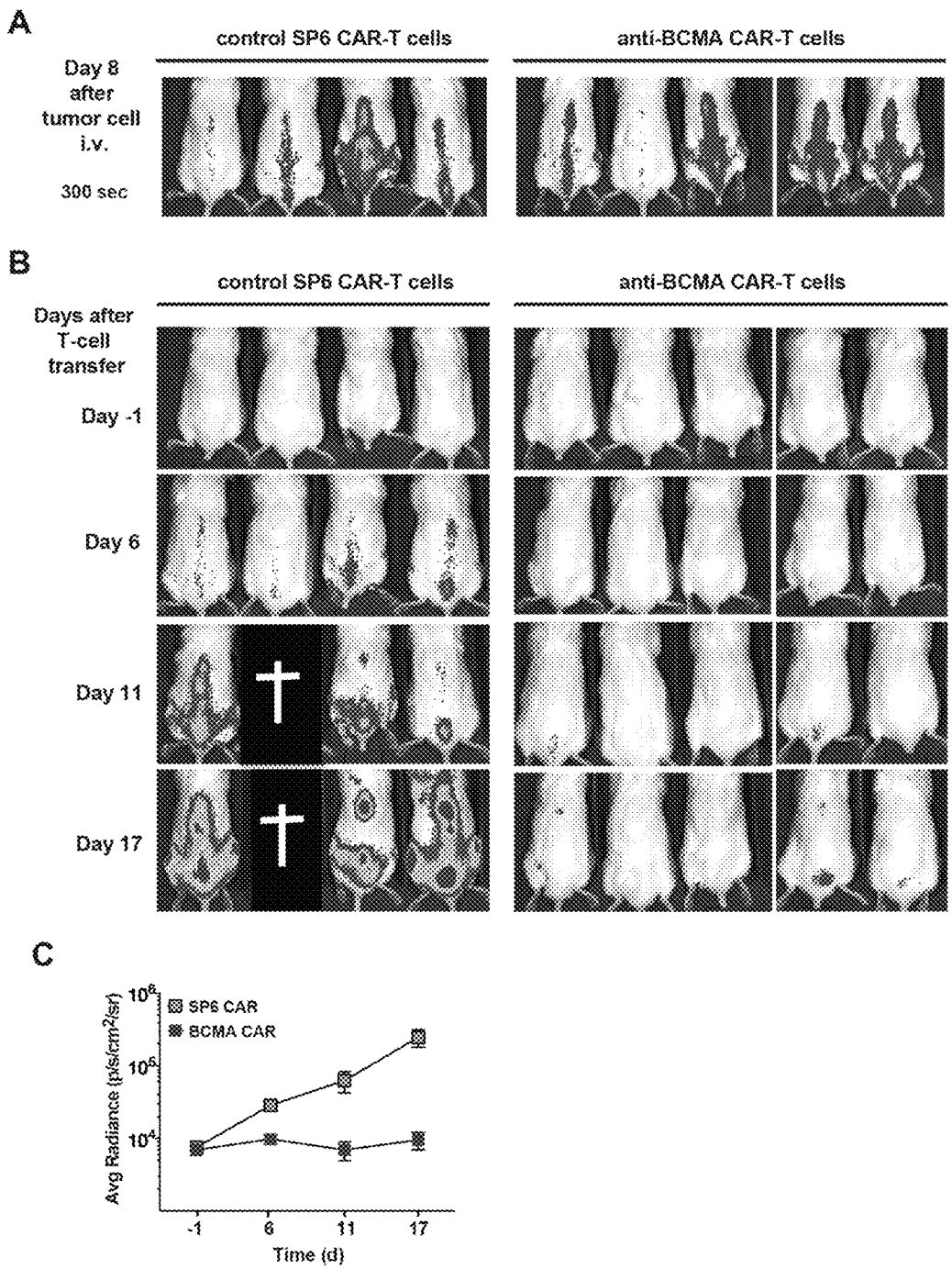

FIG. 15: BCMA redirected CAR-T cells are effective against MM tumors in a xenografted NSG mouse model. (A) Engraftment of MM tumors in a xenografted NSG mouse model. Mice were challenged by i.v. transplantation of MM.1S cells. At day 8 after tumor inoculation, tumor cell growth was visualized by IVIS imaging. To measure tumor burden, imaging was extended to 300 sec (day −1). (B) To follow treatment efficacy and to scale down bioluminescence intensity for better presentation, mice as in (A) were again imaged for 30 sec at day −1. Subsequent IVIS-exposures after CAR-T cell transfer, control SP6 CAR-T cells (n=4) and BCMA CAR-T cells (n=6), were done at 30 sec to allow better comparisons between day −1 and day 17 which has the highest intensity. White cross, animal was sacrificed because of advanced disease and animal protection laws. (C) Mean values of bioluminescence signal intensities obtained from regions of interests covering the entire body of each mouse are plotted for each group at each time point.

FIG. 16: BCMA redirected CAR-T cells are effective against B-NHL tumors in a xenografted NSG mouse model. (A) Engraftment of mantle cell lymphomas in a xenografted NSG mouse model. Mice were challenged by i.v. transplantation of 6×10$^5$ JeKo-1 cells. At day 7 after tumor inoculation, tumor cell growth was visualized by IVIS imaging. IVIS exposure, 120 sec. (B) To follow treatment efficacy and to scale down bioluminescence intensity for better presentation, mice as in (A) were again imaged for 30 sec at day 0. Subsequent IVIS-exposures after CAR-T cell transfer, control SP6 CAR-T cells (n=7) and BCMA CAR-T cells (n=7), were done for 30 sec to allow better comparisons between day 0 and day 16 which has the highest intensity. (C) Mean values of bioluminescence signal intensities obtained from regions of interests covering the entire body of each mouse are plotted for each group at each time point.

EXAMPLES

The invention is demonstrated by way of the examples disclosed herein. The examples provide technical support for and a more detailed description of potentially preferred, non-limiting embodiments of the invention. In order to demonstrate the functionality of the CAR described herein, the inventors have performed the following experiments:

- co-cultures of CAR-transduced human T cells with different target cell lines show specific T cell activation by distinct BCMA+ MM and NHL cell lines; readout was release of IFN-gamma as effector cytokine from T cells;
- cytotoxicity assays reveal selective killing of BCMA+ cell lines; essentially no killing was seen in BCMA-negative cell lines or primary cells, e.g. HUVECs (endothelial origin), HEK293 (kidney), peripheral blood B cells, peripheral blood total leukocytes, T- and B-ALL, colon carcinoma.
- CD107a staining of co-cultured CAR-T cells with multiple myeloma cells, detection of degranulating CD8+ T cells upon antigen-specific (BCMA) stimulation by flow cytometry.
- In vivo experiments relate to using a xenotransplantation NSG mouse model to generate data on i) functionality, ii) off-target reactivity, iii) T cell memory, and iv) biosafety of adoptively transferred CAR-T cells against B-NHL and myeloma cell lines. For B-NHL the cytolytic capacity of anti-BCMA CAR-T cells is compared with an established anti-CD19 CAR-T cell product.

Example 1: Cloning and Plasmid Preparation

CAR sequences were synthesized using GeneArt™ (Gene Synthesis Service). Restriction digestion of the CAR construct was carried out using NotI and EcoRI (FIG. 5). The retroviral vector MP71 was also digested with NotI and EcoRI, and subsequently dephosphorylated.

The CAR and vector were separated using gel electrophoresis (FIG. 6.) and the fragments were purified. The CAR construct was subsequently ligated into the vector (50 ng) at a ratio of 3:1. Transformation of the ligation mixture into MACH-1 was carried out (FIG. 3.). A control digest was conducted and the Mini-Preparation was sequenced. The constructs were subsequently re-transformed into MACH-1. A maxi-Preparation of the MP71-BCMA-CAR plasmid was produced.

MP71 is a single (+)-strand-RNA-Virus. Reverse-Transcriptase converts the retroviral RNA-Genome into a DNA copy. The DNA integrates as a provirus at a random position into the target genome. Through cell division the virus reproduces stably as a provirus.

Example 2: Transfection and Transduction

Day 0: Seeding HekT(293T)- or GalV-cells for virus production in 6 well plates

Day 1: Transient 3-plasmid transfection for retrovirus production (calcium phosphate transfection). Per well, 18 pg of DNA was used, in 250 mM Cacl2, 150 µl H2O, according to standard protocols. Cells are incubated for 6 h at 37° C., medium is exchanged, further incubation carried out for 48 h at 37° C.

Coating of 24-Well Non-Tissue Culture Plates with Anti-huCD3 and Anti-huCD28 Antibodies:

Prepare anti-CD3/anti-CD28-antibody solution in PBS (5 pg/ml anti-CD3, 1 pg/ml anti-CD28), 0.5 ml per well. Incubate each well with 0.5 ml antibody solution for 2 h at 37° C., replace with sterile 2% BSA-solution (in water), incubation: 30 min (37° C.). Remove BSA-solution and wash wells with 2 ml PBS.

Purification of PBMCs from 40 ml Blood (~2.5×10$^7$ PBMCs):

Prepare 12.5 ml Ficoll-Gradient medium in 2×50 ml Falcon-Tube, dilute blood with RPMI (+100 IU/ml Penicillin, Streptomycin) to 45 ml, mix and coat with 22.5 ml Blood-Medium-mixture, centrifuge (20 min, 20° C., 1800 rpm, RZB*648, G 17.9). Discard 15 ml upper phase. Transfer remainder of the upper phase with white-milky PBMC-containing intermediate phase to a new 50 ml Falcon-Tube, fill to 45 ml with RPMI (+100 IU/ml Penicillin, Streptomycin) and centrifuge. Re-suspend pellets in 45 ml RPMI (+100 IU/ml Penicillin, Streptomycin), centrifuge, combine pellets in 10-20 ml T cell medium, stain one sample with trypan blue, count cells and add cells at a concentration of 1-1.5×10$^6$ cells/ml (T-cell medium (+100 IU/ml IL-2) corresponds to 400 U/ml clinic-IL2) to the anti-CD3, anti-CD28 coated wells. Centrifuge remainder of PBMCs, suspend in freezing medium and store in Cryo tubes at −80° C.

Day 3: Transduction of PBLs

Remove and filter (0.45 µm filter) viral supernatant from Hekt- or GalV-cells. Treat stimulated PBMCs with 1.5 ml viral supernatant.

Day 4: Transduction of PBLs

Filter remaining viral supernatant (4° C.) and second supernatant from Hekt- or GalV-cells (0.45 µm). Collect 1 ml to 1.5 ml supernatant from the PBLs. Treat stimulated PBMCs with 1 ml to 1.5 ml viral supernatant and centrifuge in the CD3-/CD28-coated wells (90 min, 32° C., 2000 rpm). Final concentration of 100 IU/ml IL2 (1 ul von 400 U/µl) or 10 ng/pµl IL7 and 10 ng/µl IL15, and additionally 4 µg/ml (8 µl) Protamine sulfate. Centrifuge at 90 min 2000 rpm 32° C.

Day 7 to Day 13: Culture PBLs, treat T cell medium with fresh IL2 or IL7/IL15.

Day 13: End T-cell stimulation.

Rinse PBL-cultures from the cell culture flasks, centrifugation, re-suspend pellet in T-cell medium (+10 IU/ml IL2).

As of Day 15: Functional assays

Example 3: Functional In Vitro Testing of Anti-BCMA CAR T Cells

I. Confirmation of BCMA CAR-Expression on Human T Cells Following Retro Viral Transduction.

Evidence was obtained of folding and transport of the CAR receptor in context of human T cells; the functionality of retrovirus transduction protocol was assessed.

Human peripheral blood leukocytes were purified via a Ficoll gradient. Cells were cultured, stimulated and retrovirally transduced as described above. Following transduction, cells were further cultured in either IL-2 or IL-7/IL-15 containing medium prior to the analysis of BCMA-CAR expression.

Transduction rate and viability were assessed by flow cytometry (FACS) analysis. To detect BCMA-CAR expression, cells were stained with anti-human Ig-antibody that recognizes selectively the human IgG1 or IgG4 section in the spacer region of the CAR construct. A co-staining for CD3/CD8/CD4 T cells was performed. For the results refer to FIG. 7.

II. Co-Cultures of CAR-Transduced Human T Cells with Different Target Cell Lines Show Specific T Cell Activation by Distinct BCMA$^+$ Multiple Myeloma (MM) and B-NHL Cell Lines.

The readout was release of IFN-gamma as effector cytokine from T cells.

Generate retrovirus-transduced human T cells, as detailed before; employ all BCMA CAR-receptor variants (IX-XVII), SP6-negative control CAR, CD19 CAR, UT=untransduced T cells. Use the following human cell lines as target cells in co-culture:

| Cell line | Origin | BCMA-positivity |
|---|---|---|
| NCI-H929 | multiple myeloma (MM) | yes |
| MM.1S | MM | yes |
| OPM-2 | MM | yes |
| RPMI 8226 | MM | yes |
| REH | B acute lymphoblastic leukemia (B-ALL) | no |
| REH-BCMA | REH stably transduced with BCMA | yes |
| DOHH-2 | immunoblastic B cell lymphoma progressed from follicular centroblastic/centrocytic lymphoma (FL) | yes, weakly |
| JVM-3 | B cell chronic lymphocytic leukemia (B-CLL) | yes, weakly |
| SU-DHL4 | diffuse large B cell lymphoma (DLBCL), germinal center type | yes, weakly |
| NALM-6 | B acute lymphoblastic leukemia (B-ALL) | no |
| RS4 | B-ALL | no |
| Jurkat | T cell acute lymphoblastic leukemia (T-ALL) | no |
| normal peripheral B cells | healthy donor | no |
| MEC-1 | B-CLL | yes, weakly |
| JEKO-1 | mantle cell lymphoma (MCL), B-NHL | yes, weakly |
| HUVEC | human umbilical vein endothelial cells, healthy donor | no |
| SW620 | colon carcinoma | no |
| HT116 | colon carcinoma | no |
| HEK293 | human embryonic kidney epithelial cells | no |
| PBMC | human peripheral blood mononuclear cells, healthy donor | no |

Co-culture retrovirally transduced T cells for 18-20 hrs in the presence of the listed cell lines or primary cells at a ratio 1:1. After that time, take cell-free culture supernatant; max. release is induced by PMA/ionomycin stimulation of effector T cells; minimum release is T cells only. Determine IFN-gamma release in the supernatant by ELISA. Refer to FIG. 8 for the results.

III. CD107a (LAMP1) Staining of Co-Cultured CAR-T Cells with Multiple Myeloma Cells: Detection of Activated Degranulating CD8$^+$ T Cells Upon Antigen-Specific (BCMA) Stimulation by Flow Cytometry.

Generate retrovirus-transduced human T cells, as detailed above; employ BCMA CAR-receptor variants (IX-XI), SP6-negative control CAR.

Co-culture retrovirally transduced T cells for 18 hrs in the presence of the listed cell lines at a ratio of 1:1.

Add for overnight culture anti CD107a (LAMP1) antibody into cell medium; antibody binds continuously on T cells when secretory lysosomes are fusing with the plasma membrane and release the enzymatic content of their vesicles. These vesicles contain cytolytic mediators such as granzymes and perforin. On the next day, T cells are co-stained with anti CD8 and/or CD3.

Analysis by flow cytometry: higher CD107a reactivity, expressed as mean fluorescence intensity (MFI), indicates stronger activation of T cells. The antigen-dependent activation of T cells can be confirmed. For results refer to FIG. 9.

IV. Cytotoxicity Assays Reveal Selective Killing of BCMA-Positive Cell Lines; Essentially No Killing was Seen in BCMA-Negative Cell Lines.

Use of $^{51}$Cr-release assay for quantitation of cytotoxic T lymphocyte activity. Measure target cell cytolysis.

Generate retrovirus-transduced human T cells, as detailed before; employ BCMA CAR-receptor variants (IX-XI), SP6-negative control CAR; CD19 CAR as control Label target cells with $^{51}$Cr. Co-culture then CAR-T cells and labeled target cells for 4 hrs. Titrate the effector to target ratio.

E:T
80:1
40:1
20:1
10:1
5:1
2.5:1

Harvest cell-free cell culture supernatant. Transfer supernatant to LUMA-scintillation plates, measure released $^{51}$Cr in a gamma-scintillation counter. Max. release: target cells lysed by Triton X-100 Permeabilization. Min. release: target cells alone. For the results, refer to FIG. 10.

Furthermore, FIG. 11 provides results showing the amount of BCMA and CD19 expressed on the surface of each of the cell types assessed for cytotoxicity. FIG. 11 provides a schematic representation of the interaction between the scFV binding region of the CAR and the BCMA epitope.

Example 4: In Vivo Experiments Using a Xenotransplantation NSG Mouse Model to Assess Adoptively Transferred CAR-T Cells Against B-NHL and Myeloma Cell Lines In Vivo Experiments Using Xenotransplantation into NSG Mice:

1) To demonstrate that CART cells equipped with the diverse anti BCMA-variants have effector activity also under in situ conditions, multiple myeloma cells with different BCMA antigen densities are transplanted via an i.v. route into NSG-mice (NOD.Cg-Prkdc$^{scid}$ Il2rg$^{tm1\ Wjl}$/SzJ). The multiple myeloma cell lines that may be employed are: RPMI-8226, low BCMA; MM1S, intermediate BCMA density; NCI-H229, high BCMA density.

2) To confirm anti BCMA CAR T cell reactivity against B-NHL cell lines in situ, NSG mice are injected i.v. with luciferase-transduced cell lines, such as SU-DHL4 (DLBCL), JEKO-1 (mantle cell lymphoma), JVM3 (CLL), MEC1 (CLL), DOHH-2 (FL).

BCMA CAR-T Cells Mediate In Vivo Antitumor Activity in Mouse Models of Multiple Myeloma (MM) and B-Cell Non-Hodgkin's Lymphoma (B-NHL):

To provide proof-of-concept that the strong in vitro activity of T cells modified with the BCMA CAR translates into efficient antitumor activity in vivo, we inoculated cohorts of NOD.Cg-Prkdc$^{scid}$Il2rg$^{tm1\ Wjl}$/SzJ (NSG) mice i.v. with the human MM.1S cell line (FIG. 15) or the B-NHL cell line JeKo-1 (mantle cell lymphoma) (FIG. 16), transduced with the luciferase gene in tandem with GFP. NSG mice do not develop T, B, and NK cells and are therefore suitable for tolerance and growth of xenotransplanted human cells. Within the experimental time frame presented here, "graft-versus-host" (GvHD) reactions (xenoreactivity) was not observed (data not shown). Tumor growth was monitored by IVIS imaging and luciferin injection 7-8 days thereafter. Following tumor growth confirmation, CAR-T cells were i.v. injected one day later (=day 0). For functional in vivo experiments CAR construct IX (B IX) was used. Total numbers never exceeded 6-7×10$^6$/animal CAR-T cells, and the average transduction rate for T cells in this population was 40-60%. Per donor, SP6 and BCMA transduction rates were matched within a range of +/−10%. For the two experiments shown, an effective rate of 3×10$^6$ transduced CAR-T cells was used. Control mice received SP6 CAR-T cells.

In the MM1.S experiment (FIG. 15), 3×10$^6$ transduced CAR-T cells (as above, total: 6-7×10$^6$) were transplanted and the observation interval was extended to 17 days. While essentially all SP6 CAR treated animals had progressive MM disease, characterized by strong luminescence signals over the spine, pelvis, and hind legs, or were sacrificed because of disease progression in accordance with (Berlin State) animal protection laws, this was clearly not the case for the BCMA CAR treatment group. We conclude that at this comparably low CAR-T cell number the BCMA CAR-T cells already have anti-myeloma activity (FIG. 15A-C).

Due to the high affinity and avidity of the anti-BCMA CAR-T cell, even low BCMA-expressing mature B cell NHL can be recognized, allowing for T cell activation and tumor cell killing. Such mature B-NHL entities include certain stages of follicular lymphoma, diffuse large B-cell lymphoma, mantle cell lymphoma, and chronic lymphocytic leukemia (see FIGS. 11, 10, 9, 8). To prove the suitability of BCMA as a target structure in B-NHL entities, transduced CAR-T cells (total: 6-7×10$^6$) were transplanted in NSG mice which had been challenged with the mantle cell lymphoma cell line JeKo-1. While essentially all SP6 CAR treated animals had progressive lymphoma disease, characterized by strong luminescence signals over the liver, thoracical organs, bone marrow in hind limbs, and spleen, this was clearly not the case for the BCMA CAR treatment group. With this we provide the first pre-clinical in vivo proof that BCMA CAR-T cells have anti-tumor activity beyond multiple myeloma and extending to B-NHL lymphoma entities (FIG. 16A-C).

Example 5: Determination of Surface Density of BCMA Molecules

The high affinity and avidity of the anti-BCMA CAR-T cells allow for the recognition of even low BCMA-expressing mature B cell NHL entities, resulting in T cell activation and tumor cell killing. Such mature B-NHL entities include certain stages of follicular lymphoma, diffuse large B-cell lymphoma, mantle cell lymphoma, and chronic lymphocytic leukemia.

To quantify the surface density of the BCMA molecules, we have applied the PE Phycoerythrin Fluorescence Detection Kit, also referred to as BD Quantibrite assay (BD Bioscience). The number of PE molecules per cell can be converted to antibodies per cell, which is a quantitative estimate of the number of antigens per cell. A flow cytometry detection method was applied.

Using this method, we find that the multiple myeloma cell line NCI-H929 has a relative surface BCMA antigen density of 12555, the multiple myeloma cell line OPM-2 has 3443 BCMA molecules, and the multiple myeloma cell line MM.1S has a relative value of 3181.

The BCMA antigen densities for the mentioned B-NHL cell lines, relative to NCI-H929, are:

DOHH-2: 1/20, JeKo-1: 1/250, MEC-1: 1/34

SEQUENCE LISTING

<160> NUMBER OF SEQ ID NOS: 94

<210> SEQ ID NO 1
<211> LENGTH: 8
<212> TYPE: PRT
<213> ORGANISM: Artificial Sequence
<220> FEATURE:
<223> OTHER INFORMATION: CDR

<400> SEQUENCE: 1

Gly Phe Thr Phe Ser Arg Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: CDR

<400> SEQUENCE: 2

Ile Asn Pro Ser Ser Ser Thr Ile
1               5

<210> SEQ ID NO 3
<211> LENGTH: 13
<212> TYPE: PRT
<213> ORGANISM: Artificial Sequence
<220> FEATURE:
<223> OTHER INFORMATION: CDR

<400> SEQUENCE: 3

Ala Ser Leu Tyr Tyr Asp Tyr Gly Asp Ala Tyr Asp Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: CDR

<400> SEQUENCE: 4

Gln Ser Val Glu Ser Asn
1               5

<210> SEQ ID NO 5
<211> LENGTH: 4
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Ser Ala Ser Xaa
1

<210> SEQ ID NO 6
<211> LENGTH: 9
<212> TYPE: PRT
<213> ORGANISM: Artificial Sequence
<220> FEATURE:
<223> OTHER INFORMATION: CDR

```
<400> SEQUENCE: 6

Gln Gln Tyr Asn Asn Tyr Pro Leu Thr
1               5

<210> SEQ ID NO 7
<211> LENGTH: 8
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (4)..(5)
<223> OTHER INFORMATION: Xaa can be any naturally occurring amino acid

<400> SEQUENCE: 7

Ile Asn Pro Xaa Xaa Ser Thr Ile
1               5

<210> SEQ ID NO 8
<211> LENGTH: 13
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 8

Ala Ser Leu Tyr Xaa Asp Tyr Gly Asp Ala Xaa Asp Tyr
1               5                   10

<210> SEQ ID NO 9
<211> LENGTH: 6
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (4)..(5)
<223> OTHER INFORMATION: Xaa can be any naturally occurring amino acid

<400> SEQUENCE: 9

Gln Ser Val Xaa Xaa Asn
1               5

<210> SEQ ID NO 10
<211> LENGTH: 11
<212> TYPE: PRT
<213> ORGANISM: Artificial Sequence
<220> FEATURE:
<223> OTHER INFORMATION: CDR

<400> SEQUENCE: 10

Gln Gln Tyr Asn Asn Tyr Pro Leu Thr Phe Gly
1               5                   10

<210> SEQ ID NO 11
<211> LENGTH: 120
<212> TYPE: PRT
<213> ORGANISM: Artificial Sequence
<220> FEATURE:
```

<223> OTHER INFORMATION: VH

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Phe Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
            115                 120

<210> SEQ ID NO 12
<211> LENGTH: 107
<212> TYPE: PRT
<213> ORGANISM: Artificial Sequence
<220> FEATURE:
<223> OTHER INFORMATION: VL

<400> SEQUENCE: 12

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Glu Ser Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
            85                  90                  95

Thr Phe Gly Ala Gly Thr Lys Leu Glu Leu Lys
            100                 105

<210> SEQ ID NO 13
<211> LENGTH: 18
<212> TYPE: PRT
<213> ORGANISM: Artificial Sequence
<220> FEATURE:
<223> OTHER INFORMATION: linker

<400> SEQUENCE: 13

Gly Ser Thr Ser Gly Ser Gly Lys Pro Gly Ser Gly Glu Gly Ser Thr
1               5                   10                  15

Lys Gly

<210> SEQ ID NO 14
<211> LENGTH: 17
<212> TYPE: PRT
<213> ORGANISM: Artificial Sequence

```
<220> FEATURE:
<223> OTHER INFORMATION: linker

<400> SEQUENCE: 14

Ser Ser Gly Gly Gly Ser Gly Gly Gly Ser Gly Gly Gly Gly
1               5                   10                  15
Ser

<210> SEQ ID NO 15
<211> LENGTH: 234
<212> TYPE: PRT
<213> ORGANISM: Artificial Sequence
<220> FEATURE:
<223> OTHER INFORMATION: spacer

<400> SEQUENCE: 15

Pro Ala Glu Pro Lys Ser Pro Asp Lys Thr His Thr Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ala Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys
225                 230

<210> SEQ ID NO 16
<211> LENGTH: 235
<212> TYPE: PRT
<213> ORGANISM: Artificial Sequence
<220> FEATURE:
<223> OTHER INFORMATION: spacer

<400> SEQUENCE: 16

Pro Ala Glu Pro Lys Ser Pro Asp Lys Thr His Thr Cys Pro Pro Cys
1               5                   10                  15

Pro Ala Pro Pro Val Ala Gly Pro Ser Val Phe Leu Phe Pro Pro Lys
```

```
            20                  25                  30
Pro Lys Asp Thr Leu Met Ile Ala Arg Thr Pro Glu Val Thr Cys Val
            35                  40                  45

Val Val Asp Val Ser His Glu Asp Pro Glu Val Lys Phe Asn Trp Tyr
        50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Ser Leu Ser Pro Gly Lys Lys
225                 230                 235

<210> SEQ ID NO 17
<211> LENGTH: 229
<212> TYPE: PRT
<213> ORGANISM: Artificial Sequence
<220> FEATURE:
<223> OTHER INFORMATION: spacer

<400> SEQUENCE: 17

Glu Ser Lys Tyr Gly Pro Pro Cys Pro Pro Cys Pro Ala Pro Glu Phe
 1               5                  10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
```

```
                145                 150                 155                 160
Val Glu Trp Glu Ser Asn Gly Gln Pro Glu Asn Asn Tyr Lys Thr Thr
                    165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
        210                 215                 220

Leu Ser Leu Gly Lys
225

<210> SEQ ID NO 18
<211> LENGTH: 119
<212> TYPE: PRT
<213> ORGANISM: Artificial Sequence
<220> FEATURE:
<223> OTHER INFORMATION: spacer

<400> SEQUENCE: 18

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 19
<211> LENGTH: 12
<212> TYPE: PRT
<213> ORGANISM: Artificial Sequence
<220> FEATURE:
<223> OTHER INFORMATION: spacer

<400> SEQUENCE: 19

Glu Ser Lys Tyr Gly Pro Pro Cys Pro Pro Cys Pro
1               5                   10

<210> SEQ ID NO 20
<211> LENGTH: 24
<212> TYPE: PRT
<213> ORGANISM: Artificial Sequence
<220> FEATURE:
<223> OTHER INFORMATION: transmembrane

<400> SEQUENCE: 20

Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 21
<211> LENGTH: 27
<212> TYPE: PRT
<213> ORGANISM: Artificial Sequence
<220> FEATURE:
<223> OTHER INFORMATION: transmembrane

<400> SEQUENCE: 21

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 22
<211> LENGTH: 42
<212> TYPE: PRT
<213> ORGANISM: Artificial Sequence
<220> FEATURE:
<223> OTHER INFORMATION: intracellular

<400> SEQUENCE: 22

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 23
<211> LENGTH: 41
<212> TYPE: PRT
<213> ORGANISM: Artificial Sequence
<220> FEATURE:
<223> OTHER INFORMATION: intracellular

<400> SEQUENCE: 23

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 24
<211> LENGTH: 113
<212> TYPE: PRT
<213> ORGANISM: Artificial Sequence
<220> FEATURE:
<223> OTHER INFORMATION: intracellular

<400> SEQUENCE: 24

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Gly Arg Asp Pro Glu Met Gly Gly
            35                  40                  45

Lys Pro Arg Arg Lys Asn Pro Gln Glu Gly Leu Tyr Asn Glu Leu Gln
50                  55                  60

Lys Asp Lys Met Ala Glu Ala Tyr Ser Glu Ile Gly Met Lys Gly Glu
65                  70                  75                  80

```
Arg Arg Arg Gly Lys Gly His Asp Gly Leu Tyr Gln Gly Leu Ser Thr
                85                  90                  95
Ala Thr Lys Asp Thr Tyr Asp Ala Leu His Met Gln Ala Leu Pro Pro
            100                 105                 110
Arg

<210> SEQ ID NO 25
<211> LENGTH: 5
<212> TYPE: PRT
<213> ORGANISM: Artificial Sequence
<220> FEATURE:
<223> OTHER INFORMATION: CDR

<400> SEQUENCE: 25

Arg Tyr Trp Phe Ser
1               5

<210> SEQ ID NO 26
<211> LENGTH: 18
<212> TYPE: PRT
<213> ORGANISM: Artificial Sequence
<220> FEATURE:
<223> OTHER INFORMATION: CDR

<400> SEQUENCE: 26

Glu Ile Asn Pro Ser Ser Ser Thr Ile Asn Tyr Ala Pro Ser Leu Lys
1               5                   10                  15
Asp Lys

<210> SEQ ID NO 27
<211> LENGTH: 13
<212> TYPE: PRT
<213> ORGANISM: Artificial Sequence
<220> FEATURE:
<223> OTHER INFORMATION: CDR

<400> SEQUENCE: 27

Ser Leu Tyr Tyr Asp Tyr Gly Asp Ala Tyr Asp Tyr Trp
1               5                   10

<210> SEQ ID NO 28
<211> LENGTH: 11
<212> TYPE: PRT
<213> ORGANISM: Artificial Sequence
<220> FEATURE:
<223> OTHER INFORMATION: CDR

<400> SEQUENCE: 28

Lys Ala Ser Gln Ser Val Glu Ser Asn Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CDR

<400> SEQUENCE: 29

Ser Ala Ser Leu Arg Phe Ser
1               5

<210> SEQ ID NO 30
<211> LENGTH: 11
```

```
<212> TYPE: PRT
<213> ORGANISM: Artificial Sequence
<220> FEATURE:
<223> OTHER INFORMATION: CDR

<400> SEQUENCE: 30

Gln Gln Tyr Asn Asn Tyr Pro Leu Thr Phe Gly
1               5                   10

<210> SEQ ID NO 31
<211> LENGTH: 53
<212> TYPE: PRT
<213> ORGANISM: Homo sapiens

<400> SEQUENCE: 31

Met Ala Gly Gln Cys Ser Gln Asn Glu Tyr Phe Asp Ser Leu Leu His
1               5                   10                  15

Ala Cys Ile Pro Cys Gln Leu Arg Cys Ser Ser Asn Thr Pro Pro Leu
            20                  25                  30

Thr Cys Gln Arg Tyr Cys Asn Ala Ser Val Thr Asn Ser Val Lys Gly
        35                  40                  45

Thr Asn Ala Leu Glu
    50

<210> SEQ ID NO 32
<211> LENGTH: 56
<212> TYPE: PRT
<213> ORGANISM: Homo sapiens

<400> SEQUENCE: 32

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Leu Glu
    50                  55

<210> SEQ ID NO 33
<211> LENGTH: 20
<212> TYPE: PRT
<213> ORGANISM: Homo sapiens

<400> SEQUENCE: 33

Tyr Phe Asp Ser Leu Leu His Ala Cys Ile Pro Cys Gln Leu Arg Cys
1               5                   10                  15

Ser Ser Asn Thr
            20

<210> SEQ ID NO 34
<211> LENGTH: 5
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Arg Tyr Trp Xaa Ser
1               5
```

```
<210> SEQ ID NO 35
<211> LENGTH: 18
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (5)..(6)
<223> OTHER INFORMATION: Xaa can be any naturally occurring amino acid

<400> SEQUENCE: 35

Glu Ile Asn Pro Xaa Xaa Ser Thr Ile Asn Tyr Ala Pro Ser Leu Lys
1               5                   10                  15

Asp Lys

<210> SEQ ID NO 36
<211> LENGTH: 13
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 36

Ser Leu Tyr Xaa Asp Tyr Gly Asp Ala Xaa Asp Tyr Trp
1               5                   10

<210> SEQ ID NO 37
<211> LENGTH: 11
<212> TYPE: PRT
<213> ORGANISM: Artificial Sequence
<220> FEATURE:
<223> OTHER INFORMATION: CDR
<220> FEATURE:
<221> NAME/KEY: misc_feature
<222> LOCATION: (7)..(8)
<223> OTHER INFORMATION: Xaa can be any naturally occurring amino acid

<400> SEQUENCE: 37

Lys Ala Ser Gln Ser Val Xaa Xaa Asn Val Ala
1               5                   10

<210> SEQ ID NO 38
<211> LENGTH: 120
<212> TYPE: PRT
<213> ORGANISM: Artificial
<220> FEATURE:
<223> OTHER INFORMATION: mouse Ab

<400> SEQUENCE: 38

Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
                20                  25                  30

Trp Met Ser Trp Val Arg Arg Ala Pro Gly Lys Gly Leu Glu Trp Ile
            35                  40                  45

Gly Glu Ile Asn Pro Asp Ser Ser Thr Ile Asn Tyr Ala Pro Ser Leu
```

```
                    50                  55                  60
Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Ser Leu Tyr Tyr Asp Tyr Gly Asp Ala Met Asp Tyr Trp Gly Gln
                100                 105                 110

Gly Thr Ser Val Thr Val Ser Ser
            115                 120

<210> SEQ ID NO 39
<211> LENGTH: 120
<212> TYPE: PRT
<213> ORGANISM: Artificial Sequence
<220> FEATURE:
<223> OTHER INFORMATION: Ab

<400> SEQUENCE: 39

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
                 20                  25                  30

Trp Met Ser Trp Val Arg Gln Ala Pro Gly Lys Gly Leu Glu Trp Val
             35                  40                  45

Gly Glu Ile Asn Pro Asp Ser Ser Thr Ile Asn Tyr Ala Pro Ser Leu
         50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Leu Tyr Tyr Asp Tyr Gly Asp Ala Met Asp Tyr Trp Gly Gln
                100                 105                 110

Gly Thr Leu Val Thr Val Ser Ser
            115                 120

<210> SEQ ID NO 40
<211> LENGTH: 120
<212> TYPE: PRT
<213> ORGANISM: Artificial Sequence
<220> FEATURE:
<223> OTHER INFORMATION: VH

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                 20                  25                  30

Trp Met Ser Trp Val Arg Gln Ala Pro Gly Lys Gly Leu Val Trp Val
             35                  40                  45

Gly Glu Ile Asn Pro Asp Ser Ser Thr Ile Asn Tyr Ala Pro Ser Leu
         50                  55                  60

Lys Asp Lys Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Leu Tyr Tyr Asp Tyr Gly Asp Ala Met Asp Tyr Trp Gly Gln
                100                 105                 110
```

```
Gly Thr Leu Val Thr Val Ser Ser
        115                 120

<210> SEQ ID NO 41
<211> LENGTH: 120
<212> TYPE: PRT
<213> ORGANISM: Artificial Sequence
<220> FEATURE:
<223> OTHER INFORMATION: VH
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Xaa Ser Trp Val Arg Gln Ala Pro Gly Lys Gly Leu Val Trp Val
        35                  40                  45

Gly Glu Ile Asn Pro Xaa Xaa Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Xaa Asp Tyr Gly Asp Ala Xaa Asp Tyr Trp Gly Gln
            100                 105                 110

Gly Thr Leu Val Thr Val Ser Ser
        115                 120

<210> SEQ ID NO 42
<211> LENGTH: 120
<212> TYPE: PRT
<213> ORGANISM: Artificial Sequence
<220> FEATURE:
<223> OTHER INFORMATION: VH
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (99)..(101)
```

<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Xaa Met Xaa Trp Val Arg Gln Ala Pro Gly Lys Gly Leu Val Xaa Val
        35                  40                  45

Gly Xaa Ile Asn Pro Asp Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Xaa Xaa Xaa Asp Tyr Gly Asp Xaa Met Asp Tyr Trp Gly Gln
            100                 105                 110

Gly Thr Leu Val Thr Val Ser Ser
        115                 120

<210> SEQ ID NO 43
<211> LENGTH: 120
<212> TYPE: PRT
<213> ORGANISM: Artificial Sequence
<220> FEATURE:
<223> OTHER INFORMATION: VH

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Val Trp Val
        35                  40                  45

Gly Glu Ile Asn Pro Asn Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Artificial Sequence
<220> FEATURE:
<223> OTHER INFORMATION: VH

<400> SEQUENCE: 44

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Arg Tyr
            20                  25                  30

Trp Phe Ser Trp Val Arg Gln Ala Pro Gly Lys Gly Leu Val Trp Val
        35                  40                  45

Gly Glu Ile Asn Pro Asn Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 45
<211> LENGTH: 120
<212> TYPE: PRT
<213> ORGANISM: Artificial Sequence
<220> FEATURE:
<223> OTHER INFORMATION: VH

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 46
<211> LENGTH: 120
<212> TYPE: PRT
<213> ORGANISM: Artificial Sequence
<220> FEATURE:
<223> OTHER INFORMATION: VH

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Phe Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 47
<211> LENGTH: 108
<212> TYPE: PRT
<213> ORGANISM: Artificial Sequence
<220> FEATURE:
<223> OTHER INFORMATION: VL

<400> SEQUENCE: 47

Asp Ile Val Met Thr Gln Ser Gln Arg Phe Met Thr Thr Ser Val Gly
1               5                   10                  15

Asp Arg Val Ser Val Thr Cys Lys Ala Ser Gln Ser Val Asp Ser Asn
            20                  25                  30

Val Ala Trp Tyr Gln Gln Lys Pro Arg Gln Ser Pro Lys Ala Leu Ile
        35                  40                  45

Phe Ser Ala Ser Leu Arg Phe Ser Gly Val Pro Ala Arg Phe Thr Gly
    50                  55                  60

Ser Gly Ser Gly Thr Asp Phe Thr Leu Thr Ile Ser Asn Leu Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 48
<211> LENGTH: 108
<212> TYPE: PRT
<213> ORGANISM: Artificial Sequence
<220> FEATURE:
<223> OTHER INFORMATION: VL

<400> SEQUENCE: 48

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 49
<211> LENGTH: 108
<212> TYPE: PRT
<213> ORGANISM: Artificial Sequence
<220> FEATURE:
<223> OTHER INFORMATION: VL

<400> SEQUENCE: 49

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Asp Ser Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 50
<211> LENGTH: 108
<212> TYPE: PRT
<213> ORGANISM: Artificial Sequence
<220> FEATURE:
<223> OTHER INFORMATION: VL
<220> FEATURE:
<221> NAME/KEY: misc_feature
<222> LOCATION: (30)..(31)
<223> OTHER INFORMATION: Xaa can be any naturally occurring amino acid

<400> SEQUENCE: 50

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Xaa Xaa Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 51
<211> LENGTH: 108
<212> TYPE: PRT
<213> ORGANISM: Artificial Sequence
<220> FEATURE:
<223> OTHER INFORMATION: VL
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:

-continued

```
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid

<400> SEQUENCE: 51

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Asp Xaa Xaa
            20                  25                  30

Val Xaa Trp Xaa Gln Gln Lys Pro Gly Gln Ala Pro Arg Ala Leu Ile
        35                  40                  45

Xaa Xaa Ala Xaa Xaa Arg Xaa Ser Gly Ile Pro Ala Arg Phe Ser Gly
    50                  55                  60

Ser Xaa Xaa Gly Thr Glu Phe Thr Leu Thr Ile Ser Ser Leu Gln Ser
65                  70                  75                  80

Glu Asp Phe Ala Val Tyr Tyr Cys Xaa Gln Xaa Asn Asn Xaa Pro Xaa
                85                  90                  95

Thr Phe Gly Ala Gly Thr Lys Leu Glu Leu Lys Arg
            100                 105

<210> SEQ ID NO 52
<211> LENGTH: 108
<212> TYPE: PRT
<213> ORGANISM: Artificial Sequence
<220> FEATURE:
<223> OTHER INFORMATION: VL

<400> SEQUENCE: 52

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Glu Ser Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

Glu Asp Phe Ala Val Tyr Tyr Cys Gln Gln Tyr Asn Asn Tyr Pro Leu
            85                  90                  95

Thr Phe Gly Ala Gly Thr Lys Leu Glu Leu Lys Arg
            100                 105

<210> SEQ ID NO 53
<211> LENGTH: 120
<212> TYPE: PRT
<213> ORGANISM: Artificial Sequence
<220> FEATURE:
<223> OTHER INFORMATION: VH
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be Ile, Phe, Leu, Val, Tyr, Cys, Gly,
      Ala, Ser, or Thr
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be Ser, Asn, Thr, Gly, Lys, Arg, or Asp
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be Tyr, Leu, Phe, Ile, Val, Ala, or Cys
<220> FEATURE:
<221> NAME/KEY: misc_feature
<222> LOCATION: (115)..(115)
<223> OTHER INFORMATION: Xaa can be any naturally occurring amino acid

<400> SEQUENCE: 53

Xaa Val Gln Leu Xaa Xaa Ser Gly Gly Gly Leu Val Gln Pro Gly Gly
1               5                   10                  15

Ser Leu Xaa Leu Ser Cys Ala Ala Ser Gly Xaa Xaa Phe Xaa Xaa Tyr
            20                  25                  30

Trp Xaa Ser Trp Val Arg Xaa Ala Pro Gly Lys Gly Leu Glu Trp Xaa
        35                  40                  45

Gly Glu Ile Asn Pro Xaa Ser Ser Thr Ile Asn Tyr Ala Pro Ser Leu
            50                  55                  60

Lys Xaa Xaa Phe Xaa Ile Ser Arg Asp Asn Ala Lys Asn Thr Leu Tyr
65              70                  75                  80

Leu Gln Met Xaa Xaa Xaa Arg Xaa Glu Asp Thr Ala Xaa Tyr Tyr Cys
                85                  90                  95

Ala Ser Leu Tyr Tyr Asp Tyr Gly Asp Ala Xaa Asp Tyr Trp Gly Gln
            100                 105                 110

Gly Thr Xaa Val Thr Val Ser Ser
        115                 120

<210> SEQ ID NO 54
<211> LENGTH: 108
<212> TYPE: PRT
<213> ORGANISM: Artificial Sequence
<220> FEATURE:
<223> OTHER INFORMATION: VL
<220> FEATURE:
<221> NAME/KEY: misc_feature
<222> LOCATION: (8)..(13)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:

<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid

<400> SEQUENCE: 54

Asp Ile Val Met Thr Gln Ser Xaa Xaa Xaa Xaa Xaa Ser Val Gly
1               5                  10                  15

Asp Xaa Val Xaa Xaa Thr Cys Lys Ala Ser Gln Ser Val Glu Ser Asn
            20                  25                  30

Val Ala Trp Tyr Gln Gln Lys Pro Xaa Gln Xaa Pro Lys Xaa Leu Ile
        35                  40                  45

Xaa Ser Xaa Xaa Leu Arg Phe Ser Gly Val Pro Ala Arg Phe Xaa Gly
    50                  55                  60

Ser Gly Ser Gly Thr Asp Phe Thr Leu Thr Ile Ser Xaa Leu Gln Ser
65                  70                  75                  80

Glu Asp Xaa Ala Xaa Tyr Xaa Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 55
<211> LENGTH: 21
<212> TYPE: PRT
<213> ORGANISM: Artificial Sequence
<220> FEATURE:
<223> OTHER INFORMATION: leader

<400> SEQUENCE: 55

Met Asp Phe Gln Val Gln Ile Phe Ser Phe Leu Leu Ile Ser Ala Ser
1               5                   10                  15

Val Ile Met Ser Arg
            20

<210> SEQ ID NO 56
<211> LENGTH: 21
<212> TYPE: PRT
<213> ORGANISM: Artificial Sequence
<220> FEATURE:
<223> OTHER INFORMATION: leader

<400> SEQUENCE: 56

Met Leu Leu Leu Val Thr Ser Leu Leu Cys Glu Leu Pro His Pro
1               5                   10                  15

Ala Phe Leu Leu Ile
            20

<210> SEQ ID NO 57
<211> LENGTH: 684
<212> TYPE: PRT
<213> ORGANISM: Artificial Sequence
<220> FEATURE:
<223> OTHER INFORMATION: construct

<400> SEQUENCE: 57

Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
            20                  25                  30

Val Gln Pro Gly Gly Ser Leu Arg Leu Ser Cys Ala Ala Ser Gly Phe
            35                  40                  45

Thr Phe Ser Arg Tyr Trp Phe Ser Trp Val Arg Gln Ala Pro Gly Lys
 50                  55                  60

Gly Leu Val Trp Val Gly Glu Ile Asn Pro Ser Ser Ser Thr Ile Asn
 65                  70                  75                  80

Tyr Ala Pro Ser Leu Lys Asp Lys Phe Thr Ile Ser Arg Asp Asn Ala
                 85                  90                  95

Lys Asn Thr Leu Tyr Leu Gln Met Asn Ser Leu Arg Ala Glu Asp Thr
             100                 105                 110

Ala Val Tyr Tyr Cys Ala Ser Leu Tyr Asp Tyr Gly Asp Ala Tyr
             115                 120                 125

Asp Tyr Trp Gly Gln Gly Thr Leu Val Thr Val Ser Ser Gly Ser Thr
         130                 135                 140

Ser Gly Ser Gly Lys Pro Gly Ser Gly Glu Gly Ser Thr Lys Gly Glu
145                 150                 155                 160

Ile Val Met Thr Gln Ser Pro Ala Thr Leu Ser Val Ser Pro Gly Glu
             165                 170                 175

Arg Ala Thr Leu Ser Cys Lys Ala Ser Gln Ser Val Glu Ser Asn Val
             180                 185                 190

Ala Trp Tyr Gln Gln Lys Pro Gly Gln Ala Pro Arg Ala Leu Ile Tyr
         195                 200                 205

Ser Ala Ser Leu Arg Phe Ser Gly Ile Pro Ala Arg Phe Ser Gly Ser
         210                 215                 220

Gly Ser Gly Thr Glu Phe Thr Leu Thr Ile Ser Ser Leu Gln Ser Glu
225                 230                 235                 240

Asp Phe Ala Val Tyr Tyr Cys Gln Gln Tyr Asn Asn Tyr Pro Leu Thr
             245                 250                 255

Phe Gly Ala Gly Thr Lys Leu Glu Leu Lys Pro Ala Glu Pro Lys Ser
             260                 265                 270

Pro Asp Lys Thr His Thr Cys Pro Pro Cys Pro Ala Pro Pro Val Ala
         275                 280                 285

Gly Pro Ser Val Phe Leu Phe Pro Pro Lys Pro Lys Asp Thr Leu Met
290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
             325                 330                 335

His Asn Ala Lys Thr Lys Pro Arg Glu Glu Gln Tyr Asn Ser Thr Tyr
             340                 345                 350

Arg Val Val Ser Val Leu Thr Val Leu His Gln Asp Trp Leu Asn Gly
         355                 360                 365

Lys Glu Tyr Lys Cys Lys Val Ser Asn Lys Ala Leu Pro Ala Pro Ile
         370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
             405                 410                 415

Leu Thr Cys Leu Val Lys Gly Phe Tyr Pro Ser Asp Ile Ala Val Glu
             420                 425                 430

Trp Glu Ser Asn Gly Gln Pro Glu Asn Asn Tyr Lys Thr Thr Pro Pro
         435                 440                 445

Val Leu Asp Ser Asp Gly Ser Phe Phe Leu Tyr Ser Lys Leu Thr Val

```
            450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Lys Asp Pro Lys Phe Trp Val Leu Val Val Gly Gly
                500                 505                 510

Val Leu Ala Cys Tyr Ser Leu Leu Val Thr Val Ala Phe Ile Ile Phe
                515                 520                 525

Trp Val Arg Ser Lys Arg Ser Arg Leu Leu His Ser Asp Tyr Met Asn
            530                 535                 540

Met Thr Pro Arg Arg Pro Gly Pro Thr Arg Lys His Tyr Gln Pro Tyr
545                 550                 555                 560

Ala Pro Pro Arg Asp Phe Ala Ala Tyr Arg Ser Leu Arg Val Lys Phe
                565                 570                 575

Ser Arg Ser Ala Asp Ala Pro Ala Tyr Gln Gln Gly Gln Asn Gln Leu
                580                 585                 590

Tyr Asn Glu Leu Asn Leu Gly Arg Arg Glu Glu Tyr Asp Val Leu Asp
            595                 600                 605

Lys Arg Arg Gly Arg Asp Pro Glu Met Gly Gly Lys Pro Arg Arg Lys
610                 615                 620

Asn Pro Gln Glu Gly Leu Tyr Asn Glu Leu Gln Lys Asp Lys Met Ala
625                 630                 635                 640

Glu Ala Tyr Ser Glu Ile Gly Met Lys Gly Glu Arg Arg Arg Gly Lys
                645                 650                 655

Gly His Asp Gly Leu Tyr Gln Gly Leu Ser Thr Ala Thr Lys Asp Thr
            660                 665                 670

Tyr Asp Ala Leu His Met Gln Ala Leu Pro Pro Arg
                675                 680

<210> SEQ ID NO 58
<211> LENGTH: 684
<212> TYPE: PRT
<213> ORGANISM: Artificial Sequence
<220> FEATURE:
<223> OTHER INFORMATION: construct

<400> SEQUENCE: 58

Met Asp Phe Gln Val Gln Ile Phe Ser Phe Leu Leu Ile Ser Ala Ser
1               5                   10                  15

Val Ile Met Ser Arg Glu Ile Val Met Thr Gln Ser Pro Ala Thr Leu
                20                  25                  30

Ser Val Ser Pro Gly Glu Arg Ala Thr Leu Ser Cys Lys Ala Ser Gln
                35                  40                  45

Ser Val Glu Ser Asn Val Ala Trp Tyr Gln Gln Lys Pro Gly Gln Ala
            50                  55                  60

Pro Arg Ala Leu Ile Tyr Ser Ala Ser Leu Arg Phe Ser Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
                100                 105                 110

Asn Asn Tyr Pro Leu Thr Phe Gly Ala Gly Thr Lys Leu Glu Leu Lys
            115                 120                 125

Gly Ser Thr Ser Gly Ser Gly Lys Pro Gly Ser Gly Glu Gly Ser Thr
```

```
            130                 135                 140
Lys Gly Glu Val Gln Leu Val Glu Ser Gly Gly Leu Val Gln Pro
145                 150                 155                 160

Gly Gly Ser Leu Arg Leu Ser Cys Ala Ala Ser Gly Phe Thr Phe Ser
            165                 170                 175

Arg Tyr Trp Phe Ser Trp Val Arg Gln Ala Pro Gly Lys Gly Leu Val
                180                 185                 190

Trp Val Gly Glu Ile Asn Pro Ser Ser Thr Ile Asn Tyr Ala Pro
        195                 200                 205

Ser Leu Lys Asp Lys Phe Thr Ile Ser Arg Asp Asn Ala Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Ser Leu Tyr Tyr Asp Tyr Gly Asp Ala Tyr Asp Tyr Trp
                245                 250                 255

Gly Gln Gly Thr Leu Val Thr Val Ser Ser Pro Ala Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Lys Asp Pro Lys Phe Trp Val Leu Val Val Val Gly Gly
            500                 505                 510

Val Leu Ala Cys Tyr Ser Leu Leu Val Thr Val Ala Phe Ile Ile Phe
        515                 520                 525

Trp Val Arg Ser Lys Arg Ser Arg Leu Leu His Ser Asp Tyr Met Asn
530                 535                 540

Met Thr Pro Arg Arg Pro Gly Pro Thr Arg Lys His Tyr Gln Pro Tyr
545                 550                 555                 560
```

Ala Pro Pro Arg Asp Phe Ala Ala Tyr Arg Ser Leu Arg Val Lys Phe
            565                 570                 575

Ser Arg Ser Ala Asp Ala Pro Ala Tyr Gln Gln Gly Gln Asn Gln Leu
            580                 585                 590

Tyr Asn Glu Leu Asn Leu Gly Arg Arg Glu Tyr Asp Val Leu Asp
            595                 600                 605

Lys Arg Arg Gly Arg Asp Pro Glu Met Gly Gly Lys Pro Arg Arg Lys
610                 615                 620

Asn Pro Gln Glu Gly Leu Tyr Asn Glu Leu Gln Lys Asp Lys Met Ala
625                 630                 635                 640

Glu Ala Tyr Ser Glu Ile Gly Met Lys Gly Glu Arg Arg Arg Gly Lys
            645                 650                 655

Gly His Asp Gly Leu Tyr Gln Gly Leu Ser Thr Ala Thr Lys Asp Thr
            660                 665                 670

Tyr Asp Ala Leu His Met Gln Ala Leu Pro Pro Arg
            675                 680

<210> SEQ ID NO 59
<211> LENGTH: 684
<212> TYPE: PRT
<213> ORGANISM: Artificial Sequence
<220> FEATURE:
<223> OTHER INFORMATION: construct

<400> SEQUENCE: 59

Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Arg Tyr Trp Phe Ser Trp Val Arg Gln Ala Pro Gly Lys
        50                  55                  60

Gly Leu Val Trp Val Gly Glu Ile Asn Pro Ser Ser Ser Thr Ile Asn
65                  70                  75                  80

Tyr Ala Pro Ser Leu Lys Asp Lys Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Ala Ser Leu Tyr Tyr Asp Tyr Gly Asp Ala Tyr
        115                 120                 125

Asp Tyr Trp Gly Gln Gly Thr Leu Val Thr Val Ser Ser Gly Ser Thr
    130                 135                 140

Ser Gly Ser Gly Lys Pro Gly Ser Gly Glu Gly Ser Thr Lys Gly Glu
145                 150                 155                 160

Ile Val Met Thr Gln Ser Pro Ala Thr Leu Ser Val Ser Pro Gly Glu
                165                 170                 175

Arg Ala Thr Leu Ser Cys Lys Ala Ser Gln Ser Val Glu Ser Asn Val
            180                 185                 190

Ala Trp Tyr Gln Gln Lys Pro Gly Gln Ala Pro Arg Ala Leu Ile Tyr
        195                 200                 205

Ser Ala Ser Leu Arg Phe Ser Gly Ile Pro Ala Arg Phe Ser Gly Ser
    210                 215                 220

Gly Ser Gly Thr Glu Phe Thr Leu Thr Ile Ser Ser Leu Gln Ser Glu
225                 230                 235                 240

```
Asp Phe Ala Val Tyr Tyr Cys Gln Gln Tyr Asn Asn Tyr Pro Leu Thr
                245                 250                 255

Phe Gly Ala Gly Thr Lys Leu Glu Leu Lys Pro Ala Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
    290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Lys Asp Pro Lys Phe Trp Val Leu Val Val Val Gly Gly
            500                 505                 510

Val Leu Ala Cys Tyr Ser Leu Leu Val Thr Val Ala Phe Ile Ile Phe
        515                 520                 525

Trp Val Arg Ser Lys Arg Ser Arg Leu Leu His Ser Asp Tyr Met Asn
    530                 535                 540

Met Thr Pro Arg Arg Pro Gly Pro Thr Arg Lys His Tyr Gln Pro Tyr
545                 550                 555                 560

Ala Pro Pro Arg Asp Phe Ala Ala Tyr Arg Ser Leu Arg Val Lys Phe
                565                 570                 575

Ser Arg Ser Ala Asp Ala Pro Ala Tyr Gln Gln Gly Gln Asn Gln Leu
            580                 585                 590

Tyr Asn Glu Leu Asn Leu Gly Arg Arg Glu Glu Tyr Asp Val Leu Asp
        595                 600                 605

Lys Arg Arg Gly Arg Asp Pro Glu Met Gly Gly Lys Pro Arg Arg Lys
    610                 615                 620

Asn Pro Gln Glu Gly Leu Tyr Asn Glu Leu Gln Lys Asp Lys Met Ala
625                 630                 635                 640

Glu Ala Tyr Ser Glu Ile Gly Met Lys Gly Glu Arg Arg Arg Gly Lys
                645                 650                 655
```

Gly His Asp Gly Leu Tyr Gln Gly Leu Ser Thr Ala Thr Lys Asp Thr
            660                 665                 670

Tyr Asp Ala Leu His Met Gln Ala Leu Pro Pro Arg
        675                 680

<210> SEQ ID NO 60
<211> LENGTH: 676
<212> TYPE: PRT
<213> ORGANISM: Artificial Sequence
<220> FEATURE:
<223> OTHER INFORMATION: construct

<400> SEQUENCE: 60

Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Arg Tyr Trp Phe Ser Trp Val Arg Gln Ala Pro Gly Lys
    50                  55                  60

Gly Leu Val Trp Val Gly Glu Ile Asn Pro Ser Ser Ser Thr Ile Asn
65                  70                  75                  80

Tyr Ala Pro Ser Leu Lys Asp Lys Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Ala Ser Leu Tyr Tyr Asp Tyr Gly Asp Ala Tyr
        115                 120                 125

Asp Tyr Trp Gly Gln Gly Thr Leu Val Thr Val Ser Ser Gly Ser Thr
    130                 135                 140

Ser Gly Ser Gly Lys Pro Gly Ser Gly Glu Gly Ser Thr Lys Gly Glu
145                 150                 155                 160

Ile Val Met Thr Gln Ser Pro Ala Thr Leu Ser Val Ser Pro Gly Glu
                165                 170                 175

Arg Ala Thr Leu Ser Cys Lys Ala Ser Gln Ser Val Glu Ser Asn Val
            180                 185                 190

Ala Trp Tyr Gln Gln Lys Pro Gly Gln Ala Pro Arg Ala Leu Ile Tyr
        195                 200                 205

Ser Ala Ser Leu Arg Phe Ser Gly Ile Pro Ala Arg Phe Ser Gly Ser
    210                 215                 220

Gly Ser Gly Thr Glu Phe Thr Leu Thr Ile Ser Ser Leu Gln Ser Glu
225                 230                 235                 240

Asp Phe Ala Val Tyr Tyr Cys Gln Gln Tyr Asn Asn Tyr Pro Leu Thr
                245                 250                 255

Phe Gly Ala Gly Thr Lys Leu Glu Leu Lys Glu Ser Lys Tyr Gly Pro
            260                 265                 270

Pro Cys Pro Pro Cys Pro Ala Pro Glu Phe Glu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

```
Thr Lys Pro Arg Glu Glu Gln Phe Asn Ser Thr Tyr Arg Val Val Ser
                340                 345                 350

Val Leu Thr Val Leu His Gln Asp Trp Leu Asn Gly Lys Glu Tyr Lys
            355                 360                 365

Cys Lys Val Ser Asn Lys Gly Leu Pro Ser Ser Ile Glu Lys Thr Ile
        370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Arg Leu Thr Val Asp Lys Ser Arg
450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Phe
                485                 490                 495

Trp Val Leu Val Val Val Gly Val Leu Ala Cys Tyr Ser Leu Leu
            500                 505                 510

Val Thr Val Ala Phe Ile Ile Phe Trp Val Arg Ser Lys Arg Ser Arg
        515                 520                 525

Leu Leu His Ser Asp Tyr Met Asn Met Thr Pro Arg Arg Pro Gly Pro
530                 535                 540

Thr Arg Lys His Tyr Gln Pro Tyr Ala Pro Pro Arg Asp Phe Ala Ala
545                 550                 555                 560

Tyr Arg Ser Leu Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
            660                 665                 670

Leu Pro Pro Arg
        675

<210> SEQ ID NO 61
<211> LENGTH: 566
<212> TYPE: PRT
<213> ORGANISM: Artificial Sequence
<220> FEATURE:
<223> OTHER INFORMATION: construct

<400> SEQUENCE: 61

Met Asp Phe Gln Val Gln Ile Phe Ser Phe Leu Leu Ile Ser Ala Ser
1               5                   10                  15
```

```
Val Ile Met Ser Arg Glu Val Gln Leu Val Glu Ser Gly Gly Leu
            20                  25                  30

Val Gln Pro Gly Gly Ser Leu Arg Leu Ser Cys Ala Ala Ser Gly Phe
        35                  40                  45

Thr Phe Ser Arg Tyr Trp Phe Ser Trp Val Arg Gln Ala Pro Gly Lys
    50                  55                  60

Gly Leu Val Trp Val Gly Glu Ile Asn Pro Ser Ser Thr Ile Asn
65                  70                  75                  80

Tyr Ala Pro Ser Leu Lys Asp Lys Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Ala Ser Leu Tyr Tyr Asp Tyr Gly Asp Ala Tyr
        115                 120                 125

Asp Tyr Trp Gly Gln Gly Thr Leu Val Thr Val Ser Ser Gly Ser Thr
    130                 135                 140

Ser Gly Ser Gly Lys Pro Gly Ser Gly Glu Gly Ser Thr Lys Gly Glu
145                 150                 155                 160

Ile Val Met Thr Gln Ser Pro Ala Thr Leu Ser Val Ser Pro Gly Glu
                165                 170                 175

Arg Ala Thr Leu Ser Cys Lys Ala Ser Gln Ser Val Glu Ser Asn Val
            180                 185                 190

Ala Trp Tyr Gln Gln Lys Pro Gly Gln Ala Pro Arg Ala Leu Ile Tyr
        195                 200                 205

Ser Ala Ser Leu Arg Phe Ser Gly Ile Pro Ala Arg Phe Ser Gly Ser
210                 215                 220

Gly Ser Gly Thr Glu Phe Thr Leu Thr Ile Ser Ser Leu Gln Ser Glu
225                 230                 235                 240

Asp Phe Ala Val Tyr Tyr Cys Gln Gln Tyr Asn Asn Tyr Pro Leu Thr
                245                 250                 255

Phe Gly Ala Gly Thr Lys Leu Glu Leu Lys Ser Lys Tyr Gly Pro
            260                 265                 270

Pro Cys Pro Pro Cys Pro Gly Gln Pro Arg Glu Pro Gln Val Tyr Thr
        275                 280                 285

Leu Pro Pro Ser Gln Glu Glu Met Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Arg Leu Thr Val Asp Lys
            340                 345                 350

Ser Arg Trp Gln Glu Gly Asn Val Phe Ser Cys Ser Val Met His Glu
        355                 360                 365

Ala Leu His Asn His Tyr Thr Gln Lys Ser Leu Ser Leu Ser Leu Gly
    370                 375                 380

Lys Phe Trp Val Leu Val Val Val Gly Gly Val Leu Ala Cys Tyr Ser
385                 390                 395                 400

Leu Leu Val Thr Val Ala Phe Ile Ile Phe Trp Val Arg Ser Lys Arg
                405                 410                 415

Ser Arg Leu Leu His Ser Asp Tyr Met Asn Met Thr Pro Arg Arg Pro
            420                 425                 430

Gly Pro Thr Arg Lys His Tyr Gln Pro Tyr Ala Pro Pro Arg Asp Phe
```

```
                435                 440                 445
Ala Ala Tyr Arg Ser Leu Arg Val Lys Phe Ser Arg Ser Ala Asp Ala
    450                 455                 460

Pro Ala Tyr Gln Gln Gly Gln Asn Gln Leu Tyr Asn Glu Leu Asn Leu
465                 470                 475                 480

Gly Arg Arg Glu Glu Tyr Asp Val Leu Asp Lys Arg Arg Gly Arg Asp
                485                 490                 495

Pro Glu Met Gly Gly Lys Pro Arg Arg Lys Asn Pro Gln Glu Gly Leu
                500                 505                 510

Tyr Asn Glu Leu Gln Lys Asp Lys Met Ala Glu Ala Tyr Ser Glu Ile
                515                 520                 525

Gly Met Lys Gly Glu Arg Arg Arg Gly Lys Gly His Asp Gly Leu Tyr
        530                 535                 540

Gln Gly Leu Ser Thr Ala Thr Lys Asp Thr Tyr Asp Ala Leu His Met
545                 550                 555                 560

Gln Ala Leu Pro Pro Arg
                565
```

<210> SEQ ID NO 62
<211> LENGTH: 459
<212> TYPE: PRT
<213> ORGANISM: Artificial Sequence
<220> FEATURE:
<223> OTHER INFORMATION: construct

<400> SEQUENCE: 62

```
Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Arg Tyr Trp Phe Ser Trp Val Arg Gln Ala Pro Gly Lys
        50                  55                  60

Gly Leu Val Trp Val Gly Glu Ile Asn Pro Ser Ser Ser Thr Ile Asn
65                  70                  75                  80

Tyr Ala Pro Ser Leu Lys Asp Lys Phe Thr Ile Ser Arg Asp Asn Ala
                85                  90                  95

Lys Asn Thr Leu Tyr Leu Gln Met Asn Ser Leu Arg Ala Glu Asp Thr
                100                 105                 110

Ala Val Tyr Tyr Cys Ala Ser Leu Tyr Tyr Asp Tyr Gly Asp Ala Tyr
            115                 120                 125

Asp Tyr Trp Gly Gln Gly Thr Leu Val Thr Val Ser Ser Gly Ser Thr
        130                 135                 140

Ser Gly Ser Gly Lys Pro Gly Ser Gly Glu Gly Ser Thr Lys Gly Glu
145                 150                 155                 160

Ile Val Met Thr Gln Ser Pro Ala Thr Leu Ser Val Ser Pro Gly Glu
                165                 170                 175

Arg Ala Thr Leu Ser Cys Lys Ala Ser Gln Ser Val Glu Ser Asn Val
                180                 185                 190

Ala Trp Tyr Gln Gln Lys Pro Gly Gln Ala Pro Arg Ala Leu Ile Tyr
            195                 200                 205

Ser Ala Ser Leu Arg Phe Ser Gly Ile Pro Ala Arg Phe Ser Gly Ser
        210                 215                 220

Gly Ser Gly Thr Glu Phe Thr Leu Thr Ile Ser Ser Leu Gln Ser Glu
```

```
            225                 230                 235                 240
Asp Phe Ala Val Tyr Tyr Cys Gln Gln Tyr Asn Asn Tyr Pro Leu Thr
                245                 250                 255
Phe Gly Ala Gly Thr Lys Leu Glu Leu Lys Glu Ser Lys Tyr Gly Pro
                260                 265                 270
Pro Cys Pro Pro Cys Pro Phe Trp Val Leu Val Val Val Gly Gly Val
            275                 280                 285
Leu Ala Cys Tyr Ser Leu Leu Val Thr Val Ala Phe Ile Ile Phe Trp
        290                 295                 300
Val Arg Ser Lys Arg Ser Arg Leu Leu His Ser Asp Tyr Met Asn Met
305                 310                 315                 320
Thr Pro Arg Arg Pro Gly Pro Thr Arg Lys His Tyr Gln Pro Tyr Ala
                325                 330                 335
Pro Pro Arg Asp Phe Ala Ala Tyr Arg Ser Leu Arg Val Lys Phe Ser
            340                 345                 350
Arg Ser Ala Asp Ala Pro Ala Tyr Gln Gln Gly Gln Asn Gln Leu Tyr
        355                 360                 365
Asn Glu Leu Asn Leu Gly Arg Arg Glu Glu Tyr Asp Val Leu Asp Lys
    370                 375                 380
Arg Arg Gly Arg Asp Pro Glu Met Gly Gly Lys Pro Arg Arg Lys Asn
385                 390                 395                 400
Pro Gln Glu Gly Leu Tyr Asn Glu Leu Gln Lys Asp Lys Met Ala Glu
                405                 410                 415
Ala Tyr Ser Glu Ile Gly Met Lys Gly Glu Arg Arg Arg Gly Lys Gly
            420                 425                 430
His Asp Gly Leu Tyr Gln Gly Leu Ser Thr Ala Thr Lys Asp Thr Tyr
        435                 440                 445
Asp Ala Leu His Met Gln Ala Leu Pro Pro Arg
    450                 455

<210> SEQ ID NO 63
<211> LENGTH: 680
<212> TYPE: PRT
<213> ORGANISM: Artificial Sequence
<220> FEATURE:
<223> OTHER INFORMATION: construct

<400> SEQUENCE: 63

Met Asp Phe Gln Val Gln Ile Phe Ser Phe Leu Leu Ile Ser Ala Ser
1               5                   10                  15
Val Ile Met Ser Arg Glu Val Gln Leu Val Glu Ser Gly Gly Gly Leu
            20                  25                  30
Val Gln Pro Gly Gly Ser Leu Arg Leu Ser Cys Ala Ala Ser Gly Phe
        35                  40                  45
Thr Phe Ser Arg Tyr Trp Phe Ser Trp Val Arg Gln Ala Pro Gly Lys
    50                  55                  60
Gly Leu Val Trp Val Gly Glu Ile Asn Pro Ser Ser Thr Ile Asn
65                  70                  75                  80
Tyr Ala Pro Ser Leu Lys Asp Lys Phe Thr Ile Ser Arg Asp Asn Ala
                85                  90                  95
Lys Asn Thr Leu Tyr Leu Gln Met Asn Ser Leu Arg Ala Glu Asp Thr
            100                 105                 110
Ala Val Tyr Tyr Cys Ala Ser Leu Tyr Asp Tyr Gly Asp Ala Tyr
        115                 120                 125
Asp Tyr Trp Gly Gln Gly Thr Leu Val Thr Val Ser Ser Gly Ser Thr
```

-continued

```
              130                 135                 140
Ser Gly Ser Gly Lys Pro Gly Ser Gly Glu Gly Ser Thr Lys Gly Glu
145                 150                 155                 160

Ile Val Met Thr Gln Ser Pro Ala Thr Leu Ser Val Ser Pro Gly Glu
                165                 170                 175

Arg Ala Thr Leu Ser Cys Lys Ala Ser Gln Ser Val Glu Ser Asn Val
            180                 185                 190

Ala Trp Tyr Gln Gln Lys Pro Gly Gln Ala Pro Arg Ala Leu Ile Tyr
        195                 200                 205

Ser Ala Ser Leu Arg Phe Ser Gly Ile Pro Ala Arg Phe Ser Gly Ser
210                 215                 220

Gly Ser Gly Thr Glu Phe Thr Leu Thr Ile Ser Ser Leu Gln Ser Glu
225                 230                 235                 240

Asp Phe Ala Val Tyr Tyr Cys Gln Gln Tyr Asn Asn Tyr Pro Leu Thr
                245                 250                 255

Phe Gly Ala Gly Thr Lys Leu Glu Leu Lys Pro Ala Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
    290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Ser Leu
                485                 490                 495

Ser Pro Gly Lys Lys Ile Tyr Ile Trp Ala Pro Leu Ala Gly Thr Cys
            500                 505                 510

Gly Val Leu Leu Leu Ser Leu Val Ile Thr Leu Tyr Cys Lys Arg Gly
        515                 520                 525

Arg Lys Lys Leu Leu Tyr Ile Phe Lys Gln Pro Phe Met Arg Pro Val
530                 535                 540

Gln Thr Thr Gln Glu Glu Asp Gly Cys Ser Cys Arg Phe Pro Glu Glu
545                 550                 555                 560
```

```
Glu Gly Gly Cys Glu Leu Leu Arg Val Lys Phe Ser Arg Ser Ala
            565                 570                 575

Asp Ala Pro Ala Tyr Gln Gly Gln Asn Gln Leu Tyr Asn Glu Leu
            580                 585                 590

Asn Leu Gly Arg Arg Glu Tyr Asp Val Leu Asp Lys Arg Arg Gly
            595                 600                 605

Arg Asp Pro Glu Met Gly Gly Lys Pro Arg Arg Lys Asn Pro Gln Glu
610                 615                 620

Gly Leu Tyr Asn Glu Leu Gln Lys Asp Lys Met Ala Glu Ala Tyr Ser
625                 630                 635                 640

Glu Ile Gly Met Lys Gly Glu Arg Arg Arg Gly Lys Gly His Asp Gly
            645                 650                 655

Leu Tyr Gln Gly Leu Ser Thr Ala Thr Lys Asp Thr Tyr Asp Ala Leu
            660                 665                 670

His Met Gln Ala Leu Pro Pro Arg
            675                 680

<210> SEQ ID NO 64
<211> LENGTH: 680
<212> TYPE: PRT
<213> ORGANISM: Artificial Sequence
<220> FEATURE:
<223> OTHER INFORMATION: construct

<400> SEQUENCE: 64

Met Asp Phe Gln Val Gln Ile Phe Ser Phe Leu Leu Ile Ser Ala Ser
1               5                   10                  15

Val Ile Met Ser Arg Glu Ile Val Met Thr Gln Ser Pro Ala Thr Leu
            20                  25                  30

Ser Val Ser Pro Gly Glu Arg Ala Thr Leu Ser Cys Lys Ala Ser Gln
            35                  40                  45

Ser Val Glu Ser Asn Val Ala Trp Tyr Gln Gln Lys Pro Gly Gln Ala
        50                  55                  60

Pro Arg Ala Leu Ile Tyr Ser Ala Ser Leu Arg Phe Ser Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Asn Asn Tyr Pro Leu Thr Phe Gly Ala Gly Thr Lys Leu Glu Leu Lys
        115                 120                 125

Gly Ser Thr Ser Gly Ser Gly Lys Pro Gly Ser Gly Glu Gly Ser Thr
130                 135                 140

Lys Gly Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Thr Phe Ser
                165                 170                 175

Arg Tyr Trp Phe Ser Trp Val Arg Gln Ala Pro Gly Lys Gly Leu Val
            180                 185                 190

Trp Val Gly Glu Ile Asn Pro Ser Ser Thr Ile Asn Tyr Ala Pro
        195                 200                 205

Ser Leu Lys Asp Lys Phe Thr Ile Ser Arg Asp Asn Ala Lys Asn Thr
210                 215                 220

Leu Tyr Leu Gln Met Asn Ser Leu Arg Ala Glu Asp Thr Ala Val Tyr
225                 230                 235                 240
```

```
Tyr Cys Ala Ser Leu Tyr Tyr Asp Tyr Gly Asp Ala Tyr Asp Tyr Trp
                245                 250                 255

Gly Gln Gly Thr Leu Val Thr Val Ser Ser Pro Ala Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
    290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Ser Pro Gly Lys Lys Ile Tyr Ile Trp Ala Pro Leu Ala Gly Thr Cys
            500                 505                 510

Gly Val Leu Leu Leu Ser Leu Val Ile Thr Leu Tyr Cys Lys Arg Gly
        515                 520                 525

Arg Lys Lys Leu Leu Tyr Ile Phe Lys Gln Pro Phe Met Arg Pro Val
    530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Leu Arg Val Lys Phe Ser Arg Ser Ala
                565                 570                 575

Asp Ala Pro Ala Tyr Gln Gln Gly Gln Asn Gln Leu Tyr Asn Glu Leu
            580                 585                 590

Asn Leu Gly Arg Arg Glu Glu Tyr Asp Val Leu Asp Lys Arg Arg Gly
        595                 600                 605

Arg Asp Pro Glu Met Gly Gly Lys Pro Arg Arg Lys Asn Pro Gln Glu
    610                 615                 620

Gly Leu Tyr Asn Glu Leu Gln Lys Asp Lys Met Ala Glu Ala Tyr Ser
625                 630                 635                 640

Glu Ile Gly Met Lys Gly Glu Arg Arg Arg Gly Lys Gly His Asp Gly
                645                 650                 655
```

-continued

Leu Tyr Gln Gly Leu Ser Thr Ala Thr Lys Asp Thr Tyr Asp Ala Leu
            660                 665                 670

His Met Gln Ala Leu Pro Pro Arg
            675                 680

<210> SEQ ID NO 65
<211> LENGTH: 680
<212> TYPE: PRT
<213> ORGANISM: Artificial Sequence
<220> FEATURE:
<223> OTHER INFORMATION: construct

<400> SEQUENCE: 65

Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Arg Tyr Trp Phe Ser Trp Val Arg Gln Ala Pro Gly Lys
    50                  55                  60

Gly Leu Val Trp Val Gly Glu Ile Asn Pro Ser Ser Thr Ile Asn
65                  70                  75                  80

Tyr Ala Pro Ser Leu Lys Asp Lys Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Ala Ser Leu Tyr Tyr Asp Tyr Gly Asp Ala Tyr
        115                 120                 125

Asp Tyr Trp Gly Gln Gly Thr Leu Val Thr Val Ser Ser Gly Ser Thr
    130                 135                 140

Ser Gly Ser Gly Lys Pro Gly Ser Gly Glu Gly Ser Thr Lys Gly Glu
145                 150                 155                 160

Ile Val Met Thr Gln Ser Pro Ala Thr Leu Ser Val Ser Pro Gly Glu
                165                 170                 175

Arg Ala Thr Leu Ser Cys Lys Ala Ser Gln Ser Val Glu Ser Asn Val
            180                 185                 190

Ala Trp Tyr Gln Gln Lys Pro Gly Gln Ala Pro Arg Ala Leu Ile Tyr
        195                 200                 205

Ser Ala Ser Leu Arg Phe Ser Gly Ile Pro Ala Arg Phe Ser Gly Ser
    210                 215                 220

Gly Ser Gly Thr Glu Phe Thr Leu Thr Ile Ser Ser Leu Gln Ser Glu
225                 230                 235                 240

Asp Phe Ala Val Tyr Tyr Cys Gln Gln Tyr Asn Asn Tyr Pro Leu Thr
                245                 250                 255

Phe Gly Ala Gly Thr Lys Leu Glu Leu Lys Pro Ala Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
    290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Gln Tyr Asn Ser Thr Tyr
                340                 345                 350

Arg Val Val Ser Val Leu Thr Val Leu His Gln Asp Trp Leu Asn Gly
            355                 360                 365

Lys Glu Tyr Lys Cys Lys Val Ser Asn Lys Ala Leu Pro Ala Pro Ile
        370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Lys Ile Tyr Ile Trp Ala Pro Leu Ala Gly Thr Cys
            500                 505                 510

Gly Val Leu Leu Leu Ser Leu Val Ile Thr Leu Tyr Cys Lys Arg Gly
        515                 520                 525

Arg Lys Lys Leu Leu Tyr Ile Phe Lys Gln Pro Phe Met Arg Pro Val
530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Leu Arg Val Lys Phe Ser Arg Ser Ala
                565                 570                 575

Asp Ala Pro Ala Tyr Gln Gln Gly Gln Asn Gln Leu Tyr Asn Glu Leu
            580                 585                 590

Asn Leu Gly Arg Arg Glu Glu Tyr Asp Val Leu Asp Lys Arg Arg Gly
        595                 600                 605

Arg Asp Pro Glu Met Gly Gly Lys Pro Arg Arg Lys Asn Pro Gln Glu
610                 615                 620

Gly Leu Tyr Asn Glu Leu Gln Lys Asp Lys Met Ala Glu Ala Tyr Ser
625                 630                 635                 640

Glu Ile Gly Met Lys Gly Glu Arg Arg Arg Gly Lys Gly His Asp Gly
                645                 650                 655

Leu Tyr Gln Gly Leu Ser Thr Ala Thr Lys Asp Thr Tyr Asp Ala Leu
            660                 665                 670

His Met Gln Ala Leu Pro Pro Arg
        675                 680

<210> SEQ ID NO 66
<211> LENGTH: 360
<212> TYPE: DNA
<213> ORGANISM: Artificial Sequence
<220> FEATURE:
<223> OTHER INFORMATION: VH

<400> SEQUENCE: 66
gaggtgcagc tggtggaatc tggcggagga ctggtgcagc ctggcggctc tctgagactg     60
tcttgtgccg ccagcggctt caccttcagc cggtactggt tagctgggt gcgccaggcc    120

```
cctggcaagg gactcgtgtg ggtgggagag atcaaccca gcagcagcac catcaactac    180
gcccccagcc tgaaggacaa gttcaccatc agcagagaca cgccaagaa caccctgtac    240 ctgcagatga acagcctgcg ggccgaggac accgccgtgt actattgtgc cagcctgtac    300
tacgactacg cgacgccta cgattactgg ggccagggca cactggtgac tgttagctcc    360
```

<210> SEQ ID NO 67
<211> LENGTH: 321
<212> TYPE: DNA
<213> ORGANISM: Artificial Sequence
<220> FEATURE:
<223> OTHER INFORMATION: VL

<400> SEQUENCE: 67

```
gagatcgtga tgacacagag ccctgccacc ctgagcgtgt ccccaggcga aagagctacc     60
ctgagctgca aggccagcca gagcgtggaa agcaacgtgg cctggtatca gcagaagccc    120
ggacaggctc ctcgggccct gatctacagc gccagcctga gattcagcgg catccccgcc    180
aggtttagcg gctctggcag cggcaccgag ttcaccctga caatcagcag cctgcagagc    240
gaggactttg ccgtgtatta ctgccagcag tacaacaact accccctgac cttcggagcc    300
ggcaccaagc tggagctgaa g                                              321
```

<210> SEQ ID NO 68
<211> LENGTH: 360
<212> TYPE: DNA
<213> ORGANISM: Artificial Sequence
<220> FEATURE:
<223> OTHER INFORMATION: VH

<400> SEQUENCE: 68

```
gaagtgcagc tggtcgaatc tggaggaggc ctggttcagc ctggtggcag ccttaggctc     60
tcttgtgcag cctctggctt taccttctca cggtattggt tcagctgggt gagacaggct    120
ccagggaaag gtctggtgtg ggtagggag ataaaccca gcagcagcac gatcaactat    180
gctccgtcac tgaaagacaa gttcaccatt ccccgcgata tgccaagaa cactctctac    240 ttgcagatga attcccttcg agccgaggat acagcggtgt actactgcgc cagtctgtac    300
tacgactatg ggacgcata cgactattgg ggacaaggca cactggtgac tgttagctcc    360
```

<210> SEQ ID NO 69
<211> LENGTH: 321
<212> TYPE: DNA
<213> ORGANISM: Artificial Sequence
<220> FEATURE:
<223> OTHER INFORMATION: VL

<400> SEQUENCE: 69

```
gagatcgtga tgacccagtc tcctgctacc ctgagcgttt ctcccggtga agggccaca     60 ctcagctgca aagcctctca aagcgtggag agcaatgtcg cctggtatca gcagaaacct    120
ggccaagctc cgagagcact gatctattcc gcgtcattgc gcttttccgg cataccagca    180
cggtttagtg gctcagggag tgggactgag ttcactctga cgattagctc ccttcagtca    240
gaggatttcg ccgtgtacta ctgtcagcag tacaacaact atcccctcac attcggagct    300
ggaaccaagc tggaactgaa g                                              321
```

<210> SEQ ID NO 70
<211> LENGTH: 63
<212> TYPE: DNA

```
<213> ORGANISM: Artificial Sequence
<220> FEATURE:
<223> OTHER INFORMATION: leader

<400> SEQUENCE: 70
atggatttcc aggtgcagat cttcagcttc ctgctgatct ccgccagcgt gatcatgagc      60
cgc                                                                    63

<210> SEQ ID NO 71
<211> LENGTH: 63
<212> TYPE: DNA
<213> ORGANISM: Artificial Sequence
<220> FEATURE:
<223> OTHER INFORMATION: leader

<400> SEQUENCE: 71
atgcttctcc tggtgacaag ccttctgctc tgtgagttac cacacccagc attcctcctg      60
atc                                                                    63

<210> SEQ ID NO 72
<211> LENGTH: 54
<212> TYPE: DNA
<213> ORGANISM: Artificial Sequence
<220> FEATURE:
<223> OTHER INFORMATION: linker

<400> SEQUENCE: 72
ggcagcacca gcggctccgg caagcctggc tctggcgagg cagcacaaa ggga             54

<210> SEQ ID NO 73
<211> LENGTH: 51
<212> TYPE: DNA
<213> ORGANISM: Artificial Sequence
<220> FEATURE:
<223> OTHER INFORMATION: linker

<400> SEQUENCE: 73
tctagcggcg gaggcggatc tggcggggga ggatctgggg gaggcggctc t               51

<210> SEQ ID NO 74
<211> LENGTH: 702
<212> TYPE: DNA
<213> ORGANISM: Artificial Sequence
<220> FEATURE:
<223> OTHER INFORMATION: spacer

<400> SEQUENCE: 74
cctgccgagc ctaagagccc cgacaagacc cacacctgtc ccccttgtcc tgcccctcca      60
gtggctggcc ctagcgtgtt cctgttcccc ccaaagccca aggataccct gatgatcgcc     120
cggacccccg aagtcacatg cgtggtggtg gacgtgagcc acgaagaccc tgaggtcaag     180
ttcaactggt acgtggacgg cgtggaggtg cataatgcca agacaaagcc gcggaggag      240 cagtacaaca gcacgtaccg tgtggtcagc gtcctcaccg tcctgcacca ggactggctg     300
aatggcaagg agtacaagtg caaggtctcc aacaaagccc tcccagcccc catcgagaaa     360
accatctcca aagccaaagg gcagcccga gaaccacagg tgtacaccct gcccccatcc      420
cgggatgagc tgaccaagaa ccaggtcagc ctgacctgcc tggtcaaagg cttctatccc     480
agcgacatcg ccgtggagtg ggagagcaat gggcagccgg agaacaacta caagaccacg     540
cctcccgtgc tggactccga cggctccttc ttcctctaca gcaagctcac cgtggacaag     600
agcaggtggc agcaggggaa cgtcttctca tgctccgtga tgcatgaggc tctgcacaac     660
```

```
cactacacgc agaagagcct ctccctgtct ccgggtaaaa aa                 702
```

<210> SEQ ID NO 75
<211> LENGTH: 705
<212> TYPE: DNA
<213> ORGANISM: Artificial Sequence
<220> FEATURE:
<223> OTHER INFORMATION: spacer

<400> SEQUENCE: 75

```
cctgccgagc ctaagagccc cgacaagacc cacacctgtc ccccttgtcc tgcccctcca    60
gtggctggcc ctagcgtgtt cctgttcccc ccaaagccca aggataccct gatgatcgcc   120
cggacccccg aagtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc tcccagcccc catcgagaaa   360
accatctcca aagccaaagg gcagccccga gaaccacagg tgtacaccct gcccccatcc   420
cgggatgagc tgaccaagaa ccaggtgtcc ctgacctgcc tcgtgaaggg cttctacccc   480
tccgatatcg ccgtggaatg ggagagcaat ggccagcccg agaacaacta caagaccacc   540
ccccctgtgc tggacagcga cggctcattc ttcctgtaca gcaagctgac agtggacaag   600
agccggtggc agcagggcaa cgtgttcagc tgcagcgtga tgcacgaggc tctgcacaac   660
cactacaccc agaagtccct gagcagcctg agcccaggca agaag              705
```

<210> SEQ ID NO 76
<211> LENGTH: 687
<212> TYPE: DNA
<213> ORGANISM: Artificial Sequence
<220> FEATURE:
<223> OTHER INFORMATION: spacer

<400> SEQUENCE: 76

```
gagagcaagt acggccctcc ctgcccccct tgccctgccc ccgagttcga gggcggaccc    60
agcgtgttcc tgttcccccc caagcccaag gacaccctga tgatcagccg gacccccgag   120
gtgacctgcg tggtggtgga cgtgagccag gaagatcccg aggtccagtt caattggtac   180
gtggacggcg tggaagtgca caacgccaag accaagccca gaggaacac gttcaacagc   240
acctaccggg tggtgtctgt gctgaccgtg ctgcaccagg actggctgaa cggcaaagaa   300
tacaagtgca aggtgtccaa caagggcctg cccagcagca tcgaaaagac catcagcaag   360
gccaagggcc agcctcgcga gccccaggtg tacaccctgc ctccctccca ggaagagatg   420
accaagaacc aggtgtccct gacctgcctg gtgaagggct tctacccag cgacatcgcc   480
gtggagtggg agagcaacgg ccagcctgag aacaactaca gaccacccc tcccgtgctg   540
gacagcgacg gcagcttctt cctctacagc cggctgaccg tggacaagag ccggtggcag   600
gaaggcaacg tctttagctg cagcgtgatg cacgaggccc tgcacaacca ctacacccag   660
aagagcctga gcctgtccct gggcaag                                  687
```

<210> SEQ ID NO 77
<211> LENGTH: 357
<212> TYPE: DNA
<213> ORGANISM: Artificial Sequence
<220> FEATURE:
<223> OTHER INFORMATION: spacer

```
<400> SEQUENCE: 77
gagagcaagt acggccctcc ctgcccccct tgccctggcc agcctcgcga gccccaggtg    60
tacaccctgc ctccctccca ggaagagatg accaagaacc aggtgtccct gacctgcctg   120
gtgaagggct tctacccag cgacatcgcc gtggagtggg agagcaacgg ccagcctgag    180
aacaactaca agaccacccc tcccgtgctg gacagcgacg gcagcttctt cctctacagc   240
cggctgaccg tggacaagag ccggtggcag gaaggcaacg tctttagctg cagcgtgatg   300
cacgaggccc tgcacaacca ctacacccag aagagcctga gcctgtccct gggcaag     357

<210> SEQ ID NO 78
<211> LENGTH: 36
<212> TYPE: DNA
<213> ORGANISM: Artificial Sequence
<220> FEATURE:
<223> OTHER INFORMATION: spacer

<400> SEQUENCE: 78
gagagcaagt acggccctcc ctgcccccct tgccct                              36

<210> SEQ ID NO 79
<211> LENGTH: 72
<212> TYPE: DNA
<213> ORGANISM: Artificial Sequence
<220> FEATURE:
<223> OTHER INFORMATION: transmembrane

<400> SEQUENCE: 79
atctacatct gggcccctct ggccggcacc tgtggcgtgc tgctgctgtc tctcgtgatc    60
acactgtact gc                                                        72

<210> SEQ ID NO 80
<211> LENGTH: 81
<212> TYPE: DNA
<213> ORGANISM: Artificial Sequence
<220> FEATURE:
<223> OTHER INFORMATION: transmembrane

<400> SEQUENCE: 80
ttttgggtgc tggtggtggt tggtggagtc ctggcttgct atagcttgct agtaacagtg    60
gcctttatta ttttctgggt g                                              81

<210> SEQ ID NO 81
<211> LENGTH: 126
<212> TYPE: DNA
<213> ORGANISM: Artificial Sequence
<220> FEATURE:
<223> OTHER INFORMATION: intracellular

<400> SEQUENCE: 81
aagcggggca gaaagaagct gctgtacatc ttcaagcagc ccttcatgcg gcccgtgcag    60
accacccagg aagaggacgg ctgctcctgc agattccccg aggaagaaga aggcggctgc   120
gagctg                                                              126

<210> SEQ ID NO 82
<211> LENGTH: 123
<212> TYPE: DNA
<213> ORGANISM: Artificial Sequence
<220> FEATURE:
<223> OTHER INFORMATION: intracellular

<400> SEQUENCE: 82
```

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 83
<211> LENGTH: 123
<212> TYPE: DNA
<213> ORGANISM: Artificial Sequence
<220> FEATURE:
<223> OTHER INFORMATION: intracellular

<400> SEQUENCE: 83
aggagtaaga ggagcaggct cctgcacagt gactacatga acatgactcc ccgtcgaccc    60
gggcccaccc gcaagcatta ccagccctat gccccaccac gcgacttcgc agcctatcgc   120
tcc                                                                 123

<210> SEQ ID NO 84
<211> LENGTH: 342
<212> TYPE: DNA
<213> ORGANISM: Artificial Sequence
<220> FEATURE:
<223> OTHER INFORMATION: intracellular

<400> SEQUENCE: 84
ctgagagtga agttcagcag gagcgcagac gcccccgcgt accagcaggg ccagaaccag    60
ctctataacg agctcaatct aggacgaaga gaggagtacg atgttttgga caagagacgt   120
ggccgggacc ctgagatggg gggaaagccg agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg ccccctcgct ga                      342

<210> SEQ ID NO 85
<211> LENGTH: 339
<212> TYPE: DNA
<213> ORGANISM: Artificial Sequence
<220> FEATURE:
<223> OTHER INFORMATION: intracellular

<400> SEQUENCE: 85
ctgcgcgtga agttttctag aagcgccgac gcccctgcct accagcaggg ccagaaccag    60
ctgtacaacg agctgaacct gggcagacgg gaagagtacg acgtgctgga taagcggaga   120
ggccgggacc ctgagatggg cggcaagcct agaagaaaga accccagga aggcctgtat    180 aacgaactgc agaaagacaa gatggccgag gcctacagcg agatcggaat gaagggcgag   240
cggagaagag gcaagggcca cgatggactg taccagggcc tgagcaccgc caccaaggac   300
acctatgacg ccctgcacat gcaggctctg ccccccaga                          339

<210> SEQ ID NO 86
<211> LENGTH: 2055
<212> TYPE: DNA
<213> ORGANISM: Artificial Sequence
<220> FEATURE:
<223> OTHER INFORMATION: construct

<400> SEQUENCE: 86
atggatttcc aggtgcagat cttcagcttc ctgctgatct ccgccagcgt gatcatgagc    60
```

| | |
|---|---|
| cgcgaggtgc agctggtgga atctggcgga ggactggtgc agcctggcgg ctctctgaga | 120 |
| ctgtcttgtg ccgccagcgg cttcaccttc agccggtact ggtttagctg ggtgcgccag | 180 |
| gcccctggca agggactcgt gtgggtggga gagatcaacc ccagcagcag caccatcaac | 240 |
| tacgccccca gcctgaagga caagttcacc atcagcagag acaacgccaa gaacaccctg | 300 |
| tacctgcaga tgaacagcct gcgggccgag gacaccgccg tgtactattg tgccagcctg | 360 |
| tactacgact acggcgacgc ctacgattac tggggccagg gcactggt gactgttagc | 420 |
| tccggcagca ccagcggctc cggcaagcct ggctctggcg agggcagcac aaagggagag | 480 |
| atcgtgatga cacagagccc tgccaccctg agcgtgtccc caggcgaaag agctaccctg | 540 |
| agctgcaagg ccagccagag cgtggaaagc aacgtggcct ggtatcagca aagcccgga | 600 |
| caggctcctc gggccctgat ctacagcgcc agcctgagat tcagcggcat ccccgccagg | 660 |
| tttagcggct ctggcagcgg caccgagttc accctgacaa tcagcagcct gcagagcgag | 720 |
| gactttgccg tgtattactg ccagcagtac aacaactacc ccctgacctt cggagccggc | 780 |
| accaagctgg agctgaagcc tgccgagcct aagagccccg acaagaccca cctgtccc | 840 |
| ccttgtcctg cccctccagt ggctggccct agcgtgttcc tgttcccccc aaagcccaag | 900 |
| gataccctga tgatcgcccg gaccccccgaa gtcacatgcg tggtggtgga cgtgagccac | 960 |
| gaagaccctg aggtcaagtt caactggtac gtggacggcg tggaggtgca taatgccaag | 1020 |
| acaaagccgc gggaggagca gtacaacagc acgtaccgtg tggtcagcgt cctcaccgtc | 1080 |
| ctgcaccagg actggctgaa tggcaaggag tacaagtgca aggtctccaa caaagccctc | 1140 |
| ccagccccca tcgagaaaac catctccaaa gccaaaggc agccccgaga accacaggtg | 1200 |
| tacaccctgc cccatcccg ggatgagctg accaagaacc aggtcagcct gacctgcctg | 1260 |
| gtcaaaggct tctatcccag cgacatcgcc gtggagtggg agagcaatgg gcagccggag | 1320 |
| aacaactaca agaccacgcc tcccgtgctg gactccgacg gctccttctt cctctacagc | 1380 |
| aagctcaccg tggacaagag caggtggcag caggggaacg tcttctcatg ctccgtgatg | 1440 |
| catgaggctc tgcacaacca ctacacgcag aagagcctct ccctgtctcc gggtaaaaaa | 1500 |
| gatcccaaat tttgggtgct ggtggtggtt ggtggagtcc tggcttgcta tagcttgcta | 1560 |
| gtaacagtgg cctttattat tttctgggtg aggagtaaga ggagcaggct cctgcacagt | 1620 |
| gactacatga acatgactcc ccgccgcccc gggcccaccc gcaagcatta ccagccctat | 1680 |
| gcccaccac gcgacttcgc agcctatcgc tccctgagag tgaagttcag caggagcgca | 1740 |
| gacgccccg cgtaccagca gggccagaac cagctctata cgagctcaa tctaggacga | 1800 |
| agagaggagt acgatgtttt ggacaagaga cgtggccggg accctgagat gggggggaaag | 1860 |
| ccgagaagga agaaccctca ggaaggcctg tacaatgaac tgcagaaaga taagatggcg | 1920 |
| gaggcctaca gtgagattgg gatgaaaggc gagcgccgga ggggcaaggg gcacgatggc | 1980 |
| ctttaccagg gtctcagtac agccaccaag gacacctacg acgccttca catgcaggcc | 2040 |
| ctgccccctc gctga | 2055 |

<210> SEQ ID NO 87
<211> LENGTH: 2055
<212> TYPE: DNA
<213> ORGANISM: Artificial Sequence
<220> FEATURE:
<223> OTHER INFORMATION: construct

<400> SEQUENCE: 87

| | |
|---|---|
| atggatttcc aggtgcagat cttcagcttc ctgctgatct ccgccagcgt gatcatgagc | 60 |

```
cgcgagatcg tgatgacaca gagccctgcc accctgagcg tgtccccagg cgaaagagct    120
accctgagct gcaaggccag ccagagcgtg aaaagcaacg tggcctggta tcagcagaag    180
cccggacagg ctcctcgggc cctgatctac agcgccagcc tgagattcag cggcatcccc    240
gccaggttta gcggctctgg cagcggcacc gagttcaccc tgacaatcag cagcctgcag    300
agcgaggact tgccgtgtat tactgccag cagtacaaca actacccct gaccttcgga    360 gccggcacca gctggagct gaagggcagc accagcggct ccggcaagcc tggctctggc    420
gagggcagca caaagggaga ggtgcagctg gtggaatctg gcggaggact ggtgcagcct    480
ggcggctctc tgagactgtc ttgtgccgcc agcggcttca ccttcagccg gtactggttt    540
agctgggtgc gccaggcccc tggcaaggga ctcgtgtggg tgggagagat caaccccagc    600
agcagcacca tcaactacgc ccccagcctg aaggacaagt tcaccatcag cagagacaac    660
gccaagaaca ccctgtacct gcagatgaac agcctgcggg ccgaggacac cgccgtgtac    720
tattgtgcca gcctgtacta cgactacggc gacgcctacg attactgggg ccagggcaca    780
ctggtgactg ttagctcccc tgccgagcct aagagccccg acaagaccca cacctgtccc    840
ccttgtcctg cccctccagt ggctggccct agcgtgttcc tgttcccccc aaagcccaag    900
gatacccgta tgatcgcccg gaccccgaa gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaagggg ccccgaga ccacaggtg      1200 tacaccctgc ccccatcccg ggatgagctg accaagaacc aggtcagcct gacctgcctg   1260
gtcaaaggct tctatcccag cgacatcgcc gtggagtggg agagcaatgg gcagccggag   1320
aacaactaca agaccacgcc tcccgtgctg gactccgacg gctccttctt cctctacagc   1380
aagctcaccg tggacaagag caggtggcag caggggaacg tcttctcatg ctccgtgatg   1440
catgaggctc tgcacaacca ctacacgcag aagagcctct ccctgtctcc gggtaaaaaa   1500
gatcccaaat tttgggtgct ggtggtggtt ggtggagtcc tggcttgcta tagcttgcta   1560
gtaacagtgg cctttattat tttctggggtg aggagtaaga ggagcaggct cctgcacagt   1620
gactacatga acatgactcc ccgccgcccc gggcccaccc gcaagcatta ccagccctat   1680
gccccaccac gcgacttcgc agcctatcgc tccctgagag tgaagttcag caggagcgca   1740
gacgcccccg cgtaccagca gggccagaac cagctctata cgagctcaa tctaggacga   1800 agagaggagt acgatgtttt ggacaagaga cgtggccggg accctgagat gggggggaaag   1860 ccgagaagga agaaccctca ggaaggcctg tacaatgaac tgcagaaaga taagatggcg    1920
gaggcctaca gtgagattgg gatgaaaggc gagcgccgga ggggcaaggg gcacgatggc    1980
ctttaccagg gtctcagtac agccaccaag gacacctacg acgcccttca catgcaggcc    2040
ctgccccctc gctga                                                   2055
```

<210> SEQ ID NO 88
<211> LENGTH: 2055
<212> TYPE: DNA
<213> ORGANISM: Artificial Sequence
<220> FEATURE:
<223> OTHER INFORMATION: construct

<400> SEQUENCE: 88

```
atggatttcc aggtgcagat cttcagcttc ctgctgatct ccgccagcgt gatcatgagc    60
cgcgaagtgc agctggtcga atctggagga ggcctggttc agcctggtgg cagccttagg   120
ctctcttgtg cagcctctgg ctttaccttc tcacggtatt ggttcagctg ggtgagacag   180
gctccaggga aggtctggt gtgggtaggg agataaacc ccagcagcag cacgatcaac     240
tatgctccgt cactgaaaga caagttcacc atttcccgcg ataatgccaa gaacactctc   300
tacttgcaga tgaattccct tcgagccgag atacagcgg tgtactactg cgccagtctg    360
tactacgact atggggacgc atacgactat tggggacaag gcacactggt gactgttagc   420
tccggcagca ccagcggctc cggcaagcct ggctctggcg agggcagcac aaagggagag   480
atcgtgatga cccagtctcc tgctaccctg agcgtttctc ccggtgaaag gccacactc    540 agctgcaaag cctctcaaag cgtggagagc aatgtcgcct ggtatcagca gaaacctggc   600
caagctccga gagcactgat ctattccgcg tcattgcgct tttccggcat accagcacgg   660
tttagtggct cagggagtgg gactgagttc actctgacga ttagctccct tcagtcagag   720
gatttcgccg tgtactactg tcagcagtac aacaactatc ccctcacatt cggagctgga   780
accaagctgg aactgaagcc tgccgagcct aagagccccg acaagaccca cacctgtccc   840
ccttgtcctg cccctccagt ggctggccct agcgtgttcc tgttcccccc aaagcccaag   900 gatacccctga tgatcgcccg gaccccgaa gtcacatgcg tggtggtgga cgtgagccac    960
gaagaccctg aggtcaagtt caactggtac gtggacggcg tggaggtgca taatgccaag  1020
acaaagccgc gggaggagca gtacaacagc acgtaccgtg tggtcagcgt cctcaccgtc  1080
ctgcaccagg actggctgaa tggcaaggag tacaagtgca aggtctccaa caaagccctc  1140
ccagccccca tcgagaaaac catctccaaa gccaagggc agccccgaga accacaggtg   1200
tacaccctgc cccatcccg ggatgagctg accaagaacc aggtcagcct gacctgcctg   1260
gtcaaaggct tctatcccag cgacatcgcc gtggagtggg agagcaatgg gcagccggag  1320
aacaactaca agaccacgcc tcccgtgctg gactccgacg gctccttctt cctctacagc  1380
aagctcaccg tggacaagag caggtggcag caggggaacg tcttctcatg ctccgtgatg  1440
catgaggctc tgcacaacca ctacacgcag aagagcctct ccctgtctcc gggtaaaaaa  1500
gatcccaaat tttgggtgct ggtggtggtt ggtggagtcc tggcttgcta tagcttgcta  1560
gtaacagtgg cctttattat tttctgggtg aggagtaaga ggagcaggct cctgcacagt  1620
gactacatga acatgactcc ccgccgcccc gggcccaccc gcaagcatta ccagccctat  1680
gccccaccac gcgacttcgc agcctatcgc tccctgagag tgaagttcag caggagcgca  1740
gacgcccccg cgtaccagca gggccagaac cagctctata cgagctcaa tctaggacga   1800 agagaggagt acgatgtttt ggacaagaga cgtggccggg accctgagat gggggggaaag  1860 ccgagaagga agaaccctca ggaaggcctg tacaatgaac tgcagaaaga taagatggcg  1920
gaggcctaca gtgagattgg gatgaaaggc gagcgccgga ggggcaaggg gcacgatggc  1980
ctttaccagg gtctcagtac agccaccaag gacacctacg acgcccttca catgcaggcc  2040
ctgccccctc gctga                                                    2055
```

<210> SEQ ID NO 89
<211> LENGTH: 2031
<212> TYPE: DNA
<213> ORGANISM: Artificial Sequence
<220> FEATURE:
<223> OTHER INFORMATION: construct

<400> SEQUENCE: 89

```
atggatttcc aggtgcagat cttcagcttc ctgctgatct ccgccagcgt gatcatgagc      60
cgcgaggtgc agctggtgga atctggcgga ggactggtgc agcctggcgg ctctctgaga     120
ctgtcttgtg ccgccagcgg cttcaccttc agccggtact ggtttagctg ggtgcgccag     180
gcccctggca agggactcgt gtgggtggga gagatcaacc ccagcagcag caccatcaac     240
tacgcccccc gcctgaagga caagttcacc atcagcagag acaacgccaa gaacaccctg     300
tacctgcaga tgaacagcct gcgggccgag gacaccgccg tgtactattg tgccagcctg     360
tactacgact acggcgacgc ctacgattac tggggccagg gcacactggt gactgttagc     420
tccggcagca ccagcggctc cggcaagcct ggctctggcg agggcagcac aaagggagag     480
atcgtgatga cacagagccc tgccaccctg agcgtgtccc aggcgaaag agctaccctg     540
agctgcaagg ccagcagag cgtggaaagc aacgtggcct ggtatcagca gaagcccgga     600
caggctcctc gggccctgat ctacagcgcc agcctgagat cagcggcat ccccgccagg     660
ttttccggat ctggcagcgg caccgagttc accctgacaa tcagcagcct gcagagcgag     720
gactttgccg tgtattactg ccagcagtac aacaactacc ccctgacctt cggagccggc     780
accaagctgg agctgaagga gagcaagtac ggccctccct gccccccttg ccctgccccc     840
gagttcgagg gcggacccag cgtgttcctg ttcccccca agcccaagga caccctgatg     900
atcagccgga cccccgaggt gacctgcgtg gtggtggacg tgagccagga agatcccgag     960
gtccagttca attggtacgt ggacggcgtg gaagtgcaca acgccaagac caagcccaga    1020
gaggaacagt tcaacagcac ctaccgggtg gtgtctgtgc tgaccgtgct gcaccaggac    1080
tggctgaacg gcaaagaata caagtgcaag gtgtccaaca gggcctgcc cagcagcatc    1140
gaaaagacca tcagcaaggc caagggccag cctcgcgagc cccaggtgta ccccctgcct    1200
ccctcccagg aagagatgac caagaaccag gtgtccctga cctgcctggt gaagggcttc    1260
taccccagcg acatcgccgt ggagtgggag agcaacggcc agcctgagaa caactacaag    1320
accaccccctc ccgtgctgga cagcgacggc agcttcttcc tctacagccg gctgaccgtg    1380
gacaagagcc ggtggcagga aggcaacgtc tttagctgca gcgtgatgca cgaggccctg    1440
cacaaccact acacccagaa gagcctgagc ctgtccctgg gcaagttttg ggtgctggtg    1500
gtggttggtg gagtcctggc ttgctatagc ttgctagtaa cagtggcctt tattattttc    1560
tgggtgagga gtaagaggag caggctcctg cacagtgact acatgaacat gactccccgt    1620
cgacccgggc ccacccgcaa gcattaccag ccctatgccc caccacgcga cttcgcagcc    1680
tatcgctccc tgagagtgaa gttcagcagg agcgcagacg cccccgcgta ccagcagggc    1740
cagaaccagc tctataacga gctcaatcta ggacgaagag aggagtacga tgttttggac    1800
aagagacgtg gccgggaccc tgagatgggg ggaaagccga aaggaagaa ccctcaggaa    1860
ggcctgtaca atgaactgca gaaagataag atggcggagg cctacagtga gattgggatg    1920
aaaggcgagc gccggagggg caaggggcac gatggccttt accagggtct cagtacagcc    1980
accaaggaca cctacgacgc ccttcacatg caggccctgc cccctcgctg a             2031
```

<210> SEQ ID NO 90  
<211> LENGTH: 1701  
<212> TYPE: DNA  
<213> ORGANISM: Artificial Sequence  
<220> FEATURE:  
<223> OTHER INFORMATION: construct

<400> SEQUENCE: 90

```
atggatttcc aggtgcagat cttcagcttc ctgctgatct ccgccagcgt gatcatgagc      60
cgcgaggtgc agctggtgga atctggcgga ggactggtgc agcctggcgg ctctctgaga     120
ctgtcttgtg ccgccagcgg cttcaccttc agccggtact ggtttagctg ggtgcgccag     180
gcccctggca agggactcgt gtgggtggga gagatcaacc ccagcagcag caccatcaac     240
tacgccccca gcctgaagga caagttcacc atcagcagag acaacgccaa gaacaccctg     300
tacctgcaga tgaacagcct gcgggccgag gacaccgccg tgtactattg tgccagcctg     360
tactacgact acggcgacgc ctacgattac tggggccagg gcacactggt gactgttagc     420
tccggcagca ccagcggctc cggcaagcct ggctctggcg agggcagcac aaagggagag     480
atcgtgatga cacagagccc tgccacccctg agcgtgtccc aggcgaaag agctaccctg     540 agctgcaagg ccagccagag cgtggaaagc aacgtggcct ggtatcagca gaagcccgga     600
caggctcctc gggccctgat ctacagcgcc agcctgagat tcagcggcat ccccgccagg     660
ttttccggat ctggcagcgg caccgagttc accctgacaa tcagcagcct gcagagcgag     720
gactttgccg tgtattactg ccagcagtac aacaactacc ccctgacctt cggagccggc     780
accaagctgg agctgaagga gagcaagtac ggccctccct gccccccttg ccctggccag     840
cctcgcgagc cccaggtgta caccctgcct ccctcccagg aagagatgac caagaaccag     900
gtgtccctga cctgcctggt gaagggcttc taccccagcg acatcgccgt ggagtgggag     960
agcaacggcc agcctgagaa caactacaag accaccctc ccgtgctgga cagcgacggc    1020
agcttcttcc tctacagccg gctgaccgtg gacaagagcc ggtggcagga aggcaacgtc    1080
tttagctgca gcgtgatgca cgaggccctg cacaaccact acacccagaa gagcctgagc    1140
ctgtccctgg gcaagttttg ggtgctggtg gtggttggtg gagtcctggc ttgctatagc    1200
ttgctagtaa cagtggcctt tattattttc tgggtgagga gtaagaggag caggctcctg    1260
cacagtgact acatgaacat gactccccgt cgacccgggc ccaccccgcaa gcattaccag    1320 ccctatgccc caccacgcga cttcgcagcc tatcgctccc tgagagtgaa gttcagcagg    1380
agcgcagacg cccccgcgta ccagcagggc cagaaccagc tctataacga gctcaatcta    1440
ggacgaagag aggagtacga tgttttggac aagagacgtg gccgggaccc tgagatgggg    1500
ggaaagccga aaggaagaa ccctcaggaa ggcctgtaca tgaactgca gaaagataag    1560 atggcggagg cctacagtga gattgggatg aaaggcgagc gccggagggg caaggggcac    1620
gatggccttt accagggtct cagtacagcc accaaggaca cctacgacgc ccttcacatg    1680
caggccctgc cccctcgctg a                                              1701
```

<210> SEQ ID NO 91
<211> LENGTH: 1380
<212> TYPE: DNA
<213> ORGANISM: Artificial Sequence
<220> FEATURE:
<223> OTHER INFORMATION: construct

<400> SEQUENCE: 91

```
atggatttcc aggtgcagat cttcagcttc ctgctgatct ccgccagcgt gatcatgagc      60
cgcgaggtgc agctggtgga atctggcgga ggactggtgc agcctggcgg ctctctgaga     120
ctgtcttgtg ccgccagcgg cttcaccttc agccggtact ggtttagctg ggtgcgccag     180
gcccctggca agggactcgt gtgggtggga gagatcaacc ccagcagcag caccatcaac     240
tacgccccca gcctgaagga caagttcacc atcagcagag acaacgccaa gaacaccctg     300
tacctgcaga tgaacagcct gcgggccgag gacaccgccg tgtactattg tgccagcctg     360
```

```
tactacgact acggcgacgc ctacgattac tggggccagg gcacactggt gactgttagc    420
tccggcagca ccagcggctc cggcaagcct ggctctggcg agggcagcac aaagggagag    480
atcgtgatga cacagagccc tgccaccctg agcgtgtccc aggcgaaag agctaccctg     540 agctgcaagg ccagccagag cgtggaaagc aacgtggcct ggtatcagca aagcccgga    600 caggctcctc gggccctgat ctacagcgcc agcctgagat tcagcggcat ccccgccagg    660
ttttccggat ctggcagcgg caccgagttc accctgacaa tcagcagcct gcagagcgag    720
gactttgccg tgtattactg ccagcagtac aacaactacc ccctgacctt cggagccggc    780
accaagctgg agctgaagga gagcaagtac ggccctccct gccccccttg ccctttttgg    840
gtgctggtgg tggttggtgg agtcctggct tgctatagct tgctagtaac agtggccttt    900
attattttct gggtgaggag taagaggagc aggctcctgc acagtgacta catgaacatg    960
actccccgtc gacccgggcc cacccgcaag cattaccagc cctatgcccc accacgcgac   1020
ttcgcagcct atcgctccct gagagtgaag ttcagcagga gcgcagacgc cccgcgtac   1080 cagcagggcc agaaccagct ctataacgag ctcaatctag gacgaagaga ggagtacgat   1140
gttttggaca agagacgtgg ccgggacccct gagatggggg gaaagccgag aaggaagaac   1200
cctcaggaag gcctgtacaa tgaactgcag aaagataaga tggcggaggc ctacagtgag   1260
attgggatga aggcgagcg ccggagggc aaggggcacg atggcctta ccagggtctc     1320 agtacagcca ccaaggacac ctacgacgcc cttcacatgc aggccctgcc ccctcgctga   1380
```

<210> SEQ ID NO 92
<211> LENGTH: 2040
<212> TYPE: DNA
<213> ORGANISM: Artificial Sequence
<220> FEATURE:
<223> OTHER INFORMATION: construct

<400> SEQUENCE: 92

```
atggatttcc aggtgcagat cttcagcttc ctgctgatct ccgccagcgt gatcatgagc    60
cgcgaggtgc agctggtgga atctggcgga ggactggtgc agcctggcgg ctctctgaga   120
ctgtcttgtg ccgccagcgg cttcaccttc agccggtact ggtttagctg ggtgcgccag   180 gccccctggca agggactcgt gtgggtggga gagatcaacc ccagcagcag caccatcaac   240
tacgccccca gcctgaagga caagttcacc atcagcagag acaacgccaa gaacaccctg    300
tacctgcaga tgaacagcct gcgggccgag gacaccgccg tgtactattg tgccagcctg    360
tactacgact acggcgacgc ctacgattac tggggccagg gcacactggt gactgttagc    420
tccggcagca ccagcggctc cggcaagcct ggctctggcg agggcagcac aaagggagag    480
atcgtgatga cacagagccc tgccaccctg agcgtgtccc aggcgaaag agctaccctg     540 agctgcaagg ccagccagag cgtggaaagc aacgtggcct ggtatcagca aagcccgga    600 caggctcctc gggccctgat ctacagcgcc agcctgagat tcagcggcat ccccgccagg    660
tttagcggct ctggcagcgg caccgagttc accctgacaa tcagcagcct gcagagcgag    720
gactttgccg tgtattactg ccagcagtac aacaactacc ccctgacctt cggagccggc    780
accaagctgg agctgaagcc tgccagcct aagagccccg acaagaccca cacctgtccc    840
ccttgtcctg cccctccagt ggctggccct agcgtgttcc tgttcccccc aaagcccaag    900 gatacccctga tgatcgcccg gacccccgaa gtcacatgcg tggtggtgga cgtgagccac    960
gaagaccctg aggtcaagtt caactggtac gtggacggcg tggaggtgca taatgccaag   1020
```

| | | |
|---|---|---|
| acaaagccgc gggaggagca gtacaacagc acgtaccgtg tggtcagcgt cctcaccgtc | 1080 | |
| ctgcaccagg actggctgaa tggcaaggag tacaagtgca aggtctccaa caaagccctc | 1140 | |
| ccagccccca tcgagaaaac catctccaaa gccaagggc agccccgaga ccacaggtg | 1200 | |
| tacaccctgc ccccatcccg ggatgagctg accaagaacc aggtgtccct gacctgcctc | 1260 | |
| gtgaagggct tctacccctc cgatatcgcc gtggaatggg agagcaatgg ccagcccgag | 1320 | |
| aacaactaca agaccacccc ccctgtgctg gacagcgacg gctcattctt cctgtacagc | 1380 | |
| aagctgacag tggacaagag ccggtggcag cagggcaacg tgttcagctg cagcgtgatg | 1440 | |
| cacgaggctc tgcacaacca ctacacccag aagtccctga gcagcctgag cccaggcaag | 1500 | |
| aagatctaca tctgggcccc tctggccggc acctgtggcg tgctgctgct gtctctcgtg | 1560 | |
| atcacactgt actgcaagcg gggcagaaag aagctgctgt acatcttcaa gcagcccttc | 1620 | |
| atgcggcccg tgcagaccac ccaggaagag gacggctgct cctgcagatt ccccgaggaa | 1680 | |
| gaagaaggcg gctgcgagct gctgcgcgtg aagttttcta gaagcgccga cgcccctgcc | 1740 | |
| taccagcagg gccagaacca gctgtacaac gagctgaacc tgggcagacg ggaagagtac | 1800 | |
| gacgtgctgg ataagcggag aggccgggac cctgagatgg gcggcaagcc tagaagaaag | 1860 | |
| aaccccccagg aaggcctgta taacgaactg cagaaagaca gatggccga ggcctacagc | 1920 | |
| gagatcggaa tgaagggcga gcggagaaga ggcaagggcc acgatggact gtaccagggc | 1980 | |
| ctgagcaccg ccaccaagga cacctatgac gccctgcaca tgcaggctct gcccccagga | 2040 | |

<210> SEQ ID NO 93
<211> LENGTH: 2040
<212> TYPE: DNA
<213> ORGANISM: Artificial Sequence
<220> FEATURE:
<223> OTHER INFORMATION: construct

<400> SEQUENCE: 93

| | | |
|---|---|---|
| atggatttcc aggtgcagat cttcagcttc ctgctgatct ccgccagcgt gatcatgagc | 60 | |
| cgcgagatcg tgatgacaca gagccctgcc accctgagcg tgtccccagg cgaaagagct | 120 | |
| accctgagct gcaaggccag ccagagcgtg gaaagcaacg tggcctggta tcagcagaag | 180 | |
| cccggacagg ctcctcgggc cctgatctac agcgccagcc tgagattcag cggcatcccc | 240 | |
| gccaggttta gcggctctgg cagcggcacc gagttcaccc tgacaatcag cagcctgcag | 300 | |
| agcgaggact ttgccgtgta ttactgccag cagtacaaca ctacccccct gaccttcgga | 360 | |
| gccggcacca gctggagct gaagggcagc caccggct ccggcaagcc tggctctggc | 420 | |
| gagggcagca caagggaga ggtgcagctg gtggaatctg gcggaggact ggtgcagcct | 480 | |
| ggcggctctc tgagactgtc ttgtgccgcc agcggcttca ccttcagccg gtactggttt | 540 | |
| agctgggtgc gccaggcccc tggcaaggga ctcgtgtggg tgggagagat caaccccagc | 600 | |
| agcagcacca tcaactacgc ccccagcctg aaggacaagt tcaccatcag cagagacaac | 660 | |
| gccaagaaca cctgtacct gcagatgaac agcctgcggg ccgaggacac cgccgtgtac | 720 | |
| tattgtgcca gcctgtacta cgactacggc gacgcctacg attactgggg ccagggcaca | 780 | |
| ctggtgactg ttagctcccc tgccgagcct aagagcccg acaagaccca cacctgtccc | 840 | |
| ccttgtcctg cccctccagt ggctggccct agcgtgttcc tgttccccc aaagcccaag | 900 | |
| gataccctga tgatcgcccg gacccccgaa gtcacatgcg tggtggtgga cgtgagccac | 960 | |
| gaagaccctg aggtcaagtt caactggtac gtggacggcg tggaggtgca taatgccaag | 1020 | |
| acaaagccgc gggaggagca gtacaacagc acgtaccgtg tggtcagcgt cctcaccgtc | 1080 | |

| | |
|---|---|
| ctgcaccagg actggctgaa tggcaaggag tacaagtgca aggtctccaa caaagccctc | 1140 |
| ccagcccca tcgagaaaac catctccaaa gccaaagggc agccccgaga ccacaggtg | 1200 |
| tacaccctgc ccccatcccg ggatgagctg accaagaacc aggtgtccct gacctgcctc | 1260 |
| gtgaagggct tctacccctc cgatatcgcc gtggaatggg agagcaatgg ccagcccgag | 1320 |
| aacaactaca agaccacccc ccctgtgctg gacagcgacg gctcattctt cctgtacagc | 1380 |
| aagctgacag tggacaagag ccggtggcag cagggcaacg tgttcagctg cagcgtgatg | 1440 |
| cacgaggctc tgcacaacca ctacacccag aagtccctga gcagcctgag cccaggcaag | 1500 |
| aagatctaca tctgggcccc tctggccggc acctgtggcg tgctgctgct gtctctcgtg | 1560 |
| atcacactgt actgcaagcg gggcagaaag aagctgctgt acatcttcaa gcagcccttc | 1620 |
| atgcggcccg tgcagaccac ccaggaagag gacggctgct cctgcagatt ccccgaggaa | 1680 |
| gaagaaggcg gctgcgagct gctgcgcgtg aagttttcta gaagcgccga cgcccctgcc | 1740 |
| taccagcagg gccagaacca gctgtacaac gagctgaacc tgggcagacg ggaagagtac | 1800 |
| gacgtgctgg ataagcggag aggccgggac cctgagatgg gcggcaagcc tagaagaaag | 1860 |
| aacccccagg aaggcctgta taacgaactg cagaaagaca gatggccga ggcctacagc | 1920 |
| gagatcggaa tgaagggcga gcggagaaga ggcaagggcc acgatggact gtaccagggc | 1980 |
| ctgagcaccg ccaccaagga cacctatgac gccctgcaca tgcaggctct gcccccagga | 2040 |

<210> SEQ ID NO 94
<211> LENGTH: 2040
<212> TYPE: DNA
<213> ORGANISM: Artificial Sequence
<220> FEATURE:
<223> OTHER INFORMATION: construct

<400> SEQUENCE: 94

| | |
|---|---|
| atggatttcc aggtgcagat cttcagcttc ctgctgatct ccgccagcgt gatcatgagc | 60 |
| cgcgaagtgc agctggtcga atctggagga ggcctggttc agcctggtgg cagccttagg | 120 |
| ctctcttgtg cagcctctgg ctttaccttc tcacggtatt ggttcagctg ggtgagacag | 180 |
| gctccaggga aaggtctggt gtgggtaggg agatataacc cagcagcag cacgatcaac | 240 |
| tatgctccgt cactgaaaga caagttcacc atttcccgcg ataatgccaa gaacactctc | 300 |
| tacttgcaga tgaattccct tcgagccgag gatacagcgg tgtactactg cgccagtctg | 360 |
| tactacgact atgggacgc atacgactat tggggacaag gcacactggt gactgttagc | 420 |
| tccggcagca ccagcggctc cggcaagcct ggctctggcg agggcagcac aaagggagag | 480 |
| atcgtgatga cccagtctcc tgctaccctg agcgtttctc ccggtgaaag ggccacactc | 540 |
| agctgcaaag cctctcaaag cgtggagagc aatgtcgcct ggtatcagca gaaacctggc | 600 |
| caagctccga gagcactgat ctattccgcg tcattgcgct tttccggcat accagcacgg | 660 |
| tttagtggct cagggagtgg gactgagttc actctgacga ttagctccct tcagtcagag | 720 |
| gatttcgccg tgtactactg tcagcagtac aacaactatc ccctcacatt cggagctgga | 780 |
| accaagctgg aactgaagcc tgccgagcct aagagcccg acaagaccca cacctgtccc | 840 |
| ccttgtcctg cccctccagt ggctggccct agcgtgttcc tgttcccccc aaagcccaag | 900 |
| gataccctga tgatcgcccg gacccccgaa gtcacatgcg tggtggtgga cgtgagccac | 960 |
| gaagaccctg aggtcaagtt caactggtac gtggacggcg tggaggtgca taatgccaag | 1020 |
| acaaagccgc gggaggagca gtacaacagc acgtaccgtg tggtcagcgt cctcaccgtc | 1080 |

-continued

```
ctgcaccagg actggctgaa tggcaaggag tacaagtgca aggtctccaa caaagccctc    1140
ccagccccca tcgagaaaac catctccaaa gccaaagggc agccccgaga accacaggtg    1200
tacaccctgc ccccatcccg ggatgagctg accaagaacc aggtgtccct gacctgcctc    1260
gtgaagggct tctaccccctc cgatatcgcc gtggaatggg agagcaatgg ccagcccgag    1320
aacaactaca agaccacccc ccctgtgctg gacagcgacg gctcattctt cctgtacagc    1380
aagctgacag tggacaagag ccggtggcag cagggcaacg tgttcagctg cagcgtgatg    1440
cacgaggctc tgcacaacca ctacacccag aagtccctga gcagcctgag cccaggcaag    1500
aagatctaca tctgggcccc tctggccggc acctgtggcg tgctgctgct gtctctcgtg    1560
atcacactgt actgcaagcg gggcagaaag aagctgctgt acatcttcaa gcagcccttc    1620
atgcggcccg tgcagaccac ccaggaagag gacggctgct cctgcagatt ccccgaggaa    1680
gaagaaggcg gctgcgagct gctgcgcgtg aagtttcta gaagcgccga cgcccctgcc    1740
taccagcagg gccagaacca gctgtacaac gagctgaacc tgggcagacg ggaagagtac    1800
gacgtgctgg ataagcggag aggccgggac cctgagatgg gcggcaagcc tagaagaaag    1860 aaccccagg aaggcctgta taacgaactg cagaaagaca agatggccga ggcctacagc    1920
gagatcggaa tgaagggcga gcggagaaga ggcaagggcc acgatggact gtaccagggc    1980
ctgagcaccg ccaccaagga cacctatgac gccctgcaca tgcaggctct gccccccaga    2040
```

The invention claimed is:

1. A chimeric antigen receptor polypeptide (CAR), wherein the CAR comprises:
   i. an extracellular antigen-binding domain, comprising an antibody or antibody fragment that binds a human B Cell Maturation Antigen (BCMA) polypeptide;
   ii. a transmembrane domain; and
   iii. an intracellular domain, and wherein the extracellular antigen-binding domain comprises:
   (I) a variable heavy chain (VH) domain comprising:
      (a) a heavy chain complementary determining region 1 (H-CDR1) comprising SEQ ID NO: 34 (RYWX1S), wherein X1 is I, F, L, V, Y, C, G, A, or M;
      (b) a heavy chain complementary determining region 2 (H-CDR2) comprising amino acids 50-67 of SEQ ID NO: 53 (EINPZ2SSTINYAPSLKX11X12), wherein Z2 is S, N, T, G, or D; X11 is D; and X12 is K or R; and
      (c) a heavy chain complementary determining region 3 (H-CDR3) comprising SEQ ID NO: 36 (SLYX4DYGDAX5DYW), wherein X4 is Y, and X5 is Y, L, F, I, V, A, C, or M; and
   (II) a variable light chain (VL) domain comprising:
      (a) a light chain complementary determining region 1 (L-CDR1) comprising SEQ ID NO: 37 (KASQSVX1X2NVA), wherein X1X2 is ES or DS;
      (b) a light chain complementary determining region 2 (L-CDR2) comprising SEQ ID NO: 29 (SASLRFS), and
      (c) a light chain complementary determining region 3 (L-CDR3) comprising SEQ ID NO: 30 (QQYNNYPLTFG); and
   wherein expression of the CAR in an immune effector cell is effective to increase cytotoxicity of the immune effector cell to both (i) multiple myeloma cells, and (ii) mantle cell lymphoma cells.

2. The CAR according to claim 1, wherein the CAR transduces an intracellular signal in an immune effector cell in response to binding human BCMA.

3. The CAR according to claim 2, wherein the extracellular antigen-binding domain further comprises a linker polypeptide positioned between the VH and VL domains.

4. The CAR according to claim 3, wherein said linker is selected from a Whitlow (SEQ ID NO: 13; GST-SGSGKPGSGEGSTKG) or Gly-Ser (SEQ ID NO: 14; SSGGGGSGGGGSGGGGS) linker, or linkers with at least 80% sequence identity to SEQ ID NO: 13 or 14.

5. The CAR according to claim 2, wherein the VH domain comprises:
   (i) H-CDR1 comprising SEQ ID NO: 34 (RYWX1S), wherein X1 is I, F, or M;
   (ii) H-CDR2 comprising amino acids 50-67 of SEQ ID NO: 53 (EINPZ2SSTINYAPSLKX11X12), wherein Z2 is S, N, or D; X11 is D; and X12 is K or R; and
   (iii) H-CDR3 comprising SEQ ID NO: 36 (SLYX4DYGDAX5DYW), wherein X4 is Y, and X5 is Y or M,
   and the VL domain comprises:
   (i) L-CDR1 comprising SEQ ID NO: 37 (KASQSVX1X2NVA), wherein X1X2 is ES or DS;
   (ii) L-CDR2 comprising SEQ ID NO: 29 (SASLRFS); and
   (iii) L-CDR3 comprising SEQ ID NO: 30 (QQYNNYPLTFG).

6. The CAR according to claim 5, comprising the following sequences:
   i. H-CDR1: SEQ ID NO: 25 (RYWFS),
   ii. H-CDR2: SEQ ID NO: 26 (EINPSSSTINYAPSLKDK),
   iii. H-CDR3: SEQ ID NO: 27 (SLYYDYGDAYDYW),
   iv. L-CDR1: SEQ ID NO: 28 (KASQSVESNVA),
   v. L-CDR2: SEQ ID NO: 29 (SASLRFS), and
   vi. L-CDR3: SEQ ID NO: 30 (QQYNNYPLTFG).

7. The CAR according to claim 1, comprising a VH domain with at least 80% sequence identity to SEQ ID NO: 11:

(EVQLVESGGGLVQPGGSLRLSCAASGFTFSRYWFSWVRQAPGKGLVWVG

EINPSSSTINYAPSLKDKFTISRDNAKNTLYLQMNSLRAEDTAVYYCASL

YYDYGDAYDYWGQGTLVTVSS);

and a VL domain with at least 80% sequence identity to SEQ ID NO: 12:

(EIVMTQSPATLSVSPGERATLSCKASQSVESNVAWYQQKPGQAPRALIY

SASLRFSGIPARFSGSGSGTEFTLTISSLQSEDFAVYYCQQYNNYPLTFG

AGTKLELK).

8. The CAR according to claim 7, wherein the VH domain comprises at least W36, E50, L99, Y100, Y101 and A106 of SEQ ID NO: 11, and the VL domain comprises at least S31, A34, S50, L53, Q89, Y91, Y94 and L96 of SEQ ID NO: 12.

9. The CAR according to claim 7, wherein the VH domain comprises at least the CDR sequences of SEQ ID NOs: 25 to 27, and the VL domain comprises at least the CDR sequences of SEQ ID NOs: 28 to 30.

10. The CAR according to claim 7, comprising the VH and VL domains according to SEQ ID NO: 11 and SEQ ID NO: 12, respectively.

11. The CAR according to claim 1, wherein when said CAR is expressed in a genetically modified immune cell, said immune cell binds human BCMA on the surface of a B-cell non-Hodgkin's lymphoma (B-NHL) via said CAR and is activated, thereby inducing cytotoxic activity against said B-NHL.

12. The CAR according to claim 11, wherein the B-NHL is JeKo-1, DOHH-2, SU-DHL4, JVM-3 and/or MEC-1 cell lines.

13. The CAR according to claim 1, further comprising a spacer polypeptide positioned between the extracellular antigen-binding domain and the transmembrane domain, wherein said spacer is selected from the group consisting of:

a. IgG1-CD28 spacer (SEQ ID NO 15;
PAEPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKK), b. IgG1Δ-4-1BB spacer (SEQ ID NO 16;
PAEPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSSLSPGKK), c. IgG4 (Hi-CH2—CH3) spacer (SEQ ID NO 17;
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK), d. IgG4 (Hi-CH3) spacer (SEQ ID NO 18;
ESKYGPPCPPCPGQPREPQVYTLPPSQEEMTKNQVSLTCLVKGFYPSDIA

VEWESNGQPENNYKTTPPVLDSDGSFFLYSRLTVDKSRWQEGNVFSCSVM

HEALHNHYTQKSLSLSLGK), e. IgG4 (Hi) spacer (SEQ ID NO 19;
ESKYGPPCPPCP), and a spacer with at least 80% sequence identity to any one of SEQ ID NOs: 15 to 19.

14. The CAR according to claim 1, wherein the transmembrane domain is selected from the group consisting of a CD8α domain (SEQ ID NO: 20; IYIWAPLAGTCGVLLLSLVITLYC), a CD28 domain (SEQ ID NO: 21; FWVLVVVGGVLACYSLLVTVAFIIFWV) and a transmembrane domain with at least 80% sequence identity to SEQ ID NO: 20 or 21.

15. The CAR according to claim 1, wherein the intracellular domain comprises a co-stimulatory domain selected from the group consisting of a 4-1BB co-stimulatory domain (SEQ ID NO: 22;
KRGRKKLLY-
IFKQPFMRPVQTTQEEDGCSCRFPEEEEGGCEL),
a CD28 co-stimulatory domain (SEQ ID NO: 23; RSKRSRLLHSDYMNMTPRRPGPTRKHYQPYAP-
PRDFAAYRS) and a co-stimulatory domain with at least 80% sequence identity to SEQ ID NO: 22 or 23.

16. The CAR according to claim 1, further comprising a signaling domain, wherein said signaling domain comprises a CD3zeta signaling domain (SEQ ID NO: 24;
LRVKFSRSADAPAYQQGQNQLYNELNLGRREEY-
DVLDKRRGRDPEMGGKPRRKNPQE GLY-
NELQKDKMAEAYSEIGMKGERRRGKGHDG-
LYQGLSTATKDTYDALHMQALPPR) or a signaling domain with at least 80% sequence identity to SEQ ID NO: 24.

17. The CAR according to claim 1, further comprising a tandem co-stimulatory domain comprising a 4-1BB co-stimulatory domain (SEQ ID NO: 22) and a CD28 co-stimulatory domain (SEQ ID NO: 23).

18. A method of treating a medical disorder associated with the presence of pathogenic B cells comprising administering to a subject in need thereof a genetically modified immune cell comprising the CAR according to claim 1.

19. The method according to claim 18, wherein the medical disorder is multiple myeloma, non-Hodgkin's lymphoma, systemic lupus erythematosus (SLE) or rheumatoid arthritis.

20. The CAR according to claim 1, wherein the multiple myeloma cells are MM.1S cells, and the mantle cell lymphoma cells are JeKo-1 cells.

21. The CAR according to claim 1, wherein the increased cytotoxicity comprises degranulation of the immune effector cell in the presence of the multiple myeloma cells or the mantle cell lymphoma cells.

22. The CAR according to claim 1, wherein the immune effector cell is or an NK cell.

23. The CAR according to claim 1, wherein the immune effector cell is a T cell.

* * * * *

UNITED STATES PATENT AND TRADEMARK OFFICE
CERTIFICATE OF CORRECTION

Page 1 of 2

PATENT NO. : 12,048,718 B2
APPLICATION NO. : 16/307854
DATED : July 30, 2024
INVENTOR(S) : Armin Rehm et al.

It is certified that error appears in the above-identified patent and that said Letters Patent is hereby corrected as shown below:

On the Title Page

Column 1 (item (73) Assignee), Line 3, delete "GEMINSCHAFT," and insert -- GEMEINSCHAFT, --.

In the Specification

Column 5, Line 31, delete "Dicksinson)." and insert -- Dickinson). --.

Column 8, Line 27 (approx.), delete "Y." and insert -- Y, --.

Column 12, Line 24, delete "Y." and insert -- Y, --.

Column 12, Line 53 (approx.), delete "Y." and insert -- Y, --.

Column 17, Line 46, delete "Y." and insert -- Y, --.

Column 17, Line 62, delete "FIL" and insert -- FTL --.

Column 19, Line 15, delete "; and/or" and insert -- . --.

Column 23-24, Line 6, delete "Y." and insert -- Y, --.

Column 23-24, Line 29, delete "Y." and insert -- Y, --.

Column 25-26, Line 41, delete "Y." and insert -- Y, --.

Column 41, Line 50, delete "plasmocytoma," and insert -- plasmacytoma, --.

Column 44, Line 21, delete "Oletuzumab," and insert -- elotuzumab, --.

Signed and Sealed this
Fourteenth Day of January, 2025

Derrick Brent
*Acting Director of the United States Patent and Trademark Office*

CERTIFICATE OF CORRECTION (continued)
U.S. Pat. No. 12,048,718 B2

Column 44, Line 21, delete "Blimatumomab)" and insert -- Blinatumomab) --.

Column 49, Line 31, delete "CD28" and insert -- CD28. --.

Column 55, Line 19, delete "(ThI)" and insert -- (Th1) --.

Column 59, Line 15, delete "Ringers" and insert -- Ringer's --.

Column 60, Line 5, delete "Extramedullar" and insert -- extramedullary --.

Column 60, Line 67, delete "cutanous" and insert -- cutaneous --.

Column 61, Line 2, delete "vasculitidies," and insert -- vasculitides, --.

Column 61, Line 4, delete "Hennoch" and insert -- Henoch --.

Column 61, Line 9 (approx.), delete "ateritis," and insert -- arthritis, --.

Column 61, Line 10 (approx.), delete "Eythema" and insert -- Erythema --.

Column 64, Line 58, delete "pg" and insert -- µg --.

Column 64, Line 66, delete "pg" and insert -- µg --.

Column 64, Line 66, delete "pg" and insert -- µg --.

Column 65, Line 33, delete "/pµl" and insert -- /µl --.

Column 68, Line 21, delete "(FIG." and insert -- (FIGS. --.

Column 68, Line 41, delete "(FIG." and insert -- (FIGS. --.

In the Claims

Column 167, Line 41 (approx.), Claim 13, delete "IgG1" and insert -- IgG1Δ --.

Column 168, Line 36, Claim 16, delete "E GLY-" and insert -- EGLY --.

Column 168, Line 61, Claim 22, delete "is or an" and insert -- is an --.